(12) United States Patent
Schneider et al.

(10) Patent No.: US 8,017,355 B2
(45) Date of Patent: Sep. 13, 2011

(54) MANNITOL INDUCED PROMOTER SYSTEMS IN BACTERIAL HOST CELLS

(75) Inventors: J. Carrie Schneider, San Diego, CA (US); Bettina Rosner, San Diego, CA (US)

(73) Assignee: Pfenex, Inc., San Diego, CA (US)

( * ) Notice: Subject to any disclaimer, the term of this patent is extended or adjusted under 35 U.S.C. 154(b) by 120 days.

(21) Appl. No.: 12/330,723

(22) Filed: Dec. 9, 2008

(65) Prior Publication Data

US 2009/0162899 A1 Jun. 25, 2009

Related U.S. Application Data

(62) Division of application No. 11/447,553, filed on Jun. 6, 2006, now Pat. No. 7,476,532.

(60) Provisional application No. 60/687,763, filed on Jun. 6, 2005.

(51) Int. Cl.
*C12P 21/00* (2006.01)
*C12N 1/21* (2006.01)
*C07H 21/04* (2006.01)

(52) U.S. Cl. .................. 435/71.2; 435/252.34; 536/24.1

(58) Field of Classification Search ........................ None
See application file for complete search history.

(56) References Cited

OTHER PUBLICATIONS

Brunker, P., et al., "Structure and Function of the Genes Involved in Mannitor, Arabitol and Glucitol Utilization from *Pseudomonoas fluorescens* DSM50105," *Gene*, vol. 206, No. 1, pp. 117-126, Jan. 5, 1998.
Hannig, G., and Makrides, S.C., "Strategies for Optimizing Heterologous Protein Expression in *Escherichia coli*," *Trends Biotechnol.*, Feb. 1998, pp. 54-60, vol. 16, No. 2.
Makrides, S.C., "Strategies for Achieving High-level Expression of Genes in *Escherichia coli*," Microbiol. Rev., Sep. 1996, pp. 512-538, vol. 60, No. 3.
Sanchez-Romero, J., and De Lorenzo, V., "Genetic Engineering of Nonpathogenic *Pseudomonas* Strains as Biocatalysts for Industrial and Environmental Process," in *Manual of Industrial Microbiology and Biotechnology*, Demain, A, and Davies J., eds. ASM Press, Washington, D.C., 1999, pp. 460-474.
Schneider, J.C., et al., Auxotrophic Markers PhyR and ProC can Replace Antibiotic Markers on Protein Production Plasmids in High Dell Density *Pseudomonas fluorescens* Fermentation, Biotechnol. Prog., Mar.-Apr. 2005, pp. 343-348, vol. 21, No. 2.
Schweizer, H.P., "Vectors to Express Foreign Genes and Techniques to Monitor Gene Expression in Pseudomonads, " *Curr. Opin Biotechnol.*, Oct. 2001, pp. 438-445, vol. 12, No. 5.
Slater, R. , and Williams., R., "The Expression of Foreign DNA in Bacteria", in Molecular Biology and Biotechnology, Walker, J. and Rapley, R., eds., The Royal Society of Chemistry, Cambridge, UK, 2000, pp. 125-154.
Stevens, R.C., "Design of High-throughput Methods of Protein Production for Structural Biology," *Structure*, Sep. 15, 2000, pp. R177-R185, vol. 8, No. 9.
Landry et al. (2003) "Safety evaluation of an alpha-amylase enzyme preparation derived from the archaeal order Thermococcales as expressed in *Pseudomonas fluorescens* biovar I" *Regulatory Toxicology and Pharmacology* 37(1): pp. 149-168.
EMBL Database Accession No. AF007800, published Aug. 13, 1997.

*Primary Examiner* — Nancy Vogel
(74) *Attorney, Agent, or Firm* — Wilson Sonsini Goodrich & Rosati

(57) ABSTRACT

The present invention provides methods for producing recombinant peptides in a bacterial host utilizing a mannitol, arabitol, glucitol, or glycerol-inducible promoter, wherein the host bacterial cell that produces the peptide has been rendered incapable of degrading or metabolizing mannitol, arabitol, or glucitol, or derivatives or analogues thereof. The present invention provides bacterial cells that have been genetically altered to inhibit the metabolism or degradation of mannitol, glucitol, or arabitol, or derivatives or analogues thereof. The present invention utilizes mannitol, arabitol, glucitol, or glycerol to induce expression of a target polypeptide from an inducible promoter, allowing for the use of an inexpensive and stable carbon source inducer in the fermentation processes for the production of recombinant peptides.

2 Claims, 17 Drawing Sheets

```
                                                   -35                                                    -10
DSM50106 promoter  ACGA gtgcaaaaagtatc AG t CCAA gtgc TCCCA a G g A tttgtc ACAACCCGTTTGAAGGC tgtaatc AA
MB101 promoter     ACGA gtgcaaaaagtatc AG t AAGC gtgc TCCCA a G g A tttgtc ACCGCGTTTTGAAGGC tgtaatc AA
PfO-1 promoter     CCGA gtgcaaaaagtatc GA t TCAA gtgc TAGGG a T g A tttgtc AGCCCTGCGTCAGAAGGC tgtaatc AG
PAO1 promoter      GGCG gtgcaaaaagtatc GG t CGAA gtgc AGTCG a G g C tttgtc GGTTGCGTGACGCGCCTG tgtaatc GG DSM50106 promoter  CGCACACTCTTCCTGACTCCCCGTAgGAAG acacaaCaacaataa CTgtcCtTcC--gTAGccc--cTggGCGcGgaa
MB101 promoter     CGCACACTCTTCCTGACTCCCCGTAgGAAG acacaaCaacaataa CCgtcCtTcT--gTAGcccTcTggGCGcGgaa
PfO-1 promoter     TGCACATTCTT------CCCCGCCGgAAGA acacaaAaacaataa CTgtcCtTcT--gCCCcccGcCgcCggGTGcAgaa
PAO1 promoter      ---------------------CAGC---gAGCG acacaaAaacaataa -TgtcTtCcGcGCCgccGcCggCC--cGgaa mtlE
                   RBS       start codon
DSM50106 promoter  ATggagtGcGc--gatgAaGTTcAcAGCA    SEQ. ID. No. 31
MB101 promoter     ATggagtGcGc--gatgAaGTTcAcAGCA    SEQ. ID. No. 32
PfO-1 promoter     AAggagtGcAc--gatgCaACCcAcTGCA    SEQ. ID. No. 33
PAO1 promoter      GAggagtTcAcCgatgAaCGAcTcGATC    SEQ. ID. No. 34
```

FIGURE 4

MANNITOL INDUCED PROMOTER SYSTEMS IN BACTERIAL HOST CELLS

CROSS-REFERENCE TO RELATED APPLICATIONS

This application is a divisional of U.S. application Ser. No. 11/447,553, filed Jun. 6, 2006 now U.S. Pat. No. 7,476,532, which claims the benefit of U.S. Provisional Application No. 60/687,763, filed Jun. 6, 2005, each of which is hereby incorporated in its entirety by reference herein.

REFERENCE TO SEQUENCE LISTING SUBMITTED ELECTRONICALLY

The official copy of the sequence listing is submitted electronically via EFS-Web as an ASCII formatted sequence listing with a file named "365868_SequenceListing.txt", created on Dec. 4, 2008, and having a size of 8 kilobytes and is filed concurrently with the specification. The sequence listing contained in this ASCII formatted document is part of the specification and is herein incorporated by reference in its entirety.

FIELD OF THE INVENTION

The present invention relates to the field of recombinant peptide production. In particular, the present invention provides for the improved production of recombinant peptides utilizing a mannitol, glucitol, or arabitol-inducible promoter, wherein the host cell expressing the peptide from the promoter is rendered deficient in its ability to metabolize or degrade mannitol, glucitol, or arabitol, which is utilized to induce the promoter. In addition, the invention provides for improved bacterial host cells for the production of recombinant peptides, wherein the bacterial cell has been rendered deficient in its ability to metabolize or degrade mannitol, glucitol, or arabitol, or analogues or derivatives thereof.

BACKGROUND OF THE INVENTION

The use of bacterial cells to produce recombinant peptides is increasing in commercial importance. One of the goals in developing a bacterial expression system is the production of high quality target polypeptides quickly, efficiently, and abundantly. An ideal host cell for such an expression system would be able to efficiently utilize a carbon source for growth, efficiently produce a target polypeptide, quickly grow to high cell densities in a fermentation reaction, express the target polypeptide only when induced, and allow for the induction of the target polypeptide in an inexpensive and efficient manner.

One hurdle to the creation of the ideal host cell is overcoming inefficient and low level production of target polypeptides in the fermentation process. Controlling expression of the target peptide until optimal host cell densities and fermentation conditions are reached allows for a more efficient and larger yield of polypeptide. The reasons for this are several fold, including a more efficient utilization of a carbon source and the reduction of extended metabolic stresses on the host cell.

One way to control expression of target polypeptides during the fermentation process includes the use of inducible or regulatable promoters to control expression of the peptides. Promoters are regulatory nucleic acid sequences generally located upstream from the desired peptide coding sequence, directing the transcription of the nucleic acid. Promoters are generally classified as constitutive or regulated promoters. Regulated promoters include: (1) activatable promoters, which are inactive until an activator peptide binds to the 5' regulatory regions; and (2) repressible promoters, which are inactive while the 5' regulatory region is bound by a repressor peptide. Some genes or operons are regulated by more than one mechanism.

An inducible or regulatable promoter can be an essential component for the production of high levels of recombinant peptides in an efficient manner, since such regulatable promoters allow for cell densities to reach optimal levels prior to the induction of peptide production. Attributes of an ideal promoter can include: tight repression so that little or no target peptide is made during the growth phase; strong promoter activity after the addition of the inducer; low cost of induction; stability of the inducer in the cell culture medium so that the inducer need only be added once during the peptide accumulation phase of a fermentation process; easy passage of the inducer of the promoter through the cell membrane so that the external concentrations of the inducer are directly related to the internal concentration within the cell, and linearly related to peptide production; and ability to be used in tandem with other promoters. Such an ideal promoter allows recombinant peptides to be induced at high levels efficiently and inexpensively.

One regulatable promoter that has found widespread use in bacterial fermentation process for the production of recombinant peptides is the lac promoter, and its derivatives, especially the tac and trc promoters. In commercial fermentation systems using a lac-type promoter, the inducer isopropyl-β-D-1-thiogalactopyranoside ("IPTG") is almost universally employed. IPTG is, however, expensive and must be carefully controlled since it is significantly toxic to biological systems. Standard IPTG preparations are currently available at about USD $18 per gram or about USD $125 per 10 grams. In addition, standard IPTG preparations may contain dioxane, a toxin. Dioxane-free IPTG is available on the market, but costs roughly twice the price of standard IPTG. Furthermore, environmental and health regulatory issues arise in regard to the presence of IPTG in the fermentation, or in the protein purified from the fermentation, given the IPTG toxicity risks to humans, animals, and other biological organisms.

Because of the toxicities and costs associated with IPTG, alternative inducible promoter systems have been proposed for use in bacterial fermentation processes for the production of recombinant peptides. For example, promoters induced by high temperatures such as $\lambda P_R$ and $\lambda P_L$, tryptophan starvation such as trp, 1-arabinose such as araBAD, phosphate starvation such as phoA, nalidixic acid such as recA, osmolarity such as proU, glucose starvation such as cst-1, tetracycline such as tetA, pH such as cadA, anaerobic conditions such as nar, T4 infection such as T4 gene32, alkyl- or halo-benzoates such as Pm, alkyl- or halo-toluenes such as Pu, salicylates such as Psal, and oxygen such as VHb, have all been examined as alternatives to IPTG inducible promoters. See, for example, Makrides, S. C. (1996) Microbiol. Rev. 60, 512-538; Hannig G. & Makrides, S. C. (1998) TIBTECH 16, 54-60; Stevens, R. C. (2000) Structures 8, R177-R185; J. Sanchez-Romero & V. De Lorenzo, Genetic Engineering of Nonpathogenic *Pseudomonas* strains as Biocatalysts for Industrial and Environmental Processes, in Manual of Industrial Microbiology and Biotechnology (A. Demain & J. Davies, eds.) pp. 460-74 (1999) (ASM Press, Washington, D.C.); H. Schweizer, Vectors to express foreign genes and techniques to monitor gene expression for Pseudomonads, Current Opinion in Biotechnology, 12:439-445 (2001); and R. Slater & R. Williams, The Expression of Foreign DNA in Bacteria, in Molecular Biology and Biotechnology (J. Walker & R. Rapley, eds.) pp. 125-54 (2000) (The Royal Society of Chemistry, Cambridge, UK). Several problems exist with these types of promoters. For example: high temperature induction may be harmful to cells, and may not be practical for large scale fermentation due to equipment limitations; oxygen manipulation may affect the overall dynamics of the cell growth density aspects of the fermentation, reducing ideal conditions; the use of toluenes or other similar types of potentially toxic chemicals may require further purification to ensure that these compounds are not present in the final product; and pH may affect the ability of the peptide of interest to correctly fold or be solubilized in the host, making purification more costly and difficult.

Promoters that can be induced by inexpensive and non-toxic carbon sources remain attractive for use in bacterial fermentation processes. One potential advantage to such a promoter is that bacterial host may have endogenous mechanisms to efficiently uptake the inducer. Potential carbon sources that can be used as inducers include maltose, maltodextrin, glucose, arabinose, fructose, galactose, sucrose, glycerol, mannose, acetate, and lactose. Other potential carbon source inducers include the alcohol forms of carbon sugars, such as mannitol, glucitol, and arabitol.

Mannitol as Potential Inducer

Mannitol is the alcohol form of mannose, and is an inexpensive carbon source for a number of bacteria, including Pseudomonads. The operon involved with uptake and degradation of mannitol in *Pseudomonas fluorescens* (*P. fluorescens*) contains seven genes, four of which (mtlEFGK) encode proteins involved in mannitol/glucitol/arabitol uptake and transport, and three of which (mtlDYZ) encode proteins involved in the catabolism of mannitol, glucitol, and arabitol. See Brunker et al. (1998) "Structure and function of the genes involved in mannitol, arabitol, and glucitol utilization from *Pseudomonas fluorescens* DSM50106," Gene 206(1):117-126 and FIG. 1.

Brunker et al. have further identified a sequence similar to the consensus for *E. coli* sigma 70 promoters 90 bp upstream from the start codon of the first gene in the *P. fluorescens* DSM50106 operon, mtlE. See FIG. 2. A 660 bp fragment containing the putative promoter was cloned upstream of a luciferase gene upon which it conferred mannitol-inducible expression. Arabitol induced expression of the gene to the same level, and glucitol induced expression to a level half as high.

The benefit of carbon source inducible promoters, however, is not without its limitations. One potential problem associated with utilizing carbon source inducible promoters is the ability of the host cell to metabolize the inducer and reduce the effectiveness of the inducer, or require it to be continually added to the media during induction. In addition, the inducer may compromise carbon utilization parameters of the fermentation process, and the constant inducer flux may result in less than desirable peptide production yields. The requirement of continually adding an inducer to the media during induction has the further disadvantage of increasing the cost of the fermentation process.

SUMMARY OF THE INVENTION

The present invention provides bacterial cells and methods for producing recombinant peptides in a bacterial host utilizing a mannitol, glucitol, or arabitol-inducible promoter operably attached to a nucleic acid encoding a target polypeptide, wherein the bacterial host cell has been rendered incapable of degrading or metabolizing mannitol, glucitol, or arabitol. Because the bacterial cell lacks the ability to metabolize or degrade a carbon source selected from the group consisting of mannitol, glucitol, arabitol, and derivatives or analogues thereof, these carbon sources can be utilized to induce expression of a polypeptide, wherein the nucleic acid encoding the polypeptide is operably attached to a mannitol, glucitol, or arabitol-inducible promoter, without the inducer being continuously removed from the media by the host cell. The inducer, therefore, is capable of providing continuous and stable induction levels during fermentation without the requirement of adding additional inducer to the media.

In some embodiments a bacterial cell is provided that comprises a nucleic acid construct including a mannitol, arabitol, or glucitol-inducible promoter operably linked to a nucleic acid sequence encoding a peptide of interest. Alternatively, one embodiment includes the bacterial cell comprising a nucleic acid construct or constructs including more than one mannitol, arabitol, or glucitol-inducible promoter operably linked to the same, or different, peptide or peptides of interest. In additional embodiments at least one of the promoters is a mannitol-inducible promoter, and the bacterial cell expressing the recombinant peptide of interest has been genetically manipulated to inhibit degradation or metabolism of mannitol. Alternatively, the promoter is capable of induction by glycerol, as well as mannitol, and the bacterial cell expressing the recombinant peptide of interest has been genetically manipulated to inhibit degradation or metabolism of mannitol.

The promoter utilized in the present invention is capable of induction by a carbon source sugar, alcohol, or derivatives thereof. Typically, the promoter can be induced by mannitol, arabitol, or glucitol. Alternatively, the promoter can also be induced by glycerol. In some embodiments the promoter can be a mannitol inducible promoter. In other embodiments the promoter can include the putative promoter of an endogenous bacterial mannitol operon, and is induced by mannitol derivatives or analogues thereof. In other embodiments the mannitol promoter is capable of being induced by a carbon source selected from the group consisting of mannitol, glucitol, arabitol, glycerol, or derivatives or analogues thereof.

In additional embodiments the promoter can include the putative promoter of the *Pseudomonas fluorescens* mtlEFGKDYZ operon. In yet further embodiments the promoter can further include a nucleic acid sequence that acts as an mtl activator protein (MtlR) binding region. In some embodiments, the nucleic acid sequence of the promoter is selected from the group consisting of SEQ ID NOS:1-13. In one embodiment, the nucleic acid sequence of the promoter comprises SEQ ID NO:9 or SEQ ID NO: 12. In one embodiment, the nucleic acid sequence comprises a range of at least 299 continuous nucleotides upstream of the *Pseudomonas fluorescens* MB101 mtlE gene. In additional embodiments, the promoter is a nucleotide sequence having at least 90% sequence identity to the nucleotide sequence of the putative promoter of the *Pseudomonas fluorescens* mtlEFGKDYZ operon. Additional embodiments include wherein the promoter is the nucleic acid sequence having at least 90% sequence identity to the nucleotide sequence selected from the group consisting of SEQ ID NOS:1-13. In one embodiment, the promoter is the nucleic acid sequence having at least 90% sequence identity to the nucleotide sequence selected from the group consisting of SEQ ID NOS:9 and 12. In one embodiment, the promoter is a nucleotide sequence that hybridizes to a nucleotide sequence selected from the group consisting of SEQ ID NOS:1-13, or a nucleic acid sequence that hybridizes to a nucleotide sequence having at least 90% sequence identity to the nucleotide sequence selected from the group consisting of SEQ ID NOS:1-13. In one embodiment, the promoter is a nucleotide sequence that hybridizes to a nucleic acid sequence selected from SEQ ID NOS:9 or 12, or a nucleotide sequence that hybridizes to a nucleotide sequence having at least 90% sequence identity to the nucleotide sequence selected from the group consisting of SEQ ID NOS:9 and 12. In certain embodiments, the hybridization is under conditions of high stringency.

Embodiments of the present invention also include bacterial cells that have been rendered incapable of metabolizing or degrading a carbon source as expression systems for recombinant peptides of interest. This carbon source can be selected from the group consisting of mannitol, glucitol, arabitol, and derivative or analogue thereof. In some embodiments the mutation is a result of exogenous genetic manipulation through the mutation or the deletion of at least one gene encoding an enzyme required for the metabolism or degradation of the carbon source used as an inducer. In other embodiments the mutated or deleted gene(s) is a gene(s) encoding for an enzyme(s) required in the metabolism or degradation of mannitol, arabitol, or glucitol, or derivative or analogue thereof. In another embodiment, the mutated or deleted gene(s) is a gene(s) required in the metabolism of mannitol, or derivatives or analogues thereof. In further embodiments the gene is selected from the mtl operon. For example, the mutated or deleted gene can be selected from the group consisting of mtlD, mtlY, and mtlZ. In an alternative embodiment, the mutation or deletion includes a combination of at least two of mtlD, mtlY, mtlZ (mtlDYZ). In one embodiment, the cell includes a mutation or deletion of at least mtlD. In additional embodiments, the cell includes a mutation or deletion in each of mtlD, mtlY, and mtlZ (mtlDYZ).

In some embodiments a bacterial cell or expression system is selected from any bacterial cell capable of expressing a nucleic acid operably linked to the carbon source inducible promoter. In one embodiment the bacterial cell is selected from the Pseudomonads and closely related bacteria. In one embodiment the bacterial cell is a *Pseudomonas*. In certain embodiments, the bacterial cell is *Pseudomonas fluorescens*. In other embodiments, the bacterial cell is *Escherichia coli*.

Embodiments of the present invention also provide methods for producing recombinant peptides in bacterial host cells utilizing a carbon source inducible promoter. Additional embodiments provide alternative promoters for use in large scale bacterial fermentation processes that are induced by low cost carbon source chemicals. Other embodiments of the present invention provide for improved bacterial host cells for the expression of recombinant proteins from promoters induced by a carbon source.

The present invention further provides methods for producing recombinant peptides comprising providing a bacterial cell that has been rendered incapable of degrading or metabolizing mannitol, glucitol, or arabitol, or derivative thereof, transforming the cell with at least one nucleic acid construct comprising at least one nucleic acid encoding at least one peptide of interest operably attached to at least one carbon source-inducible promoter, wherein the inducer is selected from the group consisting of mannitol, glucitol, arabitol, glycerol, or derivative or analogue thereof, and growing the cell under conditions to promote peptide expression. In certain embodiments, the expression of the peptide of interest is controlled in a linear fashion directly correlated to the inducer concentration. In some embodiments at least one promoter is a mannitol-inducible promoter and the inducer is glycerol or derivatives or analogues thereof. In some embodiments at least one promoter is a mannitol-inducible promoter, wherein the bacterial cell has been rendered incapable of metabolizing or degrading mannitol, and the inducer is mannitol arabitol, glucitol, glycerol, or derivatives or analogues thereof.

In other embodiments, the present invention provides the expression of a nucleic acid encoding a peptide operably attached to a promoter induced by mannitol, glucitol, arabitol, or glycerol, or analogue thereof, in combination with other inducible promoters in a bacterial cell that has been rendered deficient in its ability to degrade or metabolize mannitol, glucitol, arabitol, or analogues or derivatives thereof. In other embodiments, the additional inducible promoters can be operably linked in tandem to the mannitol, glucitol, or arabitol-inducible promoter. In other embodiments, the promoters are independent of each other and operably linked to separate nucleic acids encoding peptides of interest. Additional embodiments of the present invention include the use of multiple promoters, including at least one mannitol, glucitol, or arabitol-inducible promoter, wherein the promoters are independent of each other and operably attached to nucleic acids encoding different peptides of interest. In these embodiments, the promoters can be differentially induced, either at different times, or at different expression levels controlled by, for example, the utilization of inducer concentration gradients.

BRIEF DESCRIPTION OF THE FIGURES

FIG. 4 illustrates a comparison of the genomic region upstream of mtlE in various Pseudomonads. The region upstream of the mtlE gene in MB11 (SEQ ID NO:32), DSM50106 (SEQ ID NO:31), *P. fluorescens* Pf0-1 (SEQ ID NO:33), and *P. aeruginosa* PA0-1 (SEQ ID NO:34) was aligned. Regions of perfect homology among the four strains are indicated by small case font. The −35 and −10 regions, putative ribosome binding site (RBS) and start codon are underlined. The dotted-line box shows the minimal sequence required for mannitol induction.

DETAILED DESCRIPTION

Figure 1:
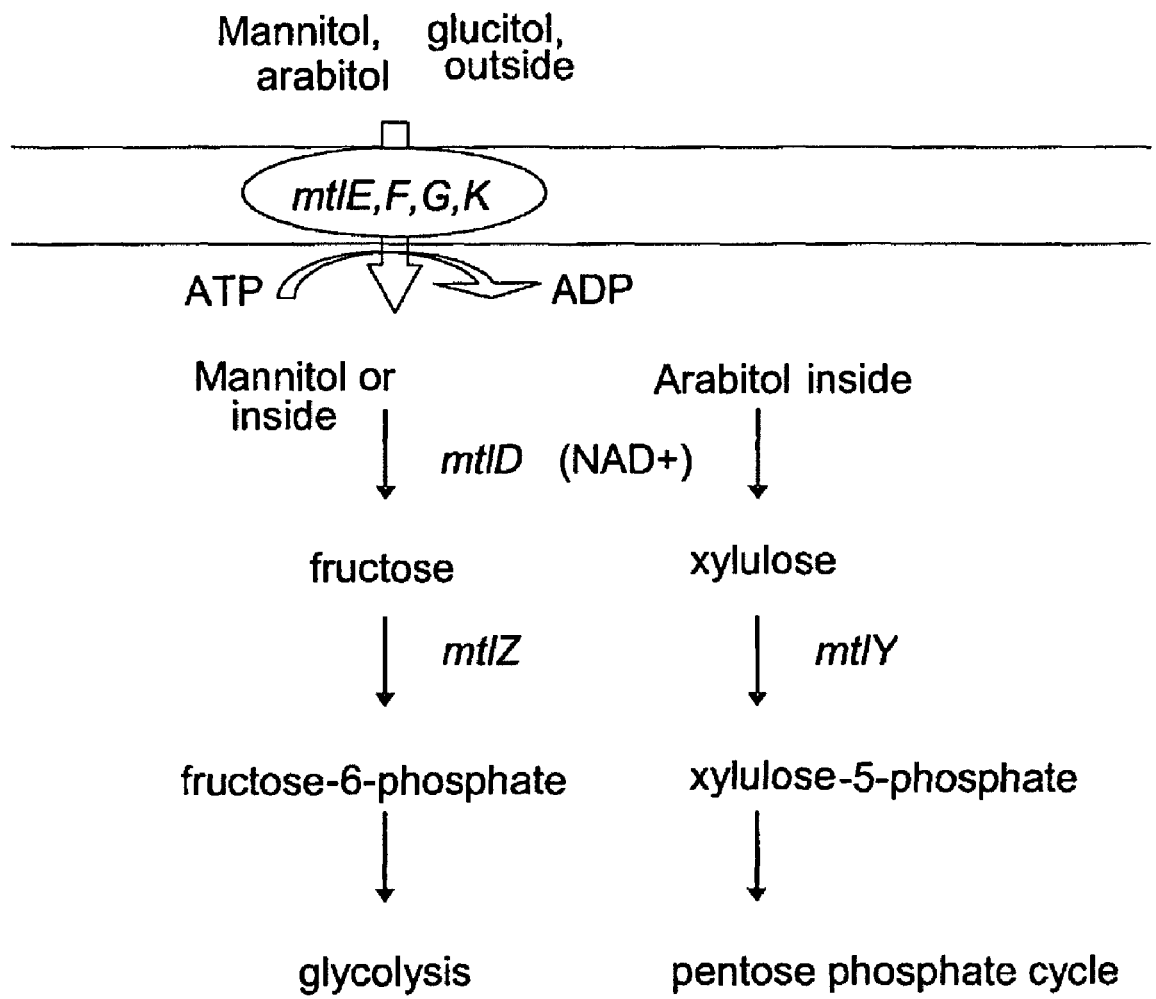
FIG. 1 illustrates a pathway of mannitol, glucitol, and arabitol degradation, as described by Brunker et al. (1998) "Structure and function of the genes involved in mannitol, arabitol, and glucitol utilization from *Pseudomonas fluorescens* DSM50106," Gene 206(1): 117-126.
Figure 2:
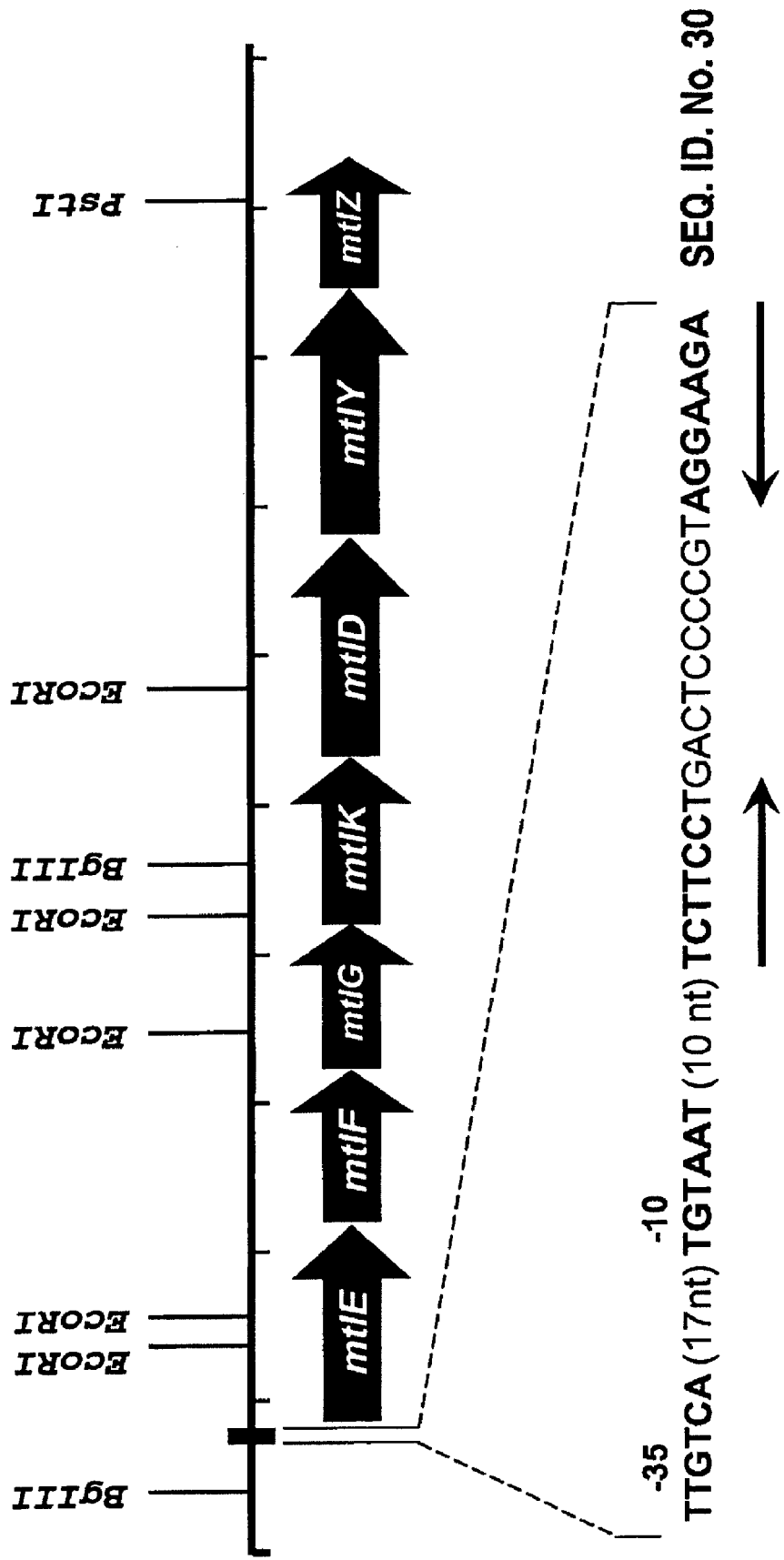
FIG. 2 illustrates the structure of the *P. fluorescens* mannitol (mtl) operon (SEQ ID NO:30) in DSM50106, identifying putative −10 and −35 sites in the promoter (bold) and a region of inverted homology (arrows), as described by Brunker et al. (1998) "Structure and function of the genes involved in mannitol, arabitol, and glucitol utilization from *Pseudomonas fluorescens* DSM50106," Gene 206(1): 117-126. The mtlR activator is present at a site distant from the mtl operon.

The present invention provides methods for producing recombinant peptides in a bacterial host utilizing a mannitol, arabitol, glucitol, or glycerol-inducible promoter, wherein the host bacterial cell that produces the peptide has been rendered incapable of degrading or metabolizing mannitol, arabitol, or glucitol, or derivatives or analogues thereof. The present invention provides bacterial cells that have been genetically altered to inhibit the metabolism or degradation of mannitol, glucitol, or arabitol, or derivatives or analogues thereof. In certain embodiments, mannitol, arabitol, glucitol, or glycerol can then be used to induce expression of a target polypeptide from an inducible promoter, allowing for the use of an inexpensive and stable carbon source inducer in the fermentation processes for the production of recombinant peptides. Because the bacterial cell lacks the ability to metabolize or degrade mannitol, glucitol, or arabitol, if these carbon sources are used as an inducer, then the inducer is not continuously removed from the media by the host cell, and therefore is capable of providing continuous and stable induction levels during fermentation without the requirement of adding additional inducer to the media. In some embodiments the bacterial cell is rendered incapable of degrading or metabolizing mannitol, glucitol, or arabitol, or derivatives or analogues thereof, and the promoter operably linked to a peptide of interest is capable of induction by glycerol, as well as mannitol, glucitol, or arabitol, or derivatives or analogues thereof.

I. Mannitol Inducible Promoters

The promoters for use in the present invention are nucleic acid sequences typically of greater than 25 nucleic acids located upstream of the nucleic acid sequence encoding a peptide of interest. The promoters generally contain a −35 region, which is generally a 5-6 nucleic acid sequence beginning approximately 35 base pairs upstream of the transcription start site for a peptide or interest. The transcription start site of the peptide of interest is generally numbered as +1.

In the present invention, an inducible promoter is utilized that is capable of induction by a carbon source. In some embodiments the promoter is capable of induction by a carbon source selected from the group consisting of mannitol, arabitol, glucitol, and glycerol, or derivatives or analogues thereof. In other embodiments the promoter is a mannitol, or mannitol derivative, inducible promoter. In additional embodiments the promoter is the putative promoter of an endogenous bacterial mannitol operon. In some embodiments the promoter is the putative promoter, and related regulatory regions, of the *Pseudomonas fluorescens* mtlEFGKDYZ operon. In other embodiments of the present invention the mannitol-inducible promoter is capable of being induced by a carbon source other than mannitol. Such carbon sources include, but are not limited to glucitol, arabitol, and glycerol. In some embodiments the carbon source is glycerol.

In some embodiments the mannitol inducible promoter of the present invention comprises the −35 region of the Pseudomonad native mtl operon promoter attached upstream of the −10 region of the native promoter, via a 15-20 nucleotide linker. In other embodiments the linker is 17-18 nucleotides long. In another embodiment, the −35 region is comprised of the nucleic acid sequence 5'-TTGTCA-3'. In yet another embodiment, the −10 region is comprised of the nucleic acid sequence 5'-TGTAAT-3'. In still another embodiment, the promoter is comprised of the −35 region 5'-TTTGTC-3', linked to a nucleotide sequence of between 15-20 nucleotides, which is further linked to the −10 region 5'-TGTAAT-3'.

In alternative embodiments the mannitol-inducible promoter includes the nucleotide sequence comprising 5'-TTGT-CACAACCCCGTTTGAAGGCTGTAAT-3' (SEQ ID NO:1) (Table 1). In another embodiment, the promoter includes the nucleotide sequence comprising 5'-TTGTCACCGC-CGTTTTTGAAGGCTGTAAT-3' (SEQ ID NO:2) (Table 1). In still another embodiment, the promoter includes the nucleotide sequence comprising 5'-TTGTCAGCCCTGCGTCA-GAAGGCTGTAAT-3' SEQ ID NO:3 (Table 1). In still another embodiment, the promoter includes the nucleic acid sequence 5'-TTGTCGGTTGCGTGACGCGCCTGTGTAA-3' (SEQ ID NO:4) (Table 1).

In some embodiments the mannitol-inducible promoter of the present invention further includes nucleic acid sequences that act as an activator or repressor peptide binding site. In some embodiments the nucleic acid sequences act as an activator peptide binding site. In other embodiments the activator site is a nucleic acid sequence from an endogenous Pseudomonad MtlR protein binding site. In other embodiments the activator site is a nucleic acid sequence from an endogenous *Pseudomonas fluorescens* MtlR protein binding site.

In some embodiments the activator binding site includes the nucleic acid sequence 5'-ACGAGTGCAAAAAAGTAT-CAGTAAGCGTGCTCCCAAGGAT-3' (SEQ ID NO:5) (Table 2). In another embodiment, the activator binding site includes the nucleic acid sequence 5'-ACGAGTG-CAAAAAAGTATCAGTCCAAGTGCTCCCAAG GAT-3' (SEQ ID NO:6) (Table 2). Alternatively, the activator binding site includes the nucleic acid sequence 5'-CCGAGTG-CAAAAAAGTATCGATTCAAGTGCTA GGGATGAT-3' (SEQ ID NO:7) (Table 2). In another embodiment, the activator binding site includes 5'-GGCGGTGCAAAAAAG-TATCGGTCGAAGTGCAG TCGAGGCT-3' (SEQ ID NO:8) (Table 2).

In additional embodiments the mannitol inducible promoter of the present invention includes SEQ ID NO:9, a 299 base pair region of an endogenous Pseudomonad mtl operon (Table 3). In another embodiment, the mannitol promoter of the present invention includes SEQ ID NO:10, a 203 base pair region of an endogenous Pseudomonad mtl operon (Table 3). In yet another embodiment, the promoter of the present invention includes SEQ ID NO: 111, a 126 base pair region from an endogenous Pseudomonad mtl operon (Table 3). In another embodiment, the promoter of the present invention includes SEQ ID NO: 12, a 147 base pair region from an endogenous Pseudomonad mtl operon (Table 3). In additional embodiments the promoter of the present invention includes SEQ ID NO: 13, a 77 base pair region from an endogenous Pseudomonad mtl operon (Table 3)

TABLE 1

Mannitol Inducible Promoter −35 to −10 Nucleic Acid Regions

| | |
|---|---|
| 5'-TTGTCACAACCCCGTTTGAAGGCTGTAAT-3' | SEQ ID NO: 1 |
| 5'-TTGTCACCGCCGTTTTTGAAGGCTGTAAT-3' | SEQ ID NO: 2 |
| 5'-TTGTCAGCCCTGCGTCAGAAGGCTGTAAT-3' | SEQ ID NO: 3 |
| 5'-TTGTCGGTTGCGTGACGCGCCTGTGTAA-3' | SEQ ID NO: 4 |

TABLE 2

Mannitol Inducible Promoter Activator Nucleic Acid Regions

| | |
|---|---|
| 5'-ACGAGTGCAAAAAAGTATCAGTAAGCGTGCTCCCAAGGAT-3' | SEQ ID NO: 5 |
| 5'-ACGAGTGCAAAAAAGTATCAGTCCAAGTGCTCCCAAGGAT-3' | SEQ ID NO: 6 |
| 5'-CCGAGTGCAAAAAAGTATCGATTCAAGTGCTAGGGATGAT-3' | SEQ ID NO: 7 |

TABLE 2-continued

Mannitol Inducible Promoter Activator Nucleic Acid Regions

SEQ ID NO: 8
5'-GGCGGTGCAAAAAAGTATCGGTCGAAGTGCAGTCGAGGCT-3'

TABLE 3

Mannitol Inducible Promoters mtl Operon Nucleic Acid Regions

GAGCGTGGGAACGATCAAGTGTTAAACACTGCACTG SEQ ID NO: 9
AGGATCGTTCCCGCGCTCCGCGTGGGCATGCATACC
GTGACGCTCTGCGTCACCTGGGGACGCAGAGCGTCC
CTAGCGGCGTTACCACGCGGAGCGTGGGAACGATCA
GGTGGTCGACGAGTGCAAAAAAGTATCAGTAAGCGT
GCTCCCAAGGATTTGTCACCGCCGTTTTTGAAGGCT
GTAATCAACGCACACTCTTCCTGACTCCTTGTAGGA
AGACACAACAACAATAACCGTCCTTCTGTAGCCCTC
TGGGCGCGGAA

TGAGCAGGAAAATCTGTACGGTTTCGCGCCCTTCGC SEQ ID NO: 10
CATGCTGAAACGCCCTTCCCTGCGGTTATCGCGCCA
ATCCCGAGTGCAAAAAAGTATCGATTCAAGTGCTAG
GGATGATTTGTCAGCCCTGCGTCAGAAGGCTGTAAT
CAGTGCACATTCTTCCCCCGCCGGAAGAACACAAAA
ACAATAACTGTCCTTCTGCCCCC

TAAGCGTGCTCCCAAGGATTTGTCACCGCCGTTTTT SEQ ID NO: 11
GAAGGCTGTAATCAACGCACACTCTTCCTGACTCCT
TGTAGGAAGACACAACAACAATAACCGTCCTTCTGT
AGCCCTCTGGGCGCGGAA

ACGAGTGCAAAAAAGTATCAGTAAGCGTGCTCCCAA SEQ ID NO: 12
GGATTTGTCACCGCCGTTTTTGAAGGCTGTAATCAA
CGCACACTCTTCCTGACTCCTTGTAGGAAGACACAA
CAACAATAACCGTCCTTCTGTAGCCCTCTGGGCGCG
GAA

ACGAGTGCAAAAAAGTATCAGTAAGCGTGCTCCCAA SEQ ID NO: 13
GGATTTGTCACCGCCGTTTTTGAAGGCTGTAATCAA
CGCAC

Additional embodiments include wherein the promoter is the nucleic acid sequence having at least 90% sequence identity to the nucleotide sequence selected from the group consisting of SEQ ID NOS:1-13. In one embodiment, the promoter is the nucleic acid sequence having at least 90% sequence identity to the nucleotide sequence selected from the group consisting of SEQ ID NOS:9 and 12.

In one embodiment, the promoter is a nucleotide sequence that hybridizes, under conditions of high stringency, to a nucleotide sequence selected from the group consisting of SEQ ID NOS:1-13, or a nucleic acid sequence that hybridizes, under conditions of high stringency, to a nucleotide sequence having at least 90% sequence identity to the nucleotide sequence selected from the group consisting of SEQ ID NOS:1-13. In one embodiment, the promoter is a nucleotide sequence that hybridizes, under conditions of high stringency, to a nucleic acid sequence selected from SEQ ID NOS:9 or 12, or a nucleotide sequence that hybridizes, under conditions of high stringency, to a nucleotide sequence having at least 90% sequence identity to the nucleotide sequence selected from the group consisting of SEQ ID NOS:9 and 12.

The sequences recited in this application may be homologous (have similar identity). Nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more changes in nucleic acid sequence. Homology is generally inferred from sequence similarity between two or more nucleic acids (or sequences thereof). The precise percentage of similarity between sequences that is useful in establishing homology varies with the nucleic acid at issue, but as little as 25% sequence similarity is routinely used to establish homology. Higher levels of sequence similarity, e.g., 30%, 40%, 50%, 60%, 70%, 80%, 90%, 95%, 96%, 97%, 98% or 99% or more can also be used to establish homology. Methods for determining sequence similarity percentages (e.g., BLASTN using default parameters) are described herein and are generally available.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345 358; Hein J. (1990) Unified Approach to Alignment and Phylogenes pp. 626 645 Methods in Enzymology vol. 183, Academic Press, Inc., San Diego, Calif.; Higgins, D. G. and Sharp, P. M. (1989) CABIOS 5:151 153; Myers, E. W. and Muller W. (1988) CABIOS 4:11 17; Robinson, E. D. (1971) Comb. Theor 11: 105; Santou, N. Nes, M. (1987) Mol. Biol. Evol. 4:406 425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) *Proc. Natl. Acad., Sci. USA* 80:726 730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One example of algorithms that can be suitable for determining percent sequence identity and sequence similarity are the BLAST and BLAST 2.0 algorithms, which are described in Altschul et al. (1977) *Nucl. Acids Res.* 25:3389 3402 and Altschul et al. (1990) *J. Mol. Biol.* 215:403 410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

II. Host Cells

The present invention also provides bacterial cells that have been genetically modified to reduce their ability to metabolize or degrade a carbon source selected from the group consisting of mannitol, glucitol, arabitol, and derivative or analogue thereof, which carbon source can be utilized to induce expression from an inducible promoter. The genetic modification can be to a gene or genes encoding an enzyme that is operative in a metabolic pathway involved in metabolizing or degrading a carbon source selected from the group consisting of mannitol, glucitol, arabitol, and derivatives or analogues thereof utilized to induce expression from the inducible promoter. Preferably, the host cell has genetic modifications to genes encoding enzymatic activity related to the metabolization or degradation of the inducer, while genes related to the transport of the inducer are unaffected, allowing for transport into the cell without subsequent degradation or metabolization. In some embodiments the bacterial cell is an *E. coli* cell. In some embodiments the bacterial cell is selected from Pseudomonads and closely related cells. In some embodiments the bacterial cell is a *Pseudomonas fluorescens* cell.

A bacterial host cell selected for use in the present invention can be rendered deficient in its ability to metabolize or degrade any inducer utilized to induce expression of a peptide of interest from an inducible promoter. For example, where mannitol is selected as the inducer, the host cell can be rendered deficient in it ability to express an enzyme required for metabolizing mannitol, or any effective replacement enzyme capable of metabolizing mannitol. In some embodiments the host cell will be made deficient for the metabolization or degradation of the inducer by altering its genome so that the cell cannot express, from its genome, a functional enzyme involved in the metabolization or degradation of the inducer. This alteration can be done by altering the cell's genomic coding sequence of the gene encoding the metabolizing or degrading enzyme or enzymes. In other embodiments the coding sequence alteration will be accomplished by introducing: insertion or deletion mutations that change the coding sequence reading frame; substitutions or inversion mutations that alter a sufficient number of codons; and/or deletion mutations that delete a sufficiently large group of contiguous codons therefrom capable of producing a non-functional enzyme.

Such knock-out strains can be prepared according to any of the various methods known in the art as effective. For example, homologous recombination vectors containing homologous targeted gene sequences 5' and 3' of the desired nucleic acid deletion sequence can be transformed into the host cell. Ideally, upon homologous recombination, a desired targeted enzymatic gene knock-out can be produced.

Specific examples of gene knock-out methodologies are well known in the art. For example, gene inactivation by insertion of a polynucleotide has been previously described. See, e.g., D L Roeder & A Collmer, *Marker-exchange mutagenesis of a pectate lyase isozyme gene in Erwinia chrysanthemi*, J. Bacteriol. 164(1):51-56 (1985). Alternatively, transposon mutagenesis and selection for desired phenotype (such as the inability to metabolize a particular carbon source) can be used to isolate bacterial strains in which target genes have been insertionally inactivated. See, e.g., K Nida & P P Cleary, *Insertional inactivation of streptolysin S expression in Streptococcus pyogenes*, J. Bacteriol. 155(3):1156-61 (1983). Specific mutations or deletions in a gene can be constructed using cassette mutagenesis, for example, as described in J A Wells et al., *Cassette mutagenesis: an efficient method for generation of multiple mutations at defined sites*, Gene 34(2-3):315-23 (1985); whereby direct or random mutations are made in a selected portion of a gene, and then incorporated into the chromosomal copy of the gene by homologous recombination.

In additional embodiments of the present invention the bacterial cell is rendered deficient in an enzyme necessary to metabolize the carbon source used as an inducer for recombinant peptide expression. In some embodiments the bacterial cell is rendered deficient in an enzyme necessary to metabolize the carbon source mannitol, glucitol, arabitol, or derivatives thereof. In some embodiments the bacterial cell is constructed to lack enzyme activity encoded by a gene from an endogenous mannitol operon—mtl. In another embodiment, the bacterial cell is constructed to lack enzyme activity encoded by the endogenous mtlD gene, or homologue thereof. In an alternative embodiment, the bacterial cell is constructed to lack enzyme activity encoded by an endogenous mtlY gene, or homologue thereof. In still another embodiment, the bacterial cell is constructed to lack enzyme activity encoded by an endogenous mtlZ gene, or homologue thereof. Alternatively, the bacterial cell can be constructed to lack activity of any combination of enzymes encoded by the mtlDYZ genes, or homologues thereof. In additional embodiments the bacterial cell is constructed to lack enzyme activity encoded by an endogenous mtlD, mtlY, and mtlZ genes.

In an alternative embodiment, the bacterial cell can be a natural mutant, wherein the mutant is incapable of degrading or metabolizing a carbon source used as an inducer for recombinant peptide expression due to a naturally arising mutation in an endogenous gene necessary for such carbon source degradation of metabolization.

In addition, the present invention further provides bacterial cells comprising a nucleic acid construct including a nucleic acid sequence encoding for at least one peptide of interest operably linked to at least one carbon source-inducible promoter, wherein the carbon source inducible promoter is a mannitol, arabitol, or glucitol-inducible promoter. In some embodiments the carbon source-inducible promoter is a mannitol-inducible promoter. In other embodiments the mannitol-inducible promoter is capable of being induced by glycerol.

Alternatively, the bacterial cell comprises a first nucleic acid construct including a nucleic acid sequence encoding for at least one peptide of interest operably linked to at least one carbon source-inducible promoter, and a second nucleic acid construct including a nucleic acid sequence encoding at least one peptide of interest operably linked to at least one inducible promoter. In some embodiments the carbon-source inducible promoter is a mannitol, glucitol, or arabitol-inducible promoter. The multiple promoters can be located on the same nucleic acid constructs, or on separate nucleic acid constructs. During the fermentation process, expression of the peptides of interest can be induced in a differential manner, including at different times or at different expression levels. In certain embodiments, the inducible promoters (and related inducers) used in combination with the mannitol-, arabitol, or glucitol-inducible promoters of the present invention can include, for example, lac (IPTG), lacUV5 (IPTG), tac (IPTG), trc (IPTG), $P_{syn}$ (IPTG), trp (tryptophan starvation), araBAD (1-arabinose), lpp$^a$ (IPTG), lpp-lac (IPTG), phoA (phosphate starvation), recA (nalidixic acid), proU (osmolarity), cst-1 (glucose starvation), tetA (tretracylin), cadA (pH), nar (anaerobic conditions), PL (thermal shift to 42° C.), cspA (thermal shift to 20° C.), T7 (thermal induction), T7-lac operator (IPTG), T3-lac operator (IPTG), T5-lac operator (IPTG), T4 gene32 (T4 infection), nprM-lac operator (IPTG), Pm (alkyl- or halo-benzoates), Pu (alkyl- or halo-toluenes), Psal (salicylates), ant (anthranilate), ben (benzoate) or VHb (oxygen) promoter. See, for example, Makrides, S. C. (1996) Microbiol. Rev. 60, 512-538; Hannig G. & Makrides, S. C. (1998) TIBTECH 16, 54-60; Stevens, R. C. (2000) Structures 8, R177-R185. See, e.g.: J. Sanchez-Romero & V. De Lorenzo, Genetic Engineering of Nonpathogenic *Pseudomonas* strains as Biocatalysts for Industrial and Environmental Processes, in Manual of Industrial Microbiology and Biotechnology (A. Demain & J. Davies, eds.) pp. 460-74 (1999) (ASM Press, Washington, D.C.); H. Schweizer, Vectors to express foreign genes and techniques to monitor gene expression for Pseudomonads, Current Opinion in Biotechnology, 12:439-445 (2001); and R. Slater & R. Williams, The Expression of Foreign DNA in Bacteria, in Molecular Biology and Biotechnology (J. Walker & R. Rapley, eds.) pp. 125-54 (2000) (The Royal Society of Chemistry, Cambridge, UK).

The nucleic acid constructs contained in the bacterial cell may be maintained in an episomal fashion, or be integrated into the genome of the cell.

Bacterial Organisms

The present invention provides bacterial cells that are deficient in an enzyme necessary for metabolism of a carbon source selected from the group consisting of mannitol, glucitol, and arabitol, or derivative or analogue thereof, which carbon source is utilized to induce expression of a peptide of interest, wherein the nucleic acid sequence encoding the peptide of interest is operably attached to a promoter induced by a carbon source, the carbon source selected from the group consisting of mannitol, glucitol, arabitol, and derivative or analogue thereof. The present invention contemplates utilizing any bacterial cell capable of expressing a recombinant peptide. Such cells are well known in the art. In some embodiments the host cell can be a *Escherichia coli* cell. In another embodiment, the cell is selected from a Pseudomonad or closely related cell. In other embodiments the bacterial cell is a *Pseudomonas fluorescens*. In some embodiments the bacterial cell can be deficient in an enzyme necessary for the metabolism of a carbon source selected from the group consisting of mannitol, glucitol, or arabitol, or derivatives and analogues thereof.

Pseudomonads and closely related bacteria, as used herein, is co-extensive with the group defined herein as "Gram(−) Proteobacteria Subgroup 1." "Gram(−) Proteobacteria Subgroup 1" is more specifically defined as the group of Proteobacteria belonging to the families and/or genera described as falling within that taxonomic "Part" named "Gram-Negative Aerobic Rods and Cocci" by R. E. Buchanan and N. E. Gibbons (eds.), Bergey's Manual of Determinative Bacteriology, pp. 217-289 (8th ed., 1974) (The Williams & Wilkins Co., Baltimore, Md., USA) (hereinafter "Bergey (1974)"). Table 4 presents the families and genera of organisms listed in this taxonomic "Part."

TABLE 4

FAMILIES AND GENERA LISTED IN THE PART, "GRAM-NEGATIVE AEROBIC RODS AND COCCI" (IN BERGEY (1974))

| | |
|---|---|
| Family I. Pseudomonadaceae | Gluconobacter |
| | Pseudomonas |
| | Xanthomonas |
| | Zoogloea |
| Family II. Azotobacteraceae | Azomonas |
| | Azotobacter |
| | Beijerinckia |
| | Derxia |
| Family III. Rhizobiaceae | Agrobacterium |
| | Rhizobium |
| Family IV. Methylomonadaceae | Methylococcus |
| | Methylomonas |
| Other Genera | Acetobacter |
| | Alcaligenes |
| | Bordetella |
| | Brucella |
| | Francisella |
| | Thermus |

"Gram(−) Proteobacteria Subgroup 1" contains all Proteobacteria classified there under, as well as all Proteobacteria that would be classified according to the criteria used in forming that taxonomic "Part." As a result, "Gram(−) Proteobacteria Subgroup 1" excludes, e.g.: all Gram-positive bacteria; those Gram-negative bacteria, such as the Enterobacteriaceae, which fall under others of the 19 "Parts" of this Bergey (1974) taxonomy; the entire "Family V. Halobacteriaceae" of this Bergey (1974) "Part," which family has since been recognized as being a non-bacterial family of Archaea; and the genus, *Thermus*, listed within this Bergey (1974) "Part," which genus which has since been recognized as being a non-Proteobacterial genus of bacteria.

"Gram(−) Proteobacteria Subgroup 1" further includes those Proteobacteria belonging to (and previously called species of) the genera and families defined in this Bergey (1974) "Part," and which have since been given other Proteobacterial taxonomic names. In some cases, these re-namings resulted in the creation of entirely new Proteobacterial genera. For example, the genera *Acidovorax, Brevundimonas, Burkholderia, Hydrogenophaga, Oceanimonas, Ralstonia*, and *Stenotrophomonas*, were created by regrouping organisms belonging to (and previously called species of) the genus *Pseudomonas* as defined in Bergey (1974). Likewise, e.g., the genus *Sphingomonas* (and the genus *Blastomonas*, derived therefrom) was created by regrouping organisms belonging to (and previously called species of) the genus *Xanthomonas* as defined in Bergey (1974). Similarly, e.g., the genus *Acidomonas* was created by regrouping organisms belonging to (and previously called species of) the genus *Acetobacter* as defined in Bergey (1974). Such subsequently reassigned species are also included within "Gram(−) Proteobacteria Subgroup 1" as defined herein.

In other cases, Proteobacterial species falling within the genera and families defined in this Bergey (1974) "Part" were simply reclassified under other, existing genera of Proteobacteria. For example, in the case of the genus *Pseudomonas*, *Pseudomonas enalia* (ATCC 14393), *Pseudomonas nigrifaciens* (ATCC 19375), and *Pseudomonas putrefaciens* (ATCC 8071) have since been reclassified respectively as *Alteromonas haloplanktis*, *Alteromonas nigrifaciens*, and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have since been reclassified respectively as *Pseudoalteromonas nigrifaciens* and *Pseudoalteromonas piscicida*. Such subsequently reassigned Proteobacterial species are also included within "Gram(−) Proteobacteria Subgroup 1" as defined herein.

"Gram(−) Proteobacteria Subgroup 1" also includes Proteobacterial species that have since been discovered, or that have since been reclassified as belonging, within the Proteobacterial families and/or genera of this Bergey (1974) "Part." In regard to Proteobacterial families, "Gram(−) Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram(−) Proteobacteria Subgroup 1" include: 1) *Azotobacter* group bacteria of the genus *Azorhizophilus*; 2) Pseudomonadaceae family bacteria of the genera *Cellvibrio*, *Oligella*, and *Teredinibacter*; 3) Rhizobiaceae family bacteria of the genera *Chelatobacter*, *Ensifer*, *Liberibacter* (also called "*Candidatus Liberibacter*"), and *Sinorhizobium*; and 4) Methylococcaceae family bacteria of the genera *Methylobacter*, *Methylocaldum*, *Methylomicrobium*, *Methylosarcina*, and *Methylosphaera*.

Embodiments of the present invention include wherein the host cell is selected from "Gram(−) Proteobacteria Subgroup 1," as defined above.

In another embodiment, the host cell is selected from "Gram(−) Proteobacteria Subgroup 2." "Gram(−) Proteobacteria Subgroup 2" is defined as the group of Proteobacteria of the following genera (with the total numbers of catalog-listed, publicly-available, deposited strains thereof indicated in parenthesis, all deposited at ATCC, except as otherwise indicated): *Acidomonas* (2); *Acetobacter* (93); *Gluconobacter* (37); *Brevundimonas* (23); *Beijerinckia* (13); *Derxia* (2); *Brucella* (4); *Agrobacterium* (79); *Chelatobacter* (2); *Ensifer* (3); *Rhizobium* (144); *Sinorhizobium* (24); *Blastomonas* (1); *Sphingomonas* (27); *Alcaligenes* (88); *Bordetella* (43); *Burkholderia* (73); *Ralstonia* (33); *Acidovorax* (20); *Hydrogenophaga* (9); *Zoogloea* (9); *Methylobacter* (2); *Methylocaldum* (1 at NCIMB); *Methylococcus* (2); *Methylomicrobium* (2); *Methylomonas* (9); *Methylosarcina* (1); *Methylosphaera*; *Azomonas* (9); *Azorhizophilus* (5); *Azotobacter* (64); *Cellvibrio* (3); *Oligella* (5); *Pseudomonas* (1139); *Francisella* (4); *Xanthomonas* (229); *Stenotrophomonas* (50); and *Oceanimonas* (4).

Exemplary host cell species of "Gram(−) Proteobacteria Subgroup 2" include, but are not limited to the following bacteria (with the ATCC or other deposit numbers of exemplary strain(s) thereof shown in parenthesis): *Acidomonas methanolica* (ATCC 43581); *Acetobacter aceti* (ATCC 15973); *Gluconobacter oxydans* (ATCC 19357); *Brevundimonas diminuta* (ATCC 11568); *Beijerinckia indica* (ATCC 9039 and ATCC 19361); *Derxia gummosa* (ATCC 15994); *Brucella melitensis* (ATCC 23456), *Brucella abortus* (ATCC 23448); *Agrobacterium tumefaciens* (ATCC 23308), *Agrobacterium radiobacter* (ATCC 19358), *Agrobacterium rhizogenes* (ATCC 11325); *Chelatobacter heintzii* (ATCC 29600); *Ensifer adhaerens* (ATCC 33212); *Rhizobium leguminosarum* (ATCC 10004); *Sinorhizobium fredii* (ATCC 35423); *Blastomonas natatoria* (ATCC 35951); *Sphingomonas paucimobilis* (ATCC 29837); *Alcaligenes faecalis* (ATCC 8750); *Bordetella pertussis* (ATCC 9797); *Burkholderia cepacia* (ATCC 25416); *Ralstonia pickettii* (ATCC 27511); *Acidovorax facilis* (ATCC 11228); *Hydrogenophaga flava* (ATCC 33667); *Zoogloea ramigera* (ATCC 19544); *Methylobacter luteus* (ATCC 49878); *Methylocaldum gracile* (NCIMB 11912); *Methylococcus capsulatus* (ATCC 19069); *Methylomicrobium agile* (ATCC 35068); *Methylomonas methanica* (ATCC 35067); *Methylosarcina fibrata* (ATCC 700909); *Methylosphaera hansonii* (ACAM 549); *Azomonas agilis* (ATCC 7494); *Azorhizophilus paspali* (ATCC 23833); *Azotobacter chroococcum* (ATCC 9043); *Cellvibrio mixtus* (UQM 2601); *Oligella urethralis* (ATCC 17960); *Pseudomonas aeruginosa* (ATCC 10145), *Pseudomonas fluorescens* (ATCC 35858); *Francisella tularensis* (ATCC 6223); *Stenotrophomonas maltophilia* (ATCC 13637); *Xanthomonas campestris* (ATCC 33913); and *Oceanimonas doudoroffii* (ATCC 27123).

In another embodiment, the host cell is selected from "Gram(−) Proteobacteria Subgroup 3." "Gram(−) Proteobacteria Subgroup 3" is defined as the group of Proteobacteria of the following genera: *Brevundimonas*; *Agrobacterium*; *Rhizobium*; *Sinorhizobium*; *Blastomonas*; *Sphingomonas*; *Alcaligenes*; *Burkholderia*; *Ralstonia*; *Acidovorax*; *Hydrogenophaga*; *Methylobacter*; *Methylocaldum*; *Methylococcus*; *Methylomicrobium*; *Methylomonas*; *Methylosarcina*; *Methylosphaera*; *Azomonas*; *Azorhizophilus*; *Azotobacter*; *Cellvibrio*; *Oligella*; *Pseudomonas*; *Teredinibacter*; *Francisella*; *Stenotrophomonas*; *Xanthomonas*; and *Oceanimonas*.

In another embodiment, the host cell is selected from "Gram(−) Proteobacteria Subgroup 4." "Gram(−) Proteobacteria Subgroup 4" is defined as the group of Proteobacteria of the following genera: *Brevundimonas*; *Blastomonas*; *Sphingomonas*; *Burkholderia*; *Ralstonia*; *Acidovorax*; *Hydrogenophaga*; *Methylobacter*; *Methylocaldum*; *Methylococcus*; *Methylomicrobium*; *Methylomonas*; *Methylosarcina*; *Methylosphaera*; *Azomonas*; *Azorhizophilus*; *Azotobacter*; *Cellvibrio*; *Oligella*; *Pseudomonas*; *Teredinibacter*; *Francisella*; *Stenotrophomonas*; *Xanthomonas*; and *Oceanimonas*.

In an embodiment, the host cell is selected from "Gram(−) Proteobacteria Subgroup 5." "Gram(−) Proteobacteria Subgroup 5" is defined as the group of Proteobacteria of the following genera: *Methylobacter*; *Methylocaldum*; *Methylococcus*; *Methylomicrobium*; *Methylomonas*; *Methylosarcina*; *Methylosphaera*; *Azomonas*; *Azorhizophilus*; *Azotobacter*; *Cellvibrio*; *Oligella*; *Pseudomonas*; *Teredinibacter*; *Francisella*; *Stenotrophomonas*; *Xanthomonas*; and *Oceanimonas*.

The host cell can be selected from "Gram(−) Proteobacteria Subgroup 6." "Gram(−) Proteobacteria Subgroup 6" is defined as the group of Proteobacteria of the following genera: *Brevundimonas*; *Blastomonas*; *Sphingomonas*; *Burkholderia*; *Ralstonia*; *Acidovorax*; *Hydrogenophaga*; *Azomonas*; *Azorhizophilus*; *Azotobacter*; *Cellvibrio*; *Oligella*; *Pseudomonas*; *Teredinibacter*; *Stenotrophomonas*; *Xanthomonas*; and *Oceanimonas*.

The host cell can be selected from "Gram(−) Proteobacteria Subgroup 7." "Gram(−) Proteobacteria Subgroup 7" is defined as the group of Proteobacteria of the following genera: *Azomonas; Azorhizophilus; Azotobacter; Cellvibrio; Oligella; Pseudomonas; Teredinibacter; Stenotrophomonas; Xanthomonas*; and *Oceanimonas*.

The host cell can be selected from "Gram(−) Proteobacteria Subgroup 8." "Gram(−) Proteobacteria Subgroup 8" is defined as the group of Proteobacteria of the following genera: *Brevundimonas; Blastomonas; Sphingomonas; Burkholderia; Ralstonia; Acidovorax; Hydrogenophaga; Pseudomonas; Stenotrophomonas; Xanthomonas*; and *Oceanimonas*.

The host cell can be selected from "Gram(−) Proteobacteria Subgroup 9." "Gram(−) Proteobacteria Subgroup 9" is defined as the group of Proteobacteria of the following genera: *Brevundimonas; Burkholderia; Ralstonia; Acidovorax; Hydrogenophaga; Pseudomonas; Stenotrophomonas*; and *Oceanimonas*.

The host cell can be selected from "Gram(−) Proteobacteria Subgroup 10." "Gram(−) Proteobacteria Subgroup 10" is defined as the group of Proteobacteria of the following genera: *Burkholderia; Ralstonia; Pseudomonas; Stenotrophomonas*; and *Xanthomonas*.

The host cell can be selected from "Gram(−) Proteobacteria Subgroup 11." "Gram(−) Proteobacteria Subgroup 11" is defined as the group of Proteobacteria of the genera: *Pseudomonas; Stenotrophomonas*; and *xanthomonas*.

The host cell can be selected from "Gram(−) Proteobacteria Subgroup 12." "Gram(−) Proteobacteria Subgroup 12" is defined as the group of Proteobacteria of the following genera: *Burkholderia; Ralstonia; Pseudomonas*.

The host cell can be selected from "Gram(−) Proteobacteria Subgroup 13." "Gram(−) Proteobacteria Subgroup 13" is defined as the group of Proteobacteria of the following genera: *Burkholderia; Ralstonia; Pseudomonas*; and *Xanthomonas*.

The host cell can be selected from "Gram(−) Proteobacteria Subgroup 14." "Gram(−) Proteobacteria Subgroup 14" is defined as the group of Proteobacteria of the following genera: *Pseudomonas* and *Xanthomonas*.

The host cell can be selected from "Gram(−) Proteobacteria Subgroup 15." "Gram(−) Proteobacteria Subgroup 15" is defined as the group of Proteobacteria of the genus *Pseudomonas*.

The host cell can be selected from "Gram(−) Proteobacteria Subgroup 16." "Gram(−) Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoalcaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila; Pseudomonas alginovora; Pseudomonas andersonii; Pseudomonas asplenii* (ATCC 23835); *Pseudomonas azelaica* (ATCC 27162); *Pseudomonas beijerinckii* (ATCC 19372); *Pseudomonas borealis; Pseudomonas boreopolis* (ATCC 33662); *Pseudomonas brassicacearum; Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens; Pseudomonas diterpeniphila; Pseudomonas elongata* (ATCC 10144); *Pseudomonas flectens* (ATCC 12775); *Pseudomonas azotoformans; Pseudomonas brenneri; Pseudomonas cedrella; Pseudomonas corrugata* (ATCC 29736); *Pseudomonas extremorientalis; Pseudomonas fluorescens* (ATCC 35858); *Pseudomonas gessardii; Pseudomonas libanensis; Pseudomonas mandelii* (ATCC 700871); *Pseudomonas marginalis* (ATCC 10844); *Pseudomonas migulae; Pseudomonas mucidolens* (ATCC 4685); *Pseudomonas orientalis; Pseudomonas rhodesiae; Pseudomonas synxantha* (ATCC 9890); *Pseudomonas tolaasii* (ATCC 33618); *Pseudomonas veronii* (ATCC 700474); *Pseudomonas frederiksbergensis; Pseudomonas geniculata* (ATCC 19374); *Pseudomonas gingeri; Pseudomonas graminis; Pseudomonas grimontii; Pseudomonas halodenitrificans; Pseudomonas halophila; Pseudomonas hibiscicola* (ATCC 19867); *Pseudomonas huttiensis* (ATCC 14670); *Pseudomonas hydrogenovora; Pseudomonas jessenii* (ATCC 700870); *Pseudomonas kilonensis; Pseudomonas lanceolata* (ATCC 14669); *Pseudomonas lini; Pseudomonas marginata* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila; Pseudomonas fulva* (ATCC 31418); *Pseudomonas monteilii* (ATCC 700476); *Pseudomonas mosselii; Pseudomonas oryzihabitans* (ATCC 43272); *Pseudomonas plecoglossicida* (ATCC 700383); *Pseudomonas putida* (ATCC 12633); *Pseudomonas reactans; Pseudomonas spinosa* (ATCC 14606); *Pseudomonas balearica; Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas cichori* (ATCC 10857); *Pseudomonas ficuserectae* (ATCC 35104); *Pseudomonas fuscovaginae; Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans; Pseudomonas thivervalensis; Pseudomonas vancouverensis* (ATCC 700688); *Pseudomonas wisconsinensis*; and *Pseudomonas xiamenensis*.

The host cell can be selected from "Gram(−) Proteobacteria Subgroup 17." "Gram(−) Proteobacteria Subgroup 17" is defined as the group of Proteobacteria known in the art as the "fluorescent Pseudomonads" including those belonging, e.g., to the following *Pseudomonas* species: *Pseudomonas azotoformans; Pseudomonas brenneri; Pseudomonas cedrella; Pseudomonas corrugata; Pseudomonas extremorientalis; Pseudomonas fluorescens; Pseudomonas gessardii; Pseudomonas libanensis; Pseudomonas mandelii; Pseudomonas marginalis; Pseudomonas migulae; Pseudomonas mucidolens; Pseudomonas orientalis; Pseudomonas rhodesiae; Pseudomonas synxantha; Pseudomonas tolaasii*; and *Pseudomonas veronii*.

The host cell can be selected from "Gram(−) Proteobacteria Subgroup 18." "Gram(−) Proteobacteria Subgroup 18" is defined as the group of all subspecies, varieties, strains, and other sub-special units of the species *Pseudomonas fluorescens*, including those belonging, e.g., to the following (with the ATCC or other deposit numbers of exemplary strain(s) shown in parenthesis): *Pseudomonas fluorescens* biotype A, also called biovar 1 or biovar I (ATCC 13525); *Pseudomonas*

*fluorescens* biotype B, also called biovar 2 or biovar II (ATCC 17816); *Pseudomonas fluorescens* biotype C, also called biovar 3 or biovar III (ATCC 17400); *Pseudomonas fluorescens* biotype F, also called biovar 4 or biovar IV (ATCC 12983); *Pseudomonas fluorescens* biotype G, also called biovar 5 or biovar V (ATCC 17518); *Pseudomonas fluorescens* biovar VI; *Pseudomonas fluorescens* Pf0-1; *Pseudomonas fluorescens* Pf-5 (ATCC BAA-477); *Pseudomonas fluorescens* SBW25; and *Pseudomonas fluorescens* subsp. *cellulosa* (NCIMB 10462).

The host cell can be selected from "Gram(−) Proteobacteria Subgroup 19." "Gram(−) Proteobacteria Subgroup 19" is defined as the group of all strains of *Pseudomonas fluorescens* biotype A. One strain of this biotype is *P. fluorescens* strain MB11 (see U.S. Pat. No. 5,169,760 to Wilcox), and derivatives thereof.

In some embodiments the host cell is any of the Proteobacteria of the order Pseudomonadales. In other embodiments the host cell is any of the Proteobacteria of the family Pseudomonadaceae.

In additional embodiments the host cell is selected from "Gram(−) Proteobacteria Subgroup 1." In some embodiments the host cell is selected from "Gram(−) Proteobacteria Subgroup 2." In other embodiments the host cell is selected from "Gram(−) Proteobacteria Subgroup 3." In additional embodiments the host cell is selected from "Gram(−) Proteobacteria Subgroup 5." For some embodiments the host cell is selected from "Gram(−) Proteobacteria Subgroup 7." Yet, in other embodiments the host cell is selected from "Gram(−) Proteobacteria Subgroup 12", "Gram(−) Proteobacteria Subgroup 15", "Gram(−) Proteobacteria Subgroup 17", "Gram(−) Proteobacteria Subgroup 18", and/or "Gram(−) Proteobacteria Subgroup 19".

Additional *P. fluorescens* strains that can be used in the present invention include *Pseudomonas fluorescens* Migula and *Pseudomonas fluorescens* Loitokitok, having the following ATCC designations: [NCIB 8286]; NRRL B-1244; NCIB 8865 strain CO1; NCIB 8866 strain CO2; 1291 [ATCC 17458; IFO 15837; NCIB 8917; LA; NRRL B-1864; pyrrolidine; PW2 [ICMP 3966; NCPPB 967; NRRL B-899]; 13475; NCTC 10038; NRRL B-1603 [6; IFO 15840]; 52-1C; CCEB 488-A [BU 140]; CCEB 553 [IEM 15/47]; IAM 1008 [AHH-27]; IAM 1055 [AHH-23]; 1 [IFO 15842]; 12 [ATCC 25323; NIH 11; den Dooren de Jong 216]; 18 [IFO 15833; WRRL P-7]; 93 [TR-10]; 108 [52-22; IFO 15832]; 143 [IFO 15836; PL]; 149 [2-40-40; IFO 15838]; 182 [IFO 3081; PJ 73]; 184 [IFO 15830]; 185 [W2 L-1]; 186 [IFO 15829; PJ 79]; 187 [NCPPB 263]; 188 [NCPPB 316]; 189 [PJ227; 1208]; 191 [IFO 15834; PJ 236; 22/1]; 194 [Klinge R-60; PJ 253]; 196 [PJ 288]; 197 [PJ 290]; 198 [PJ 302]; 201 [PJ 368]; 202 [PJ 372]; 203 [PJ 376]; 204 [IFO 15835; PJ 682]; 205 [PJ 686]; 206 [PJ 692]; 207 [PJ 693]; 208 [PJ 722]; 212 [PJ 832]; 215 [PJ 849]; 216 [PJ 885]; 267 [B-9]; 271 [B-1612]; 401 [C71A; IFO 15831; PJ 187]; NRRL B-3178 [4; IFO 15841]; KY 8521; 3081; 30-21; [IFO 3081]; N; PYR; PW; D946-B83 [BU 2183; FERM-P 3328; P-2563 [FERM-P 2894; IFO 13658]; IAM-1126 [43F]; M-1; A506 [A5-06]; A505 [A5-05-1]; A526 [A5-26]; B69; 72; NRRL B-4290; PMW6 [NCIB 11615]; SC 12936; A1 [IFO 15839]; F 1847 [CDC-EB]; F 1848 [CDC 93]; NCIB 10586; P17; F-12; AmMS 257; PRA25; 6133D02; 6519E01; N1; SC15208; BNL-WVC; NCTC 2583 [NCIB 8194]; H13; 1013 [ATCC 11251; CCEB 295]; IFO 3903; 1062; or Pf-5.

III. Nucleic Acid Constructs

Nucleic acid constructs are provided for use in the present invention, comprising nucleic acids encoding peptides of interest operably linked to carbon source inducible promoters. In some embodiments at least one carbon source inducible promoter is contained on a nucleic acid construct and operably linked to a nucleic acid encoding at least one peptide of interest. In other embodiments the carbon source inducible promoter is mannitol, glucitol, arabitol, or derivative thereof. The peptide of interest can be a monomer. In an alternative embodiment, the carbon source inducible promoter is operably linked to a nucleic acid sequence encoding more than one monomer. In other embodiments more than one mannitol, glucitol, or arabitol-inducible promoter is contained on a nucleic acid construct, wherein the promoters are covalently linked in tandem, and operably linked to a nucleic acid encoding a peptide of interest. In another embodiment, more than one mannitol, glucitol, or arabitol-inducible promoter is contained on the nucleic acid construct, wherein each promoter is separately and operably linked to a nucleic acid encoding a peptide of interest. In some embodiments the peptides of interest may be the same peptides or different peptides.

In another embodiment, the nucleic acid construct can contain a mannitol, glucitol, or arabitol-inducible promoter and another promoter that is not induced by mannitol, glucitol, arabitol, or a derivative thereof. The mannitol-inducible promoter can be covalently linked in tandem, or separate and operably linked to a separate nucleic acid encoding a peptide of interest. For example, one promoter can be a mannitol, glucitol, or arabitol-inducible promoter and the other promoter can be a lac (IPTG), lacUV5 (IPTG), tac (IPTG), trc (IPTG), $P_{syn}$ (IPTG), trp (tryptophan starvation), araBAD (1-arabinose), Ipp$^a$ (IPTG), lpp-lac (IPTG), phoA (phosphate starvation), recA (nalidixic acid), proU (osmolarity), cst-1 (glucose starvation), tetA (tretracylin), cadA (pH), nar (anaerobic conditions), PL (thermal shift to 42° C.), cspA (thermal shift to 20° C.), T7 (thermal induction), T7-lac operator (IPTG), T3-lac operator (IPTG), T5-lac operator (IPTG), T4 gene32 (T4 infection), nprM-lac operator (IPTG), Pm (alkyl- or halo-benzoates), Pu (alkyl- or halo-toluenes), Psal (salicylates), ant (anthranilate), ben (benzoate) or VHb (oxygen) promoter. See, for example, Makrides, S. C. (1996) Microbiol. Rev. 60, 512-538; Hannig G. & Makrides, S. C. (1998) TIBTECH 16, 54-60; Stevens, R. C. (2000) Structures 8, R177-R185. See, e.g.: J. Sanchez-Romero & V. De Lorenzo, Genetic Engineering of Nonpathogenic *Pseudomonas* strains as Biocatalysts for Industrial and Environmental Processes, in Manual of Industrial Microbiology and Biotechnology (A. Demain & J. Davies, eds.) pp. 460-74 (1999) (ASM Press, Washington, D.C.); H. Schweizer, Vectors to express foreign genes and techniques to monitor gene expression for Pseudomonads, Current Opinion in Biotechnology, 12:439-445 (2001); and R. Slater & R. Williams, The Expression of Foreign DNA in Bacteria, in Molecular Biology and Biotechnology (J. Walker & R. Rapley, eds.) pp. 125-54 (2000) (The Royal Society of Chemistry, Cambridge, UK).

Other Elements

Other regulatory elements can be included in the nucleic acid expression construct. Such elements include, but are not limited to, for example, transcriptional enhancer sequences, translational enhancer sequences, other promoters, activators, translational start and stop signals, transcription terminators, cistronic regulators, polycistronic regulators, tag sequences, such as nucleotide sequence "tags" and "tag" peptide coding sequences, which facilitates identification, separation, purification, or isolation of an expressed polypeptide, including His-tag, Flag-tag, T7-tag, S-tag, HSV-tag, B-tag, Strep-tag, polyarginine, polycysteine, polyphenylalanine, polyaspartic acid, (Ala-Trp-Trp-Pro)n, thioredoxin, beta-galactosidase, chloramphenicol acetyltransferase, cyclomaltodextrin gluconotransferase, CTP:CMP-3-deoxy-D-manno-octulosonate cytidyltransferase, trpe or trpLE, avidin, streptavidin, T7 gene 10, T4 gp55, Staphylococcal peptide A, streptococcal peptide G, GST, DHFR, CBP, MBP, galactose binding domain, Calmodulin binding domain, GFP, KSI, c-myc, ompT, ompA, pelB, NusA, ubiquitin, and hemosylin A.

A peptide-encoding gene according to the present invention can include, in addition to the peptide coding sequence, the following regulatory elements operably linked thereto: a promoter, a ribosome binding site (RBS), a transcription terminator, translational start and stop signals. Useful RBSs can be obtained from any of the species useful as host cells in expression systems according to the present invention, preferably from the selected host cell. Many specific and a variety of consensus RBSs are known, e.g., those described in and referenced by D. Frishman et al., Starts of bacterial genes: estimating the reliability of computer predictions, Gene 234 (2):257-65 (8 Jul. 1999); and B. E. Suzek et al., A probabilistic method for identifying start codons in bacterial genomes, Bioinformatics 17(12):1123-30 (December 2001). In addition, either native or synthetic RBSs may be used, e.g., those described in: EP 0207459 (synthetic RBSs); O. Ikehata et al., Primary structure of nitrile hydratase deduced from the nucleotide sequence of a *Rhodococcus* species and its expression in *Escherichia coli, Eur. J. Biochem.* 181(3):563-70 (1989) (native RBS sequence of AAGGAAG). Further examples of methods, vectors, and translation and transcription elements, and other elements useful in the present invention are described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox.

Vectors

Generally, the nucleic acid construct will be contained on an expression vector, and will include origins of replication and selectable markers permitting transformation of the bacterial host cell. The recombinant peptide of interest is assembled in appropriate phase with translation initiation and termination sequences, and in certain embodiments, a leader sequence capable of directing secretion of the translated polypeptide can be included in the nucleic acid construct. Optionally, and in accordance with the present invention, the recombinant peptide sequence can encode a fusion polypeptide including an N-terminal identification peptide imparting desired characteristics, e.g., stabilization or simplified purification of expressed recombinant product. In certain embodiments, the vector may be maintained in an episomal fashion (extra-chromosomally), or be inserted into the genome of the host bacterial cell.

Useful expression vectors for use with bacteria in expressing recombinant peptides are constructed by inserting a structural DNA sequence encoding a desired target peptide together with suitable translation initiation and termination signals in operable reading phase with the carbon source-inducible promoter. The vector will comprise one or more phenotypic selectable markers and an origin of replication to ensure maintenance of the vector and to, if desirable, provide amplification within the host. Alternatively, the vector can further provide sequences that allow for integration into the genome of the host cell. Suitable hosts for transformation in accordance with the present disclosure include any bacterial cell capable of expressing a recombinant peptide driven by a carbon source inducible promoter. In some embodiments the bacteria can include various species within the genera *Escherichia* and *Pseudomonas*.

Vectors are known in the art as useful for expressing recombinant peptides in host cells, and any of these may be modified and used for expressing recombinant peptides of interest according to the present invention. Such vectors include, e.g., plasmids, cosmids, and phage expression vectors. Examples of useful plasmid vectors that can be modified for use in the present invention include, but are not limited to, the expression plasmids pBBR1MCS, pDSK519, pKT240, pML122, pPS10, RK2, RK6, pRO1600, and RSF1010. Further examples can include pALTER-Ex1, pALTER-Ex2, pBAD/His, pBAD/Myc-His, pBAD/gIII, pCal-n, pCal-n-EK, pCal-c, pCal-Kc, pcDNA 2.1, pDUAL, pET-3a-c, pET 9a-d, pET-11a-d, pET-12a-c, pET-14b, pET15b, pET-16b, pET-17b, pET-19b, pET-20b(+), pET-21a-d(+), pET-22b(+), pET-23a-d(+), pET24a-d(+), pET-25b(+), pET-26b(+), pET-27b (+), pET28a-c(+), pET-29a-c(+), pET-30a-c(+), pET31b(+), pET-32a-c(+), pET-33b(+), pET-34b(+), pET35b(+), pET-36b(+), pET-37b(+), pET-38b(+), pET-39b(+), pET-40b(+), pET-41a-c(+), pET-42a-c(+), pET-43a-c(+), pETBlue-1, pETBlue-2, pETBlue-3, pGEMEX-1, pGEMEX-2, pGEX1XT, pGEX-2T, pGEX-2TK, pGEX-3X, pGEX-4T, pGEX-5X, pGEX-6P, pHAT10/11/12, pHAT20, pHAT-GF-Puv, pKK223-3, pLEX, pMAL-c2X, pMAL-c2E, pMAL-c2g, pMAL-p2X, pMAL-p2E, pMAL-p2G, pProEX HT, pPROLar.A, pPROTet.E, pQE-9, pQE-16, pQE-30/31/32, pQE-40, pQE-50, pQE-70, pQE-80/81/82L, pQE-100, pRSET, and pSE280, pSE380, pSE420, pThioHis, pTrc99A, pTrcHis, pTrcHis2, pTriEx-1, pTriEx-2, pTrxFus. Other examples of such useful vectors include those described by, e.g.: N. Hayase, in Appl. Envir. Microbiol. 60(9):3336-42 (September 1994); A. A. Lushnikov et al., in Basic Life Sci. 30:657-62 (1985); S. Graupner & W. Wackemagel, in Biomolec. Eng. 17(1):11-16. (October 2000); H. P. Schweizer, in Curr. Opin. Biotech. 12(5):439-45 (October 2001); M. Bagdasarian & K. N. Timmis, in Curr. Topics Microbiol. Immunol. 96:47-67 (1982); T. Ishii et al., in FEMS Microbiol. Lett. 116(3):307-13 (Mar. 1, 1994); I. N. Olekhnovich & Y. K. Fomichev, in Gene 140(1):63-65 (Mar. 11, 1994); M. Tsuda & T. Nakazawa, in Gene 136(1-2):257-62 (Dec. 22, 1993); C. Nieto et al., in Gene 87(1):145-49 (Mar. 1, 1990); J. D. Jones & N. Gutterson, in Gene 61(3):299-306 (1987); M. Bagdasarian et al., in Gene 16(1-3):237-47 (December 1981); H. P. Schweizer et al., in Genet. Eng. (NY) 23:69-81 (2001); P. Mukhopadhyay et al., in J. Bact. 172(1):477-80 (January 1990); D. O. Wood et al., in J. Bact. 145(3):1448-51 (March 1981); and R. Holtwick et al., in Microbiology 147(Pt 2):337-44 (February 2001).

Further examples of expression vectors that can be useful in bacterial host cells include those listed in Table 5 as derived from the indicated replicons:

TABLE 5

Some Examples of Useful Expression Vectors

| Replicon | Vector(s) |
|---|---|
| $p$PS10 | $p$CN39, $p$CN51 |
| RSF1010 | $p$KT261-3 |
|  | $p$MMB66EH |
|  | $p$EB8 |
|  | $p$PLGN1 |
|  | $p$MYC1050 |
| RK2/RP1 | $p$RK415 |
|  | $p$JB653 |
| $p$RO1600 | $p$UCP |
|  | $p$BSP |

The expression plasmid, RSF1010, is described, e.g., by F. Heffron et al., in Proc. Nat'l Acad. Sci. USA 72(9):3623-27 (September 1975), and by K. Nagahari & K. Sakaguchi, in J. Bact. 133(3):1527-29 (March 1978). Plasmid RSF1010 and derivatives thereof are can be used as vectors in the present invention. Exemplary, useful derivatives of RSF1010, which are known in the art, include, e.g., pKT212, pKT214, pKT231 and related plasmids, and pMYC1050 and related plasmids (see, e.g., U.S. Pat. Nos. 5,527,883 and 5,840,554 to Thompson et al.), such as, e.g., pMYC1803. Plasmid pMYC1803 is derived from the RSF 1010-based plasmid pTJS260 (see U.S. Pat. No. 5,169,760 to Wilcox), which carries a regulated tetracycline resistance marker and the replication and mobilization loci from the RSF 1010 plasmid. Other exemplary useful vectors include those described in U.S. Pat. No. 4,680,264 to Puhler et al.

In additional embodiments an expression plasmid is used as the expression vector. In another embodiment, RSF110 or a derivative thereof is used as the expression vector. In still another embodiment, pMYC1050 or a derivative thereof, or pMYC1803 or a derivative thereof, is used as the expression vector.

IV. Expression of Recombinant Polypeptides in a Bacterial Host Cell

Embodiments of the present invention include processes for expressing recombinant peptides for use in peptide production. In general, the process provides expression of a nucleic acid construct comprising nucleic acids encoding at least one recombinant polypeptide operably linked to at least one mannitol, arabitol, or glucitol-inducible promoter, wherein the nucleic acid construct is expressed in a host cell that is rendered deficient in its ability to metabolize or degrade mannitol, glucitol, or arabitol, or derivatives or analogues thereof. In some embodiments the inducible promoter can be a mannitol inducible promoter, or derivative thereof. In other embodiments the host cell is rendered deficient for the metabolization or degradation of mannitol, which is used as an inducer in promoter induction. In one embodiment, the host cell is *Escherichia coli*. In another embodiment, the host cell can be a Pseudomonad or closely related bacterial cell. In additional embodiments the host cell can be a *Pseudomonas fluorescens* cell. In some embodiments the host cell is deficient for the metabolization or degradation of mannitol, arabitol, or glucitol, or analogues or derivatives thereof, and expresses a nucleic acid encoding at least one recombinant polypeptide operably linked to at least one mannitol, arabitol, glucitol, or glycerol-inducible promoter.

The method generally includes:
a) providing a host cell, preferably an *E. coli* or *Pseudomonas fluorescens*, as described in the present invention,
b) transfecting the host cell with at least one nucleic acid expression vector comprising at least one recombinant polypeptide of interest operably linked to at least one mannitol, glucitol, or arabitol-inducible promoter, and growing the host cell in a sufficient growth medium; and
c) adding a mannitol, glucitol, or arabitol, or analogues or derivatives thereof to the growth medium in an amount capable of inducing the expression of the peptide of interest, wherein the host cell is rendered incapable of degrading or metabolizing the added mannitol, glucitol, or arabitol, or analogues or derivatives thereof, and
d) expressing the target recombinant polypeptide of interest.

The method can further comprise e) transfecting the host cell with at least one nucleic acid expression construct comprising an additional inducible promoter operably linked to at least one peptide of interest. In addition, the method can further comprise f) isolating at least one recombinant peptide. The method can also include g) purifying at least one recombinant peptide.

Alternatively, the method can comprise in step c) adding glycerol, or a derivative or analogue thereof, to the growth medium in an amount capable of inducing the peptide of interest, wherein the host cell is rendered incapable of degrading or metabolizing mannitol, glucitol, or arabitol, or analogues or derivatives thereof.

In some embodiments the inducible promoter is a mannitol-inducible promoter. In other embodiments, the mannitol, glucitol, or arabitol-inducible promoter is also capable of induction by glycerol.

Wherein the method further comprises e) transfecting the host cell with at least one nucleic acid expression construct comprising an additional inducible promoter operably linked to at least one peptide of interest, the peptide of interest can be the same or a different peptide of interest from the one encoded by the nucleic acid operably linked to the mannitol, arabitol, or glucitol-inducible promoter. Other inducible promoters can be, for example, a lac or tac family promoter, including Plac, Ptac, Ptrc, PtacII, PlacUV5, lpp$^a$, lpp-PlacUV5, lpp-lac, nprM-lac, T7lac, T5lac, T3lac, and Pmac, trp (tryptophan starvation), araBAD (1-arabinose), phoA (phosphate starvation), recA (nalidixic acid), proU (osmolarity), cst-1 (glucose starvation), tetA (tretracylin), cadA (pH), nar (anaerobic conditions), PL (thermal shift to 42° C.), cspA (thermal shift to 20° C.), T7 (thermal induction), T4 gene32 (T4 infection), Pm (alkyl- or halo-benzoates), Pu (alkyl- or halo-toluenes), Psal (salicylates), ant (anthranilate), ben (benzoate) or VHb (oxygen) promoter.

In some embodiments the present invention can employ more than one mannitol, glucitol, or arabitol-inducible promoter in producing a peptide, or more than one peptide, of interest. In other embodiments the multiple promoters can have different sequences, with each promoter capable of induction by the same carbon source at a different rate based on the specific sequence utilized. For example, one mannitol-inducible promoter sequence may be capable of expressing a peptide of interest at a higher expression than a mannitol-inducible promoter with a differing nucleic acid sequence based on differing inherent characteristics or modifications. Alternatively, enhancer elements may be contained, in addition to the promoter sequence, within the promoter region that affect the rate of expression of the promoter sequences differently based on the spacing or linkage of the respective promoters to the enhancer elements, whether the promoter sequences are the same or different.

In embodiments of the present invention the mannitol, glucitol, or arabitol-inducible promoter is used concomitantly in a bacterial host cell with a lac or tac family promoter including, for example, Plac, Ptac, Ptrc, PtacII, PlacUV5, lpp-lac, nprM-lac, T7lac, T5lac, T3lac, and Pmac.

In some embodiments the expression system is capable of expressing the target polypeptide at a total productivity of polypeptide of at least 0.1 g/L to at least 80 g/L. In other embodiments the recombinant polypeptide is expressed at a level of at least 0.3 g/L, 0.4 g/L, 0.7 g/L, 1.0 g/L, 1.5 g/L, 2 g/L, 3 g/L, 4 g/L, 5 g/L, 6 g/L, 7 g/L, 8 g/L, 9 g/L, 10 g/L, 12 g/L, 15 g/L, 20 g/L, 25 g/L, 30 g/L, 35 g/L, 40 g/L, 45 g/L, 50 g/L, 60 g/L, 70 g/L, or at least 80 g/L.

In one embodiment, at least one recombinant peptide can be expressed in a bacterial cell that is incapable of degrading or metabolizing mannitol, arabitol, or glucitol, wherein expression of the recombinant polypeptide is induced utilizing mannitol, arabitol, glucitol, or glycerol, or derivatives or analogues thereof. Alternatively, more than one recombinant peptide can be expressed in a cell of the present invention, wherein the nucleic acids encoding the recombinant peptides can be contained on the same vector, or alternatively, on multiple vectors, and operably linked to more than one promoter, including at least one mannitol, arabitol, or glucitol-inducible promoter.

In yet another embodiment, nucleic acid constructs encoding different target polypeptides can be maintained in a bacterial host cell incapable of degrading or metabolizing mannitol, glucitol, or arabitol, or derivatives or analogues thereof, wherein mannitol, glucitol, arabitol, or glycerol is utilized to induce expression of the target polypeptides. In such embodiments, a first nucleic acid encoding a first peptide of interest, and a second nucleic acid encoding second peptide of interest are regulated independently of each other through the use of different promoters, wherein at least one promoter is a mannitol, glucitol, or arabitol-inducible promoter. Such multi-target gene expression systems allow for independent regulation and optimization of expression of each peptide. In certain embodiments, one expressed peptide can modulate the expression or resultant peptide characteristic of the other peptide of interest.

Examples of such a multi-target gene system include, but are not limited to: (1) systems in which the expression product of one of the target genes interacts with the other target gene itself, (2) systems in which the expression product of one of the target genes interacts with the other target gene's expression product, e.g., a peptide and its binding peptide or the α- and β-polypeptides of an αn-βn peptide; (3) systems in which the two expression products of the two genes both interact with a third component, e.g., a third component present in the host cell; (4) systems in which the two expression products of the two genes both participate in a common biocatalytic pathway; and (5) systems in which the two expression products of the two genes function independently of one another, e.g., a bi-clonal antibody expression system.

In one example of a multi-target gene system of the above-listed type (1), a first target gene can encode a desired target peptide, wherein the first target gene is under the control of a regulatable promoter; the second target gene may then encode a peptide involved in regulating the promoter of the first target gene, e.g., the second target gene may encode the first target gene's promoter activator or repressor peptide. In an example in which the second gene encodes a promoter regulatory peptide for the first gene, the coding sequence of the second gene can be under the control of a mannitol-inducible promoter. In some embodiments the second gene will be part of a separate DNA construct that is maintained in the cell as a high-copy-number construct with a copy number of at least 10, 20, 30, 40, 50, or more than 50 copies being maintained in the host cell, or that has been inserted into the genome of the cell.

In another example of a dual-target gene system, the second target gene can encode a peptide that assists in the folding of the first target gene product, or assists in directing the peptide of interest to a cell compartment (e.g., a chaperone protein). For example, the first target gene product can be a peptide that is normally expressed in a bacterial host cell in an incorrectly folded form. Alternatively, the first target gene product can be a peptide that is normally expressed in a bacterial cell in an insoluble form. The second target gene, in these cases, can encode for a protein that assists in properly folding the protein, or directing the protein to a specific location in the cell (e.g., such as the periplasm). Examples of such peptides and proteins include, but are not limited to: cbpA,
htpG, dnaK, dnaJ, fkbP2, groES, groEL, htpG or cbpA, HSP70 proteins, HSP110/SSE proteins, HSP40 (DNAJ-related) proteins, GRPE-like proteins, HSP90 proteins, CPN60 and CPN10 proteins, Cytosolic chaperonins, HSP100 proteins, Small HSPs, Calnexin and calreticulin, PDI and thioredoxin-related proteins, Peptidyl-prolyl isomerases, Cyclophilin PPIases, FK-506 binding proteins, Parvulin PPIases, Individual chaperonins, Protein specific chaperones, or intramolecular chaperones. Other proteins that can be expressed in the current invention include folding modulators that are generally described in "Guidebook to Molecular Chaperones and Protein-Folding Catalysts" (1997) ed. M. Gething, Melbourne University, Australia.

Transformation

Transformation of the host cells with the vector(s) may be performed using any transformation methodology known in the art, and the bacterial host cells may be transformed as intact cells or as protoplasts (i.e. including cytoplasts). Exemplary transformation methodologies include poration methodologies, e.g., electroporation, protoplast fusion, bacterial conjugation, and divalent cation treatment, e.g., calcium chloride treatment or $CaCl_2/Mg^{2+}$ treatment, or other well known methods in the art. See, e.g., Morrison, J. Bact., 132: 349-351 (1977); Clark-Curtiss & Curtiss, Methods in Enzymology, 101:347-362 (Wu et al., eds, 1983), Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

Selection

Preferably, cells that are not successfully transformed are selected against following transformation, and continuously during the fermentation. The selection marker can be an auxotrophic selection marker or a traditional antibiotic selection marker. When the cell is auxotrophic for multiple nutrient compounds, the auxotrophic cell can be grown on medium supplemented with all of those nutrient compounds until transformed with the prototrophy-restoring vector. Where the selection marker is an antibiotic resistance gene, the associated antibiotic can be added to the medium to select against non transformed and revertant cells, as well known in the art.

Fermentation

As used herein, the term "fermentation" includes both embodiments in which literal fermentation is employed and embodiments in which other, non-fermentative culture modes are employed. Fermentation may be performed at any scale. In some embodiments the fermentation medium may be selected from among rich media, minimal media, a mineral salts media; a rich medium may be used, but is preferably avoided. In another embodiment either a minimal medium or a mineral salts medium is selected.

Mineral salts media consists of mineral salts and a carbon source such as, e.g., glucose, sucrose, or glycerol. Examples of mineral salts media include, e.g., M9 medium, *Pseudomonas* medium (ATCC 179), Davis and Mingioli medium (see, B D Davis & E S Mingioli, in J. Bact. 60:17-28 (1950)). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. No organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A typical mineral salts medium will contain glucose as the carbon source. In comparison to mineral salts media, minimal media can also contain mineral salts and a carbon source, but can be supplemented with, e.g., low levels of amino acids, vitamins, peptones, or other ingredients, though these are added at very minimal levels.

Ideally, the media selected allows for high cell density cultivation (HCDC) for growth of bacterial cells. The HCDC can start as a batch process which is followed by two-phase fed-batch cultivation. After unlimited growth in the batch part, growth can be controlled at a reduced specific growth rate over a period of 3 doubling times in which the biomass concentration can be increased several fold. Further details of such cultivation procedures is described by Riesenberg, D.; Schulz, V.; Knorre, W. A.; Pohl, H. D.; Korz, D.; Sanders, E. A.; Ross, A.; Deckwer, W. D. (1991) "High cell density cultivation of *Escherichia coli* at controlled specific growth rate" J Biotechnol: 20(1) 17-27.

The expression system according to the present invention can be cultured in any fermentation format. For example, batch, fed-batch, semi-continuous, and continuous fermentation modes may be employed herein.

The expression systems according to the present invention are useful for transgene expression at any scale (i.e. volume) of fermentation. Thus, e.g., microliter-scale, centiliter scale, and deciliter scale fermentation volumes may be used; and 1 Liter scale and larger fermentation volumes can be used. In some embodiments the fermentation volume will be at or above 1 Liter. In other embodiments the fermentation volume will be at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters or 50,000 Liters.

In the present invention, growth, culturing, and/or fermentation of the transformed host cells is performed within a temperature range permitting survival of the host cells, preferably a temperature within the range of about 4° C. to about 55° C., inclusive.

Cell Density

In embodiments of the present invention Pseudomonads and closely related bacteria are utilized in the present invention. Pseudomonads, and particularly *Pseudomonas fluorescens*, can be grown in high cell densities. To this end, *Pseudomonas fluorescens* expressions systems according to the present invention can provide a cell density of about 20 g/L or more. The *Pseudomonas fluorescens* expressions systems according to the present invention can likewise provide a cell density of at least about 70 g/L, as stated in terms of biomass per volume, the biomass being measured as dry cell weight.

In some embodiments the cell density will be at least 20 g/L. In another embodiment, the cell density will be at least 25 g/L, 30 g/L, 35 g/L, 40 g/L, 45 g/L, 50 g/L, 60 g/L, 70 g/L, 80 g/L, 90 g/L, 100 g/L, 110 g/L, 120 g/L, 130 g/L, 140 g/L, or at least 150 g/L.

In another embodiments, the cell density at induction will be between 20 g/L and 150 g/L; 20 g/L and 120 g/L; 20 g/L and 80 g/L; 25 g/L and 80 g/L; 30 g/L and 80 g/L; 35 g/L and 80 g/L; 40 g/L and 80 g/L; 45 g/L and 80 g/L; 50 g/L and 80 g/L; 50 g/L and 75 g/L; 50 g/L and 70 g/L; 40 g/L and 80 g/L.

Expression Levels of Recombinant Peptides

The expression systems according to the present invention can express transgenic polypeptides at a level at between 5% and 80% total cell peptide (% tcp). In some embodiments the expression level will be at or above 5%, 8%, 10%, 12%, 15%, 20%, 25%, 30%, 35%, 40%, 45%, 50%, 55%, 60%, 65%, 70%, 75%, or 80% tcp.

Isolation and Purification

The recombinant peptides produced according to this invention may be isolated and purified to substantial purity by standard techniques well known in the art, including, but not limited to, ammonium sulfate or ethanol precipitation, acid extraction, anion or cation exchange chromatography, phosphocellulose chromatography, hydrophobic interaction chromatography, affinity chromatography, nickel chromatography, hydroxylapatite chromatography, reverse phase chromatography, lectin chromatography, preparative electrophoresis, detergent solubilization, selective precipitation with such substances as column chromatography, immunopurification methods, and others. For example, peptides having established molecular adhesion properties can be reversibly fused a ligand. With the appropriate ligand, the peptide can be selectively adsorbed to a purification column and then freed from the column in a relatively pure form. The fused peptide is then removed by enzymatic activity. In addition, peptide can be purified using immunoaffinity columns or Ni-NTA columns. General techniques are further described in, for example, R. Scopes, Peptide Purification: Principles and Practice, Springer-Verlag: N.Y. (1982); Deutscher, Guide to Peptide Purification, Academic Press (1990); U.S. Pat. No. 4,511,503; S. Roe, Peptide Purification Techniques: A Practical Approach (Practical Approach Series), Oxford Press (2001); D. Bollag, et al., Peptide Methods, Wiley-Lisa, Inc. (1996); A K Patra et al., Peptide Expr Purif, 18(2): p/182-92 (2000); and R. Mukhija, et al., Gene 165(2): p. 303-6 (1995). See also, for example, Ausubel, et al. (1987 and periodic supplements); Deutscher (1990) "Guide to Peptide Purification," Methods in Enzymology vol. 182, and other volumes in this series; Coligan, et al. (1996 and periodic Supplements) Current Protocols in Peptide Science Wiley/Greene, NY; and manufacturer's literature on use of peptide purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See also, for example., Hochuli (1989) Chemische Industrie 12:69-70; Hochuli (1990) "Purification of Recombinant Peptides with Metal Chelate Absorbent" in Setlow (ed.) Genetic Engineering, Principle and Methods 12:87-98, Plenum Press, NY; and Crowe, et al. (1992) QIAexpress: The High Level Expression & Peptide Purification System QIAGEN, Inc., Chatsworth, Calif.

Detection of the expressed peptide is achieved by methods known in the art and includes, for example, radioimmunoassays, Western blotting techniques or immunoprecipitation.

The recombinantly produced and expressed peptide can be recovered and purified from the recombinant cell cultures by numerous methods, for example, high performance liquid chromatography (HPLC) can be employed for final purification steps, as necessary.

Certain peptides expressed in this invention may form insoluble aggregates ("inclusion bodies"). Several protocols are suitable for purification of peptides from inclusion bodies. For example, purification of inclusion bodies typically involves the extraction, separation and/or purification of inclusion bodies by disruption of the host cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension is typically lysed using 2-3 passages through a French Press. The cell suspension can also be homogenized using a Polytron (Brinknan Instruments) or sonicated on ice. Alternate methods of lysing bacteria are apparent to those of skill in the art (see, e.g., Sambrook et al., supra; Ausubel et al., supra).

If necessary, the inclusion bodies can be solubilized, and the lysed cell suspension typically can be centrifuged to remove unwanted insoluble matter. Peptides that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Although guanidine hydrochloride and similar agents are denaturants, this denaturation is not irreversible and renaturation may occur upon removal (by dialysis, for example) or dilution of the denaturant, allowing re-formation of immunologically and/or biologically active peptide. Other suitable buffers are known to those skilled in the art.

Alternatively, it is possible to purify the recombinant peptides from the host periplasm. After lysis of the host cell, when the recombinant peptide is exported into the periplasm of the host cell, the periplasmic fraction of the bacteria can be isolated by cold osmotic shock in addition to other methods known to those skilled in the art. To isolate recombinant peptides from the periplasm, for example, the bacterial cells can be centrifuged to form a pellet. The pellet can be resuspended in a buffer containing 20% sucrose. To lyse the cells, the bacteria can be centrifuged and the pellet can be resuspended in ice-cold 5 mM $MgSO_4$ and kept in an ice bath for approximately 10 minutes. The cell suspension can be centrifuged and the supernatant decanted and saved. The recombinant peptides present in the supernatant can be separated from the host peptides by standard separation techniques well known to those of skill in the art.

An initial salt fractionation can separate many of the unwanted host cell peptides (or peptides derived from the cell culture media) from the recombinant peptide of interest. One such example can be ammonium sulfate. Ammonium sulfate precipitates peptides by effectively reducing the amount of water in the peptide mixture. Peptides then precipitate on the basis of their solubility. The more hydrophobic a peptide is, the more likely it is to precipitate at lower ammonium sulfate concentrations. A typical protocol includes adding saturated ammonium sulfate to a peptide solution so that the resultant ammonium sulfate concentration is between 20-30%. This concentration will precipitate the most hydrophobic of peptides. The precipitate is then discarded (unless the peptide of interest is hydrophobic) and ammonium sulfate is added to the supernatant to a concentration known to precipitate the peptide of interest. The precipitate is then solubilized in buffer and the excess salt removed if necessary, either through dialysis or diafiltration. Other methods that rely on solubility of peptides, such as cold ethanol precipitation, are well known to those of skill in the art and can be used to fractionate complex peptide mixtures.

The molecular weight of a recombinant peptide can be used to isolated it from peptides of greater and lesser size using ultrafiltration through membranes of different pore size (for example, Amicon or Millipore membranes). As a first step, the peptide mixture can be ultrafiltered through a membrane with a pore size that has a lower molecular weight cut-off than the molecular weight of the peptide of interest. The retentate of the ultrafiltration can then be ultrafiltered against a membrane with a molecular cut off greater than the molecular weight of the peptide of interest. The recombinant peptide will pass through the membrane into the filtrate. The filtrate can then be chromatographed as described below.

Recombinant peptides can also be separated from other peptides on the basis of its size, net surface charge, hydrophobicity, and affinity for ligands. In addition, antibodies raised against peptides can be conjugated to column matrices and the peptides immunopurified. All of these methods are well known in the art. It will be apparent to one of skill that chromatographic techniques can be performed at any scale and using equipment from many different manufacturers (e.g., Pharmacia Biotech).

Renaturation and Refolding

Insoluble peptide can be renatured or refolded to generate secondary and tertiary peptide structure conformation. Peptide refolding steps can be used, as necessary, in completing configuration of the recombinant product. Refolding and renaturation can be accomplished using an agent that is known in the art to promote dissociation/association of peptides. For example, the peptide can be incubated with dithiothreitol followed by incubation with oxidized glutathione disodium salt followed by incubation with a buffer containing a refolding agent such as urea.

Recombinant peptide can also be renatured, for example, by dialyzing it against phosphate-buffered saline (PBS) or 50 mM Na-acetate, pH 6 buffer plus 200 mM NaCl. Alternatively, the peptide can be refolded while immobilized on a column, such as the Ni NTA column by using a linear 6M-1M urea gradient in 500 mM NaCl, 20% glycerol, 20 mM Tris/HCl pH 7.4, containing protease inhibitors. The renaturation can be performed over a period of 1.5 hours or more. After renaturation the peptides can be eluted by the addition of 250 mM immidazole. Immidazole can be removed by a final dialyzing step against PBS or 50 mM sodium acetate pH 6 buffer plus 200 mM NaCl. The purified peptide can be stored at 4.degree. C. or frozen at −80.degree. C.

Other methods include, for example, those that may be described in M H Lee et al., Peptide Expr. Purif., 25(1): p. 166-73 (2002), W. K. Cho et al., J. Biotechnology, 77(2-3): p. 169-78 (2000), Ausubel, et al. (1987 and periodic supplements), Deutscher (1990) "Guide to Peptide Purification," Methods in Enzymology vol. 182, and other volumes in this series, Coligan, et al. (1996 and periodic Supplements) Current Protocols in Peptide Science Wiley/Greene, NY, S. Roe, Peptide Purification Techniques: A Practical Approach (Practical Approach Series), Oxford Press (2001); D. Bollag, et al., Peptide Methods, Wiley-Lisa, Inc. (1996).

V. Recombinant Polypeptides

The present invention provides for the production of recombinant peptides of interest in bacterial host expression systems. Examples of recombinant polypeptides that can be used in the present invention include polypeptides derived from prokaryotic and eukaryotic organisms. Such organisms include organisms from the domain Archea, Bacteria, Eukarya, including organisms from the Kingdom Protista, Fungi, Plantae, and Animalia.

Types of peptides that can be utilized in the present invention, in addition to the proteins and peptides described above, include non-limiting examples such as enzymes, which are responsible for catalyzing the thousands of chemical reactions of the living cell; keratin, elastin, and collagen, which are important types of structural, or support, peptides; hemoglobin and other gas transport peptides; ovalbumin, casein, and other nutrient molecules; antibodies, which are molecules of the immune system; peptide hormones, which regulate metabolism; and peptides that perform mechanical work, such as actin and myosin, the contractile muscle peptides.

Other specific non-limiting polypeptides include molecules such as, e.g., renin, a growth hormone, including human growth hormone; bovine growth hormone; growth hormone releasing factor; parathyroid hormone; thyroid stimulating hormone; lipopeptides; .alpha.1-antitrypsin;

insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Peptide C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial peptide, such as beta-lactamase; Dnase; inhibin; activin; vascular endothelial growth factor (VEGF); receptors for hormones or growth factors; integrin; peptide A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-.beta.; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-.beta.1, TGF-.beta.2, TGF-.beta.3, TGF-.beta.4, or TGF-.beta.5; insulin-like growth factor-I and -II (IGF-I and IGF-II); des(1-3)-IGF-I (brain IGF-I), insulin-like growth factor binding peptides; CD peptides such as CD-3, CD-4, CD-8, and CD-19; erythropoietin; osteoinductive factors; immunotoxins; a bone morphogenetic peptide (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane peptides; decay accelerating factor; viral antigen such as, for example, a portion of the AIDS envelope; transport peptides; homing receptors; addressins; regulatory peptides; antibodies; and fragments of any of the above-listed polypeptides.

The recombinant peptides to be expressed by according to the present invention can be expressed from polynucleotides in which the target polypeptide coding sequence is operably attached to transcription and translation regulatory elements to form a functional gene from which the host cell can express the peptide or peptide. The coding sequence can be a native coding sequence for the target polypeptide, if available, but will more preferably be a coding sequence that has been selected, improved, or optimized for use in the selected expression host cell: for example, by synthesizing the gene to reflect the codon use bias of a *Pseudomonas* species such as *Pseudomonas fluorescens*. The gene(s) that result will have been constructed within or will be inserted into one or more vector, which will then be transformed into the expression host cell. Nucleic acid or a polynucleotide said to be provided in an "expressible form" means nucleic acid or a polynucleotide that contains at least one gene that can be expressed by the selected bacterial expression host cell.

Extensive sequence information required for molecular genetics and genetic engineering techniques is widely publicly available. Access to complete nucleotide sequences of mammalian, as well as human, genes, cDNA sequences, amino acid sequences and genomes can be obtained from GenBank at the URL address http://www.ncbi.nlm.nih.gov/Entrez. Additional information can also be obtained from GeneCards, an electronic encyclopedia integrating information about genes and their products and biomedical applications from the Weizmann Institute of Science Genome and Bioinformatics (http://bioinformatics.weizmann.ac.il/cards/), nucleotide sequence information can be also obtained from the EMBL Nucleotide Sequence Database (http://www.ebi.ac.uk/embl/) or the DNA Databank or Japan (DDBJ, http://www.ddbj.nig.ac.jp/; additional sites for information on amino acid sequences include Georgetown's peptide information resource website (http://www-nbrf.georgetown.edu/pir/) and Swiss-Prot (http://au.expasy.org/sprot/sprot-top.html).

The present invention is explained in greater detail in the Examples that follow. These examples are intended as illustrative of the invention and are not to be taken are limiting thereof.

EXAMPLES

Materials and Methods

Unless otherwise noted, standard techniques, vectors, control sequence elements, and other expression system elements known in the field of molecular biology are used for nucleic acid manipulation, transformation, and expression. Such standard techniques, vectors, and elements can be found, for example, in: Ausubel et al. (eds.), *Current Protocols in Molecular Biology* (1995) (John Wiley & Sons); Sambrook, Fritsch, & Maniatis (eds.), *Molecular Cloning* (1989) (Cold Spring Harbor Laboratory Press, NY); Berger & Kimmel, *Methods in Enzymology* 152: Guide to Molecular Cloning Techniques (1987) (Academic Press); and Bukhari et al. (eds.), *DNA Insertion Elements, Plasmids and Episomes* (1977) (Cold Spring Harbor Laboratory Press, NY).

Unless noted otherwise, PCR reactions were performed using a PTC225 thermocycler (MJ Research, South San Francisco, Calif., USA) according to the protocol in Table 6.

TABLE 6

| PCR protocol | | | | | |
|---|---|---|---|---|---|
| Reaction Mix (100 µL total volume) | | Thermocycling Steps | | | |
| 10 µL 10X Herculase buffer * | | Step 1 | 1 Cycle | 2 min. | 94° C. |
| | | Step 2 | 35 Cycles | 30 sec. | 94° C. |
| 2 µL 10 mM dNTPs * | | | | 30 sec. | 55° C. |
| 0.25 ng Each Primer | | | | 1 min. | 68° C. |
| 1-5 ng Template DNA | | Step 3 | 1 Cycle | 10 min. | 70° C. |
| 1 µL Herculase DNA Polymerase * | | Step 4 | 1 Cycle | Maintain | 4° C. |
| Remainder Distilled De-ionized H$_2$O (ddH$_2$O) | | | | | |

* (Stratagene, La Jolla, Ca. USA, hereinafter "Stratagene")

Strains and Plasmids

Strains utilized in the present Examples are described in Table 7. Plasmids were prepared using the QIAprep Spin Miniprep Kit from Qiagen; Valencia, Calif.) and transformed into *Pseudomonas fluorescens* DC283 or DC388 by electroporation of freshly-plated cells as follows. See for example, Enderle et al. (1998) "Electroporation of freshly plated *Escherichia coli* and *Pseudomonas aeruginosa* cells," Biotechniques 25: 954-958. Cells were scraped off an LB-agar plate with an inoculation loop, washed 3 times in 500 µl Milli-Q water, and resuspended in 40 µl Milli-Q water. One µl of plasmid DNA was mixed with 40 µl of cells and transferred to an ice-cold electroporation cuvette. Electroporation was performed with a Gene Pulser II (Bio-Rad, Hercules, Calif.) with a field strength of 2.25 kV/cm. Cells were immediately transferred to 1 ml SOC medium (Invitrogen; Carlsbad, Calif.), incubated for 1-1.5 hours at 30° C., and subsequently spread on selective agar plates (M9 glucose plus uracil). Agar plates were incubated at 30° C.

TABLE 7

Strains used in this report

| Strain name | Genotype |
|---|---|
| DC283 | ΔpyrF ΔproC ΔbenAB lsc::lacI$^{Q1}$ |
| DC388 | ΔpyrF ΔproC ΔbenAB lsc::lacI$^{Q1}$ ΔmtlDYZ |
| DC389 | ΔpyrF ΔproC ΔbenAB lsc::lacI$^{Q1}$ ΔmtlDYZ + pDOW1365-1 |
| DC390 | ΔpyrF ΔproC ΔbenAB lsc::lacI$^{Q1}$ ΔmtlDYZ + pDOW1365-1 pDOW1339 |
| MB214 | MB101 lacI lacZYA |

Growth Experiments

All percentage concentrations for glycerol are expressed as v/v and those for glucose and mannitol as w/v. Growth experiments were performed in 1 L bottom-baffled shake-flasks containing 200 ml of mineral salts medium with 5 g/L yeast extract and trace elements. Standard medium contained 9.5% glycerol, which corresponds to a concentration of 1.3 M. For some experiments, the glycerol concentration was reduced to 2% (=274 mM) or 5% (=685 mM). When glucose was used as a carbon source, a solution of 25% glucose in shake-flask medium without glycerol was filter-sterilized and added to autoclaved medium to give a final concentration of 5% (=278 mM) or 12.5% (=694 mM) glucose. If needed, uracil (750 µg/ml) was added to the shake-flask medium. Four mL of an overnight culture of the strain grown in M9 glucose (plus uracil 250 µg/ml if required) was used as inoculum for shake-flasks. Growth was monitored by measuring the optical density of the cultures at 600 nm at defined time intervals in 1-cm plastic cuvettes with an Eppendorf BioPhotometer (Eppendorf AG; Hamburg, Germany). Induction of the mannitol promoter was typically performed at 24 hours elapsed fermentation time by addition of 1% (=55 mM) mannitol from a 20% stock solution.

Cultivation of DC390 in 20-Liter Fermentors

Strain DC390 was grown in standard aerated 20-L research fermentation vessels in a mineral salts medium described by Risenberg et al. (1991) "High cell density cultivation of *Escherichia coli* at controlled specific growth rate," J. Biotech. 20(1):17-27, with slight modification. Cultures were grown for 72 h at 32° C.; the pH was maintained at 6.5 through the addition of aqueous ammonia. Agitation and sparged air flow rates were initially increased to control dissolved oxygen at a positive level but were fixed at maximum levels when these were reached. Glucose or glycerol was fed throughout the fermentation process to maintain a slight excess. The fed-batch high density fermentation process was divided into an initial growth phase of approximately 24 h and a gene expression (induction) phase in which mannitol at 1% (w/v) concentration was added to initiate recombinant gene expression at a target cell density of 170 OD units at 575 nm. Optical densities and cell fluorescence were monitored over time. Final cell densities varied depending on the carbon source.

Fluorescence Analyses

Fluorescence of cultures was measured with a Spectramax Gemini microplate fluorimeter (Molecular Devices Corporation; Sunnyvale, Calif.) using the following settings: excitation 485 nm, emission 538 nm, bandpass filter 530 nm. Before analysis, the optical density ($OD_{600}$) of samples was measured in 1-cm cuvettes as described above. Samples were diluted to $OD_{600}$=5 with shake-flask medium in Eppendorf tubes and then to $OD_{600}$=1 with water directly in the 96-well microplate. Diluted shake-flask medium (1:5) was used as a blank. The optical density at 600 nm of the samples in the 96-well plate was measured with a Spectramax Plus microplate spectrophotometer (Molecular Devices Corporation; Sunnyvale, Calif.), and fluorescence values were reported as RFUs—relative fluorescence units.

For flow cytometry, culture samples were fixed by formaldehyde as follows: 1 mL of cells were pelleted and resuspended in phosphate-buffered saline (PBS) (pH 7.2). In the fume hood, 37% formaldehyde (stock concentration) was added to a concentration of 2%. Cells were incubated for 5 min at room temperature, then centrifuged and resuspended in PBS for a total of three times. The $OD_{600}$ was adjusted to 0.01 and cells were stored at 4° C. until analysis. All washes were collected as hazardous waste. Flow cytometry analyses were performed by Cytometry Research, San Diego, Calif. Data were plotted using FCS Express2 software (DeNovo Software; Thornhill, Ontario, Canada).

Analysis of Mannitol, Glycerol, and Glucose Concentration

The concentration of mannitol, glycerol, and glucose in culture broth was determined with a Dionex ion chromatograph fitted with a CarboPac PA10 analytical column and an ED50 pulsed amperometric detector (PAD) (Dionex Corporation; Sunnyvale, Calif.). Cells and culture broth were separated by centrifugation, and supernatant samples were stored at −20° C. until used. Samples were diluted several thousand-fold with water to an estimated concentration of about 10 µg/ml and injected onto the column (injection volume 25 µl) with an auto-sampler. The column was equilibrated with 18 mM sodium hydroxide in water. At a flow rate of 1 ml/min, run conditions were as follows: 18 mM NaOH for 10 min; increase to 100 mM NaOH within 1 min; 100 mM NaOH for 1 min; 18 mM NaOH for 8 min to condition the column. Approximate retention times were as follows: Glycerol 2.2 min; mannitol 3.4 min; glucose 12.8 min. Concentrations were calculated based on standards of known concentrations.

Example 1

Identification of the mtl Operon in Various Pseudomonads

Figure 3:
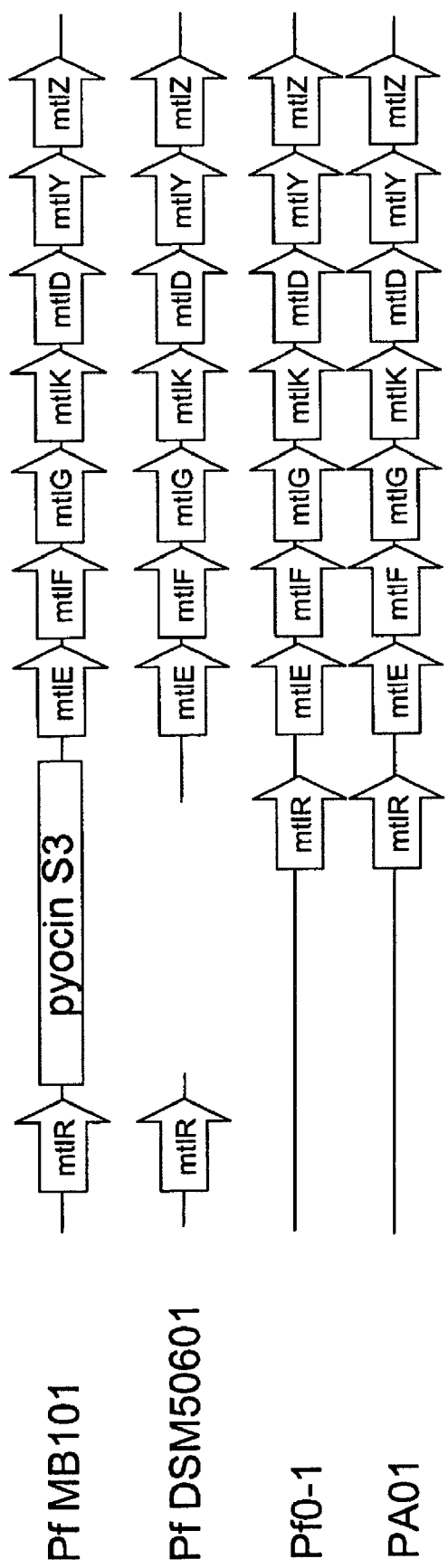
FIG. 3 illustrates a comparison of the mannitol operon in MB101 and other Pseudomonads. The figure shows an alignment of the mtl operon in four different *Pseudomonas* strains, *P. fluorescens* MB101, *P. fluorescens* DSM50601, *P. fluorescens* Pf0-1, and *P. aeruginosa* PA0-1. The mtlR gene, encoding the transcriptional activator of the mtl operon, is located directly upstream of the mtl operon in all cases except in MB101, where it occurs several kB upstream and DSM50601, where it occurs at an unknown place in the genome.

A BLAST search of the *P. fluorescens* MB101 genome in the ERGO database, using the DSM50106 mtlE sequence as described by Brunker et al. (1998) "Structure and function of the genes involved in mannitol, arabitol, and glucitol utilization from *Pseudomonas fluorescens* DSM50106," Gene 206 (1):117-126, showed that MB101 has an mtl operon that is similar to the one described in DSM50106, starting with RXF01195 (mtlE). A gene alignment of the mtl operon in four different *Pseudomonas* strains, *P. aeruginosa* PA0-1, *P. fluorescens* DSM50106, *P. fluorescens* Pf0-1, and *P. fluorescens* MB101, is shown in FIG. 3. There are two types of gene arrangement—one where the transcriptional activator gene, mtlR, is located directly upstream of the mtl operon, and one where mtlR is not present directly upstream of the mtl operon, which is the case for MB101 and DSM50106.

A sequence alignment between the regions directly upstream of the mtlE ATG start codon in MB101, DSM50106, *P. fluorescens* Pf0-1, and *P. aeruginosa* PA0-1 is shown in FIG. 4. Perfectly conserved sequences that match the −35 and −10 promoter region consensus sequence were found in the four strains, which supports the conclusion that the region serves as the promoter for the mtl operon. In addition, two perfectly conserved regions were found, one of 15 bp, upstream of the −35 region, and one of 14 bp downstream of the −10 region.

Example 2

Cloning of the Promoter Region for the mtl Operon

Figure 5:
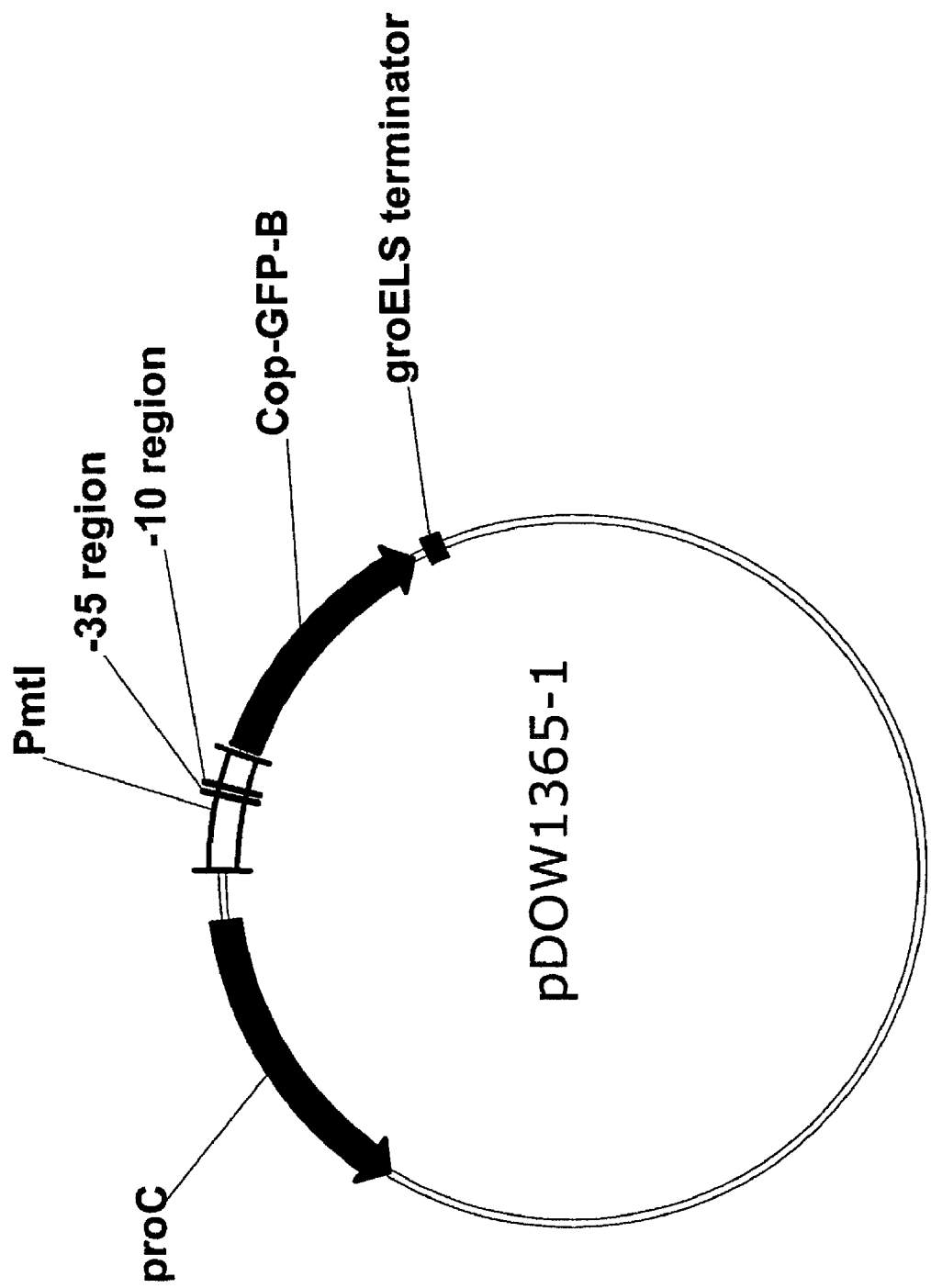
FIG. 5 illustrate the cloning of mtl promoter fragment in front of the CopGFP reporter gene. A 299 bp region upstream of the MB101 mtlE gene (SEQ ID NO:9) was cloned by PCR amplification with primers mtlE3 SEQ ID NO:14 and mtlE4 (SEQ ID NO:15) (see Table 8), to make pDOW1365-1, using Herculase thermostable DNA polymerase (Stratagene) and MB214 (a strain derived from MB101) genomic DNA as a template.

A 299 bp region upstream of the MB101 mtlE gene (SEQ ID NO:9, Table 3) was amplified by PCR using primers mtlE3 (5'-ATATGAGCTCGAGCGTGGGAACGATCAAGTGT-3'-SEQ ID NO:14) and mtlE4 (5'-ATATCCGCGGTTC-CGCGCCCAGAGGGCTAC-3'SEQ ID NO:15), (see Table 8) and cloned in front of the CopGFP reporter gene to make pDOW1365-1 (FIG. 5). The cloned region contains all of the sequences that are conserved between DSM50106 and MB101 as well as sequences farther upstream. Two pDOW1365-1 clones were sequenced; one (pDOW1365-1) had the same sequence as the genome reference (sequenced by The Dow Chemical Company), whereas the other had fourteen differences between the clone and the reference sequence. Since this large number of changes is unlikely to result solely from the error-prone PCR amplification process, we speculate that the DNA polymerase apparently switched templates among the four and a half direct repeats in the upstream region between cycles in the PCR amplification. The sequence of the repeats varies slightly, leading to sequence diversity in the PCR product.

A promoter region of 126 bp from the same region (SEQ ID NO: 11, Table 3) was amplified by PCR using primers mtlE5 (5'-ATATGAGCTCTAAGCGTGCTCCCAAG-GATTTGTCA-3' SEQ ID NO:16) and mtlE4, and cloned in front of the CopGFP gene to make pDOW1369 (map not shown).

The 203 bp region between mtlR and mtlE in *P. fluorescens* Pf0-1 (SEQ ID NO: 10) was cloned by PCR amplification using primers mtlE6 (SEQ ID NO:17) and mtlE7 (SEQ ID NO:18) (Table 8) and inserted upstream of the CopGFP reporter gene, resulting in pDOW1370-7 (map not shown). The sequence of the cloned promoter region was the same as the reference sequence obtained from the ERGO database.

A promoter region of 147 bp from the same region (SEQ ID NO:12, Table 3) was amplified by PCR using primers mtlE9 (5'-ATATGAGCTCACGAGTGCAAAAAAGTATCAG TAAG 3' SEQ ID NO:19) and mtlE4 (Table 8), and cloned in front of the CopGFP gene to make pDOW1377 (map not shown).

A promoter region of 77 bp from the same region (SEQ ID NO:13, Table 3) was amplified by PCR using primers mtlE9 and mtlE11 (5'-ATATCCGCGGGTGCGTTGATTACA GCCTTCAAA 3' SEQ ID NO:20) (Table 8), and cloned in front of the CopGFP gene to make pDOW1378 (map not shown).

Figure 6:
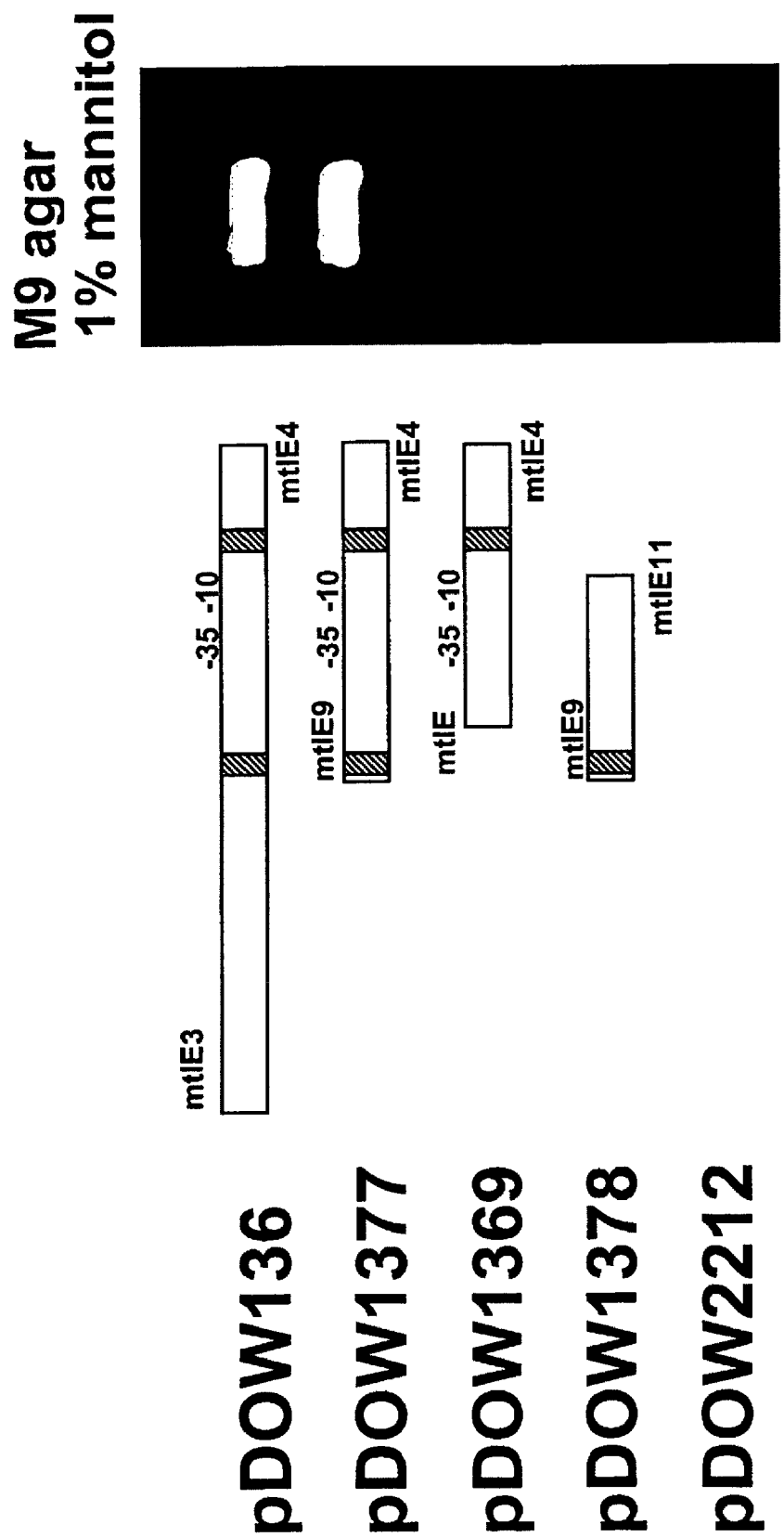
FIG. 6 illustrates the comparison of activity of various fragments from the region upstream of mtlE. Strain DC283ΔmtlDYZ, carrying either pDOW1365-1, pDOW1377, pDOW1369, pDOW1378, or pDOW2212 (with no CopGFP gene), were patched on M9 agar plates containing 1% mannitol with supplemental uracil. Induction of the fluorescent protein was determined by exposure to blue light. The two 15-bp regions of homology between the four strains (see FIG. 4) are indicated by hatched boxes. The −35 and −10 regions are indicated, and the primers used to clone each sequence are noted at the edge of the open box which indicates the region cloned upstream of the CopGFP reporter gene.

To measure relative promoter activity on agar plates, DC283, a uracil and proline auxotrophic mutant of *P. fluorescens* MB101, was transformed with the plasmids and streaked on a M9 plates containing 250 µg/mL uracil, 100 µM FeCl$_3$ (to suppress production of fluorescent pyoverdine which is produced by cells when iron-limited), and various carbon sources and incubated at 30° C. Colonies were examined by a blue light transilluminator (Dark Reader, Clare Chemical Research). Only the 299 bp MB101 fragment in pDOW1365-1 or pDOW1365-2 and the 147 bp fragment in pDOW1377 induced the CopGFP gene in the presence of mannitol (See Table 9 and FIG. 6)—the other fragments did not express any CopGFP under any of the conditions tested. All of the fragments contained the −35 and −10 promoter regions. When mannitol was supplemented with 1% glycerol or glucose, the pDOW1365-1 construct still produced CopGFP, which indicated that the promoter was not catabolite-repressed by either carbon source. The pDOW1365-1 promoter had no activity when 1% glycerol or 1% glucose was the sole carbon source. However, the promoter was active when glycerol was used at levels of 5% and 9.5% (Table 9), indicating that glycerol may act as a fortuitous inducer of the mtl promoter.

TABLE 8

Oligonucleotides with engineered restriction sites are underlined.

| oligo-nucleo-tide | Sequence | SEQ. ID. |
|---|---|---|
| mtlE3 | 5'ATAT<u>GAGCTC</u>GAGCGTGGGAACGATCAAGTGT | 14 |
| mtlE4 | 5'ATAT <u>CCGCGG</u>TTCCGCGCCCAGAGGGCTAC | 15 |
| mtlE5 | 5'ATAT<u>GAGCTC</u>TAAGCGTGCTCCCAAGGATTTGTCA | 16 |
| mtlE6 | 5'ATAT<u>GAGCTC</u>TGAGCAGGAAAATCTGTACG | 17 |
| mtlE7 | 5'ATAT<u>CCGCGG</u>GGGGGCAGAAGGACAGTTAT | 18 |
| mtlE9 | 5'ATAT<u>GAGCTC</u>ACGAGTGCAAAAAAGTATCAGTAAG | 19 |
| mtlE11 | 5'ATAT<u>CCGCGG</u>GTGCGTTGATTACAGCCTTCAAA | 20 |
| man1 | 5'GCCGACAAGGTAGTGGTGCTCAACA | 21 |
| man2 | 5'TGCCCGCTCGCCTCACATCGGGAAATACTC | 22 |
| man3 | 5'GAGTATTTCCCGATGTGAGGCGAGCGGGCA | 23 |
| man4 | 5'ACCGATAGTGCCACCGCTCTGGTAG | 24 |
| H3seq | 5'GTCCTGCAATTTCAGCCCGA | 25 |
| man5 | 5'TGTTCGACGAACCGCTGTCCA | 26 |
| man6 | 5'TTCAATGGTCCCCCCGGTCATTTCATA | 27 |

TABLE 9 mtl promoter activity on various carbon sources

| Strain (size of region upstream of mtlE, host) | 1% mtl | 1% glyc-erol | 1% glu | 1% mtl glycerol | 1% mtl glu | 10% glyc-erol |
|---|---|---|---|---|---|---|
| pDOW1365-1 (299 bp MB101) | + | − | − | + | + | + |
| pDOW1365-1-2 (299 bp MB101) | + | − |  | + | + | Nd |
| pDOW1369 (126 bp MB101) | − | nd | nd | − | nd | − |
| pDOW1377 (147 bp MB101) | + | nd | nd | nd | nd | Nd |
| pDOW1378 (77 bp MB101) | − | nd | nd | nd | nd | Nd |
| pDOW1370-7 (203 bp Pf0-1) | − | nd | nd | nd | nd | Nd |
| pDOW1361 control (no Cop gene) | − | − | − | − | − | − |

Example 3

Mannitol Induction

Figure 7:
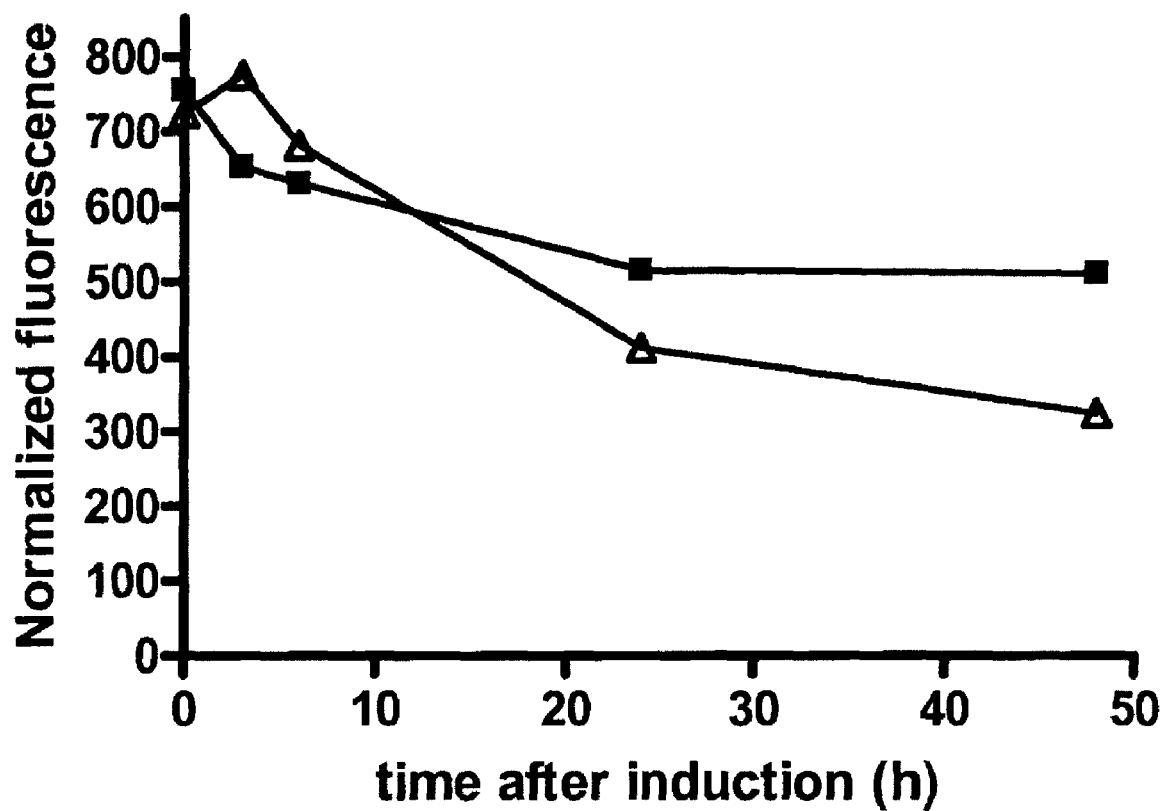
FIG. 7 illustrates the effect of mannitol on expression of CopGFP from Pmtl in a wildtype strain background grown on standard production medium. Strain DC283 pDOW1365-1 was cultivated in shake-flask medium containing 9.5% (v/v) glycerol and uracil supplementation. Mannitol 1% (w/v) was added to one set at 24 h EFT (filled squares) or not added (open triangles). Fluorescence after induction was monitored over time. Fluorescence was measured on samples that were normalized to $OD_{600}=1$.
Figure 8:
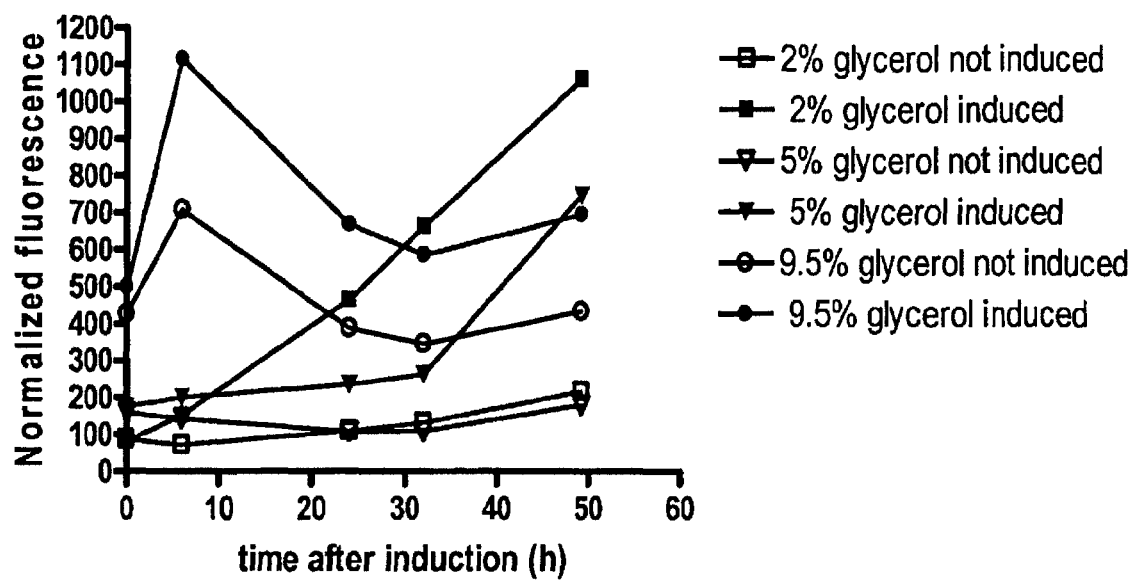
FIG. 8 illustrates the effect of mannitol on expression of CopGFP from Pmtl in a wildtype strain background in medium with various glycerol concentrations. Strain DC283 pDOW1365-1 was cultivated in shake-flask medium containing 2% (squares), 5% (triangles), or 9.5% (circles) glycerol. Cultures were uninduced (open symbols) or induced (closed symbols) with 1% mannitol at 20 h EFT. Fluorescence after induction was monitored over time. Fluorescence was measured on samples that were normalized to $OD_{600}=1$.

Experiments to examine mannitol induction were performed in *Pseudomonas fluorescens* strain DC283, a uracil and proline auxotrophic mutant of *P. fluorescens* MB101. See, for example, J C Schneider et al. (2005) "Auxotrophic markers pyrF and proC can replace antibiotic markers on protein production plasmids in high cell density *Pseudomonas fluorescens* fermentation," Biotech Prog 21:343. Growth experiments with strain DC283/pDOW1365-1 were initially conducted in standard shake-flask medium containing 9.5% glycerol. After cultivation of the cells for about 24 hours, 1% mannitol (55 mM) was added to induce expression of CopGFP, which was followed over time by measuring the fluorescence of the culture. Interestingly, the cells showed a high degree of fluorescence before induction with mannitol, and cell fluorescence did not increase after induction (FIG. 7). Further experiments revealed that the fluorescence level before induction and the inducibility of the mannitol promoter was correlated with the amount of glycerol in the medium. Increasing the glycerol concentration in the shake-flask medium from 2% to 5% to 9.5% resulted in increasing levels of uninduced fluorescence and decreasing levels of induced fluorescence (FIG. 8). CopGFP expression was only immediately inducible by mannitol in medium containing a 2% glycerol concentration. Using these low levels of glycerol is not satisfactory for shake-flask analysis because all of the carbon source is consumed in 24 hours.

Example 4

Deletion of the mtlDYZ Mannitol Degradation Genes in *P. fluorescens*

Figure 9:
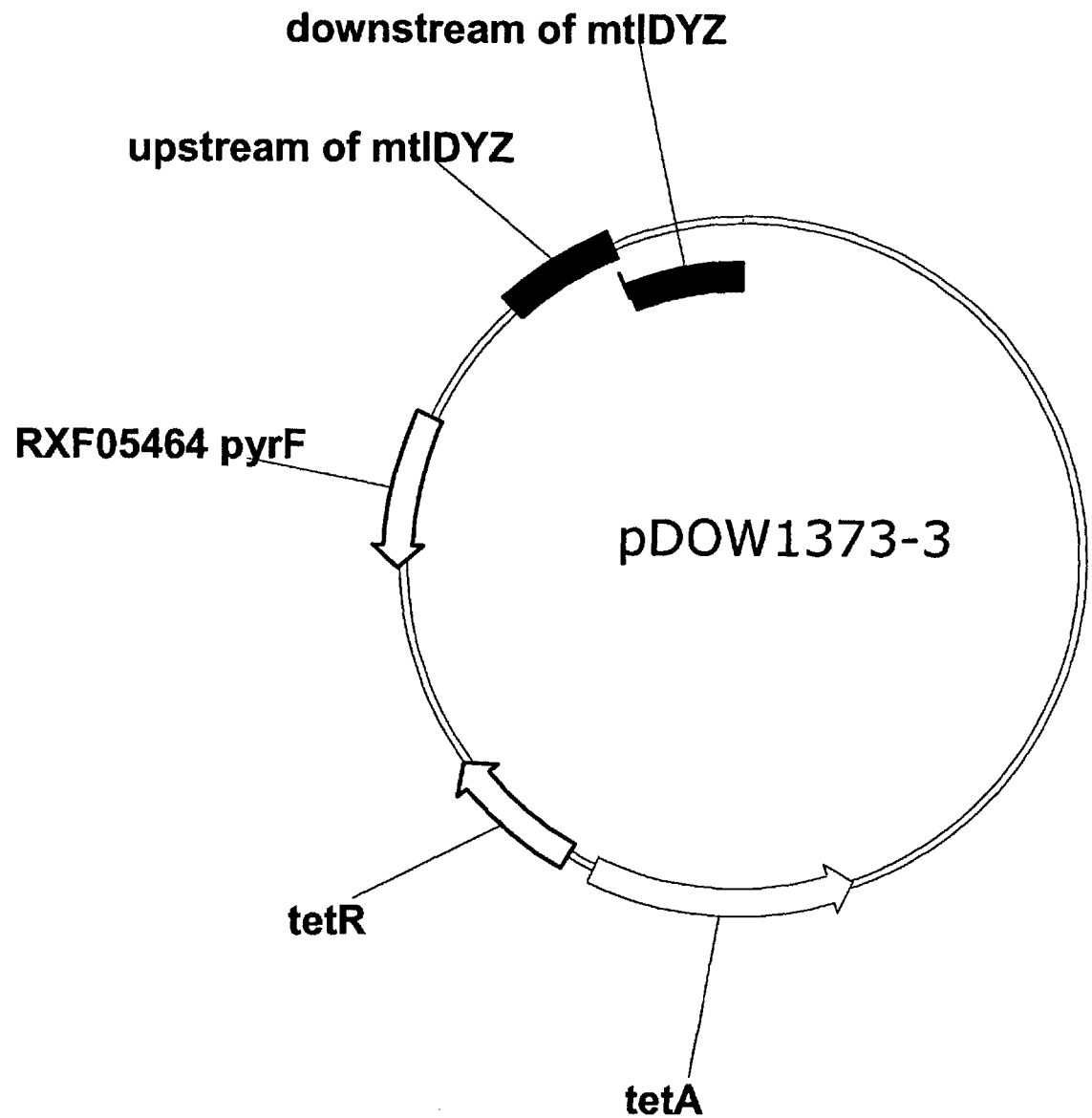
FIG. 9 illustrates a vector map of mtlDYZ deletion vector pDOW1373-3. The vector pDOW1373-3 was designed to delete the mtlDYZ genes by allele exchange mutagenesis. The mtlDYZ flanking regions were amplified using MB214 genomic DNA as a template and joined using the splicing by overlap extension technique, using primers man1 (SEQ ID NO:18) and man2 (SEQ ID NO:19) for the region upstream and man3 SEQ ID NO:20 and man4 SEQ ID NO:21 for the region downstream. Primers man2 and man3 contains complementary overlaps. The joined product was cloned into pDOW1261/SrfI to make pDOW1373-3. Colonies were screened with primer H3seq SEQ ID NO:22 and man4; those with the expected 1170 bp product were sequenced to ensure that no PCR-derived mutations were incorporated.

To prevent mannitol degradation by strain DC283 we deleted three genes (mtlDYZ) from the mannitol operon on the chromosome. The suicide vector pDOW1373-3 (FIG. 9) was designed to delete the mtlDYZ genes by allele exchange mutagenesis. The mtlDYZ flanking regions were amplified using MB214 genomic DNA as a template and joined using the splicing by overlap extension technique, using primers man1 (5'-GCCGACAAGGTAGTGGTGCTCAACA-3') (SEQ ID NO:21) and man2 (5'-TGCCCGCTCGCCTCA-CATCGGGAAATACTC-3') (SEQ ID NO:22) for the region upstream and man3 (GAGTATTTCCCGATGTGAGGC-GAGCGGGCA-3') (SEQ ID NO:23) and man4 (5'-AC-CGATAGTGCCACCGCTCTGGTAG-3') (SEQ ID NO:24) for the region downstream. Primers man2 and man3 contain complementary overlaps. The joined product was cloned into pDOW1261/SrfI to make pDOW1373-3. (FIG. 9). Colonies were screened with primer H3seq (5'-GTCCTG-CAATTTCAGCCCGA-3') (SEQ ID NO:25) and man4; those with the expected 1170 bp product were sequenced to confirm that no PCR-generated mutations had been incorporated.

Plasmid pDOW1373-3 was transformed into strain DC283, in which it cannot replicate independently and integrants into the genome were selected by tetracycline resistance. Transformants with a successful integration of the plasmid into the chromosome either upstream or downstream of the mtlDYZ gene cluster were identified by carrying out PCR amplification. A few upstream and downstream integrants were then cultivated in the absence of tetracycline to enrich for clones that had successfully looped-out the plasmid (with or without mtlDYZ genes) from the chromosome by a second cross-over. Losing the plasmid caused the clones to be resistant to 5'-fluoroorotic acid, which was used in agar cultivation medium to select for clones with the desired genotype. Clones that did not have the plasmid (and the mtlDYZ genes) integrated in the chromosome anymore had their uracil auxotrophy restored. PCR amplification using primers man5 (5'-TGTTCGACGAACCGCTGTCCA-3') (SEQ ID NO:26) and man6 (5'-TTCAATGGTCCCCCCGGTCATTTCATA-3') (SEQ ID NO:27), which lie outside of the region amplified for the allele exchange, resulted in PCR product of the expected size (1308 bp) in several isolated clones, which indicated that the plasmid plus the mtlDYZ genes were successfully deleted from the DC283 chromosome. PCR sequencing of the chromosomal region of interest confirmed that mtlDYZ genes were absent in strain DC283 ΔmtlDYZ (=DC388).

Figure 10:
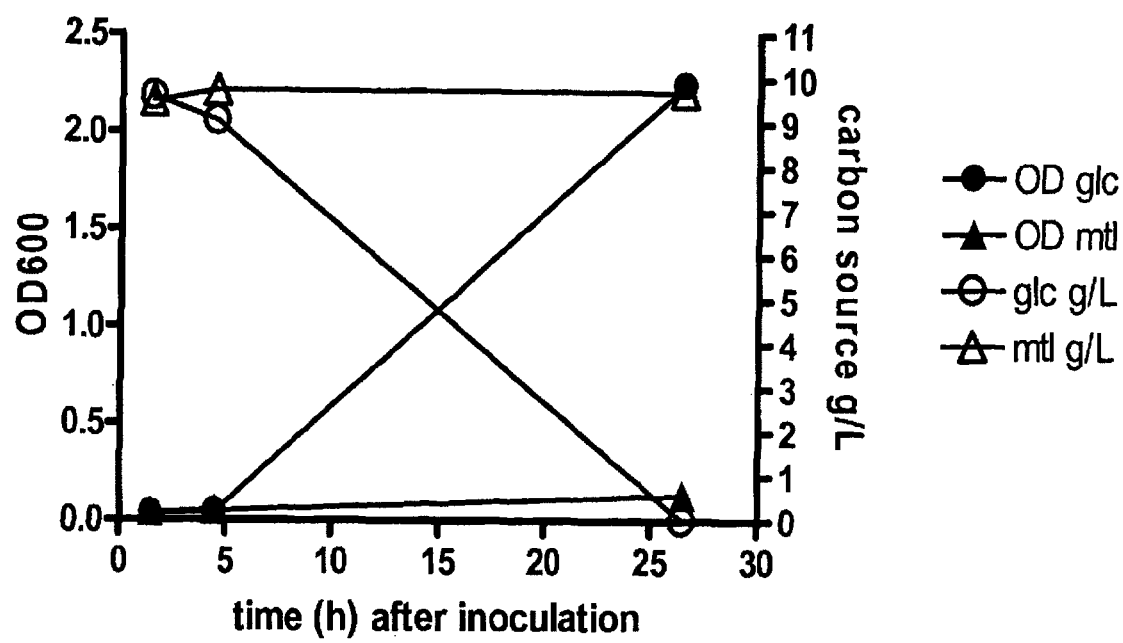
FIG. 10 illustrates growth and carbon source (mannitol or glucose) utilization of strain DC283ΔmtlDYZ. Cultures were grown in M9 medium with 1% carbon source, and supplemented with uracil (250 μg/ml) and proline (250 μg/ml). Glucose (open circle) and mannitol (open triangle) concentrations and optical density at 600 nm (closed triangle for mannitol, closed circle for glucose) after induction were monitored over time.

Strain DC388 was analyzed for growth and carbon metabolism in M9 mineral salts medium supplemented with uracil and proline (250 µg/ml each) and 1% (w/v) glucose or 1% (w/v) mannitol as the sole source of carbon and energy. The mutant grew in medium with glucose to an $OD_{600}$ of about 2.2 within 24 hours and glucose was depleted concomitantly. In contrast, only a minor increase in optical density was observed in medium with mannitol as the sole carbon source, and the mannitol concentration did not decrease over time (FIG. 10). These results demonstrated that the mtlDYZ deletion mutant had the expected phenotype and could not degrade mannitol.

Example 5

Figure 11:
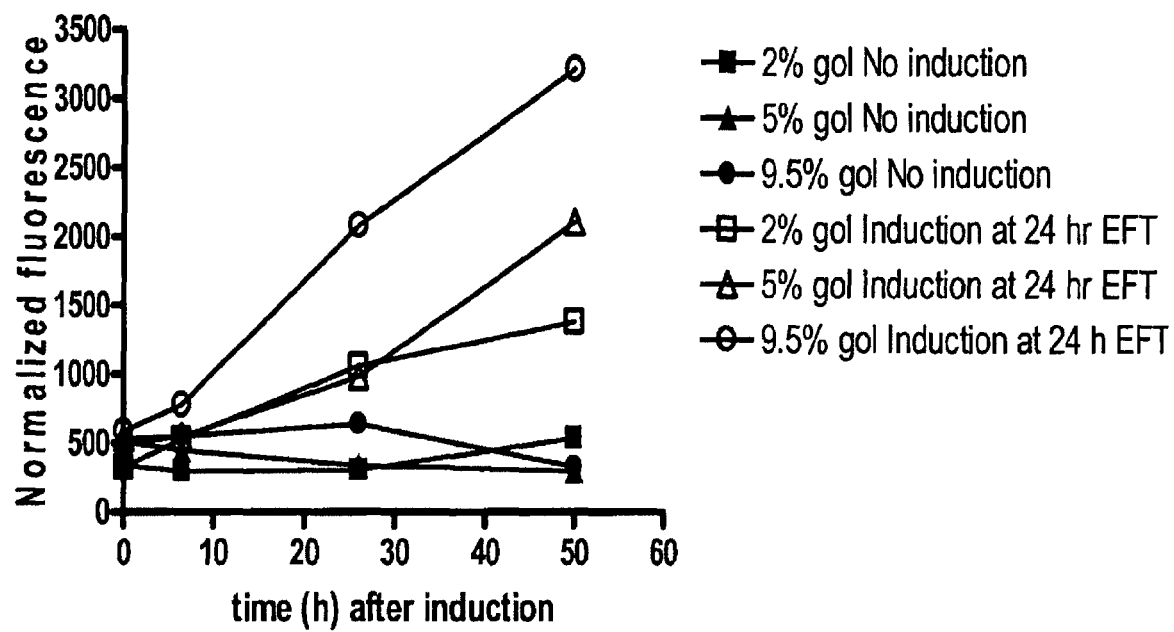
FIG. 11 illustrates the effect of glycerol concentration on expression of CopGFP from Pmtl in the mannitol-degradation-defective strain after induction with 1% mannitol. Strain DC283ΔmtlDYZ/pDOW1365-1 was cultivated in shake-flask medium with an initial concentration of 2% (squares), 5% (triangles), or 9.5% (circles) glycerol with supplemental uracil. Cultures were either induced with 1% mannitol at 22 h EFT (closed symbols) or left uninduced (open symbols). Fluorescence after induction was monitored over time. Fluorescence was measured on samples that were normalized to $OD_{600}=1$.

Mannitol-Induced CopGFP Expression in the mtlDYZ Deletion Mutant Under Various Growth Conditions Plasmid pDOW1365-1 (which carries the CopGFP gene controlled by the 299 bp mtl promoter) was transformed into strain DC283 ΔmtlDYZ. The resulting construct, strain DC389, was tested in shake-flask medium with various concentrations of glycerol (2%, 5%, 9.5%). In the mannitol-degradation-defective strain, mannitol induced CopGFP at all glycerol concentrations (FIG. 11), whereas in the wildtype strain, only cultures that were grown on 2% initial glycerol showed immediate induction (FIG. 7). The amount of promoter activity was positively correlated with the carbon source concentration; the highest induction levels were achieved using 9.5% glycerol. The deletion removed the first steps in mannitol assimilation, therefore the induction of Pmtl by mannitol indicates that mannitol, and not a breakdown product, is the inducer of Pmtl.

Figure 12:
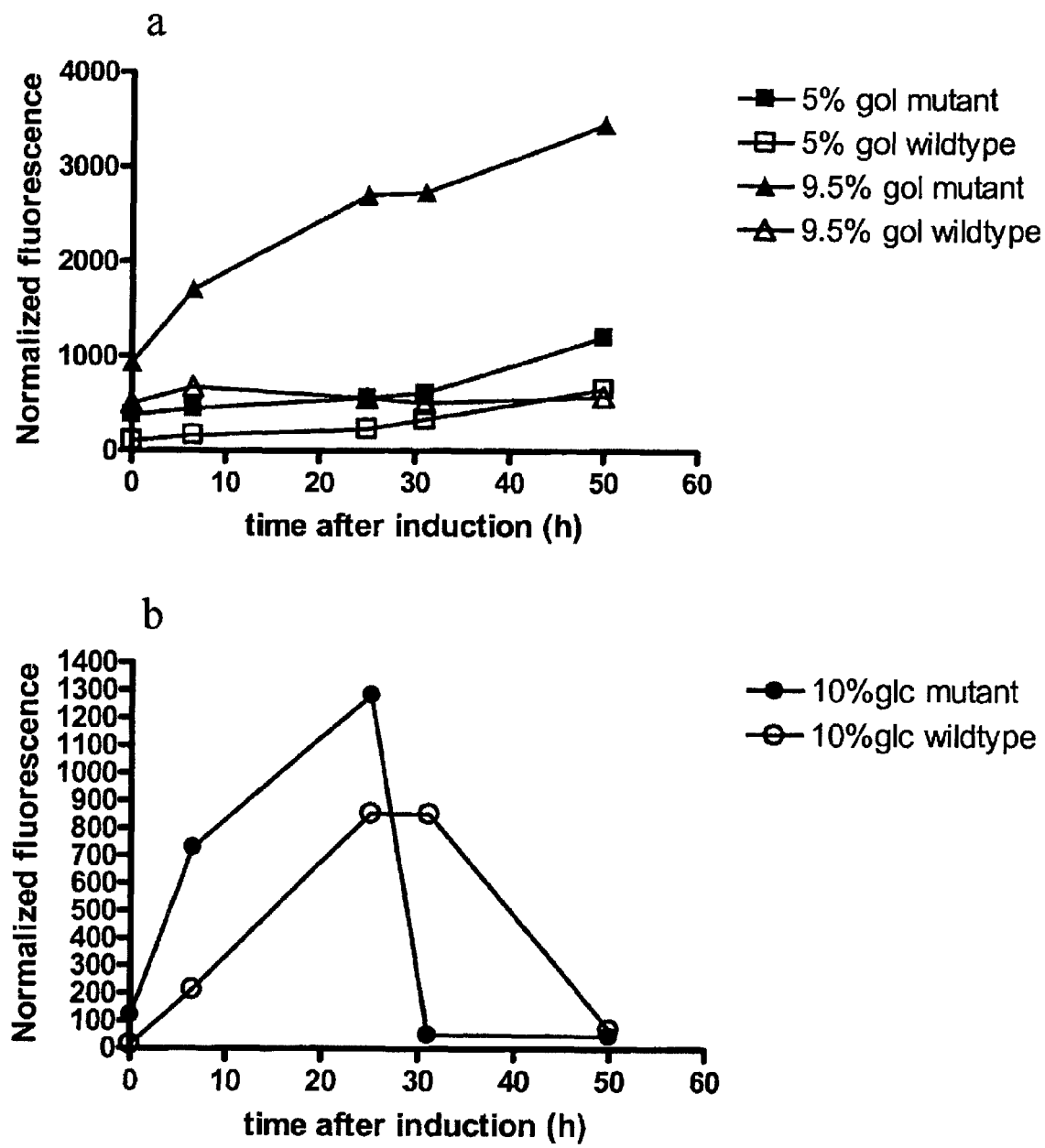
FIG. 12 illustrates comparison of Pmtl activity in the mtlDYZ deletion mutant and wildtype in various carbon sources. Pmtl activity was compared in the mannitol-degradation-defective strain (D283ΔmtlDYZ/pDOW1365-1) (closed symbols) and the wildtype (DC283/pDOW1365-1) (open symbols) in shake-flask medium with initial concentrations of 5% (squares) or 9.5% glycerol (triangles) (a), or 10% glucose (circles) (b). Cultures were induced with 1% mannitol at 24 h EFT and fluorescence after induction was monitored over time. Fluorescence was measured on samples that were normalized to $OD_{600}=1$.

In a side-by-side comparison of the deletion mutant and the wildtype strain it was confirmed that the mutant strain was inducible by mannitol in medium with 9.5% glycerol, whereas the wildtype strain was not (FIG. 12). Mannitol concentration stayed constant in the mutant strain but declined to zero in the wildtype strain (data not shown). The mutant grew to lower $OD_{600}$ which may be attributed to its inability to use mannitol as a carbon source and the higher expression of the CopGFP gene in the mutant, which may place a burden on cell growth. The mutant showed higher pre-induction levels of expression than the wildtype which may result from the inability of the mutant strain to degrade trace amounts of inducers present in the yeast extract.

The mannitol promoter also achieved higher levels of induction when the mutant strain was grown on 10% glucose as a carbon source (FIG. 12b). Glucose-grown cultures experienced a rapid loss in CopGFP activity after 48 hours, which is attributed to acidification of the medium and concomitant death and protein denaturation.

Example 6 mtl Promoter Activity After Induction with Various Mannitol Concentrations

Figure 13:
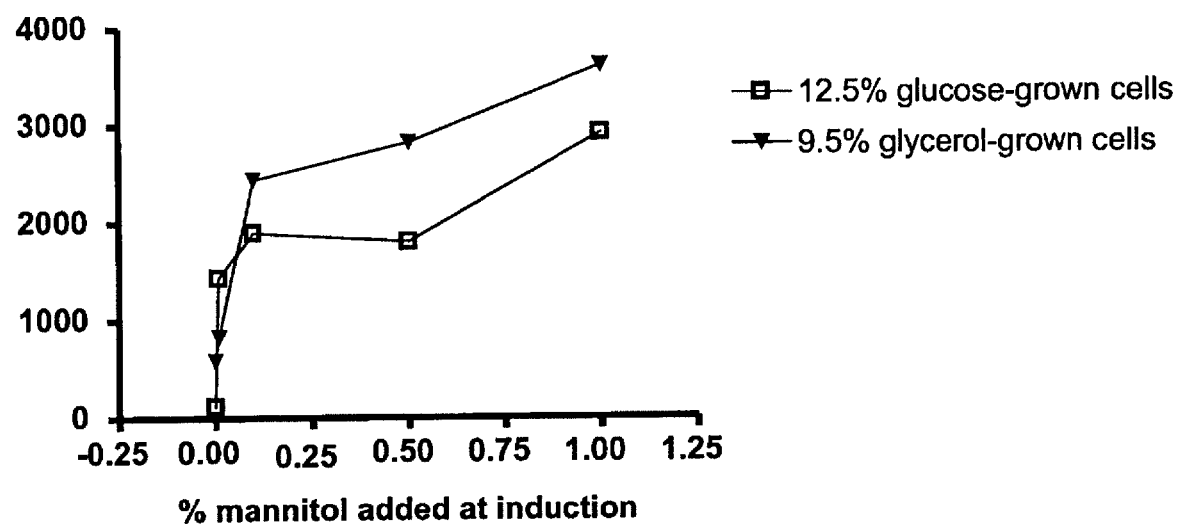
FIG. 13 illustrates Pmtl activity after induction with various concentrations of mannitol. Various amounts of mannitol (0, 0.01%. 0.1%, 0.5%, 1%) were added as an inducer at 25 h EFT to D283ΔmtlDYZ/pDOW1365-1 grown with 9.5% glycerol and supplemental uracil (triangles) or D283ΔmtlDYZ/pDOW1365-1 pDOW1339 grown with 12.5% glucose (squares). Fluorescence after induction was monitored over time on samples that were normalized to $OD_{600}=1$.

To induce CopGFP expression from the mtl promoter, a concentration of 1% (=55 mM) mannitol was added to the culture medium in previous experiments. In this experiment, the mannitol concentration added at 24 hr to glucose-grown or glycerol-grown cultures was varied between 0.01% and 1% to determine if lower inducer concentrations could be used to induce expression. Fluorescence after induction increased with increasing concentration of mannitol (FIG. 13). Mannitol at 0.01% was sufficient to cause an increase in promoter activity in both glycerol-grown and glucose-grown cells, although higher levels were reached at 1% mannitol.

Example 7

Glycerol Induction of the mtl Promoter

In shake-flask experiments, it was observed that both the wildtype and the mutant strain showed background fluorescence before induction in glycerol-containing medium but not in glucose-containing medium. Glycerol shares structural similarities with mannitol and it is suspected that glycerol could act as a fortuitous inducer of the mtl promoter if the concentration of glycerol is sufficiently high. The hypothesis was tested by performing shake-flask experiments with strain DC283 ΔmtlDYZ/pDOW1339 pDOW1365-1 in medium with 12.5% glucose and adding glycerol instead of mannitol at various concentrations at the time of induction. Mannitol was added as an inducer to control flasks. Induction was performed at 12 h EFT instead of 24 h EFT to prevent interference from the pH shift that may occur at later time points in glucose-grown cultures.

Figure 14:
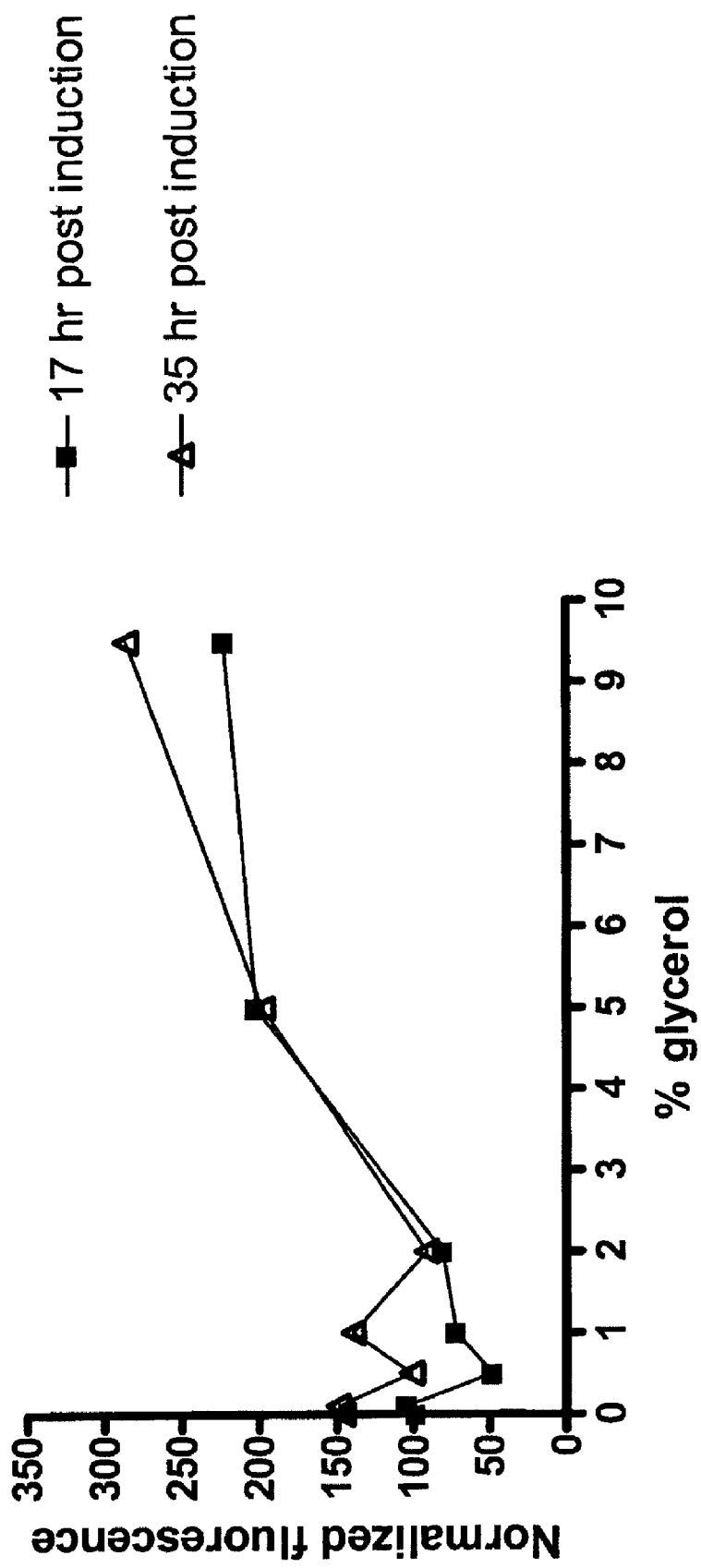
FIG. 14 illustrates Pmtl activity in glucose-grown cultures after induction with glycerol. The strain DC283 ΔmtlDYZ/pDOW1365-1 pDOW1339 was cultivated in shake-flask medium containing 12.5% glucose. Various concentrations of glycerol (0, 0.1%, 0.5%, 1%, 2%, 5%, 9.5%) were added at 12 h EFT and fluorescence was measured over time on normalized samples (above). The fluorescence level at 17 h (squares) or 35 h (triangles) were plotted.

When the glycerol inducer concentration was 2% or below, the promoter activity was not detectably different from no additions. At higher glycerol concentrations (5% and 9.5%) fluorescence increased to 2 to 3 times above background levels (FIG. 14) by 17 hr after induction. This result clearly demonstrates that glycerol can induce mtl promoter activity (although at lower level than mannitol) which resulted in CopGFP expression and explains the background fluorescence observed in medium containing a high glycerol concentration.

Example 8

Figure 15:
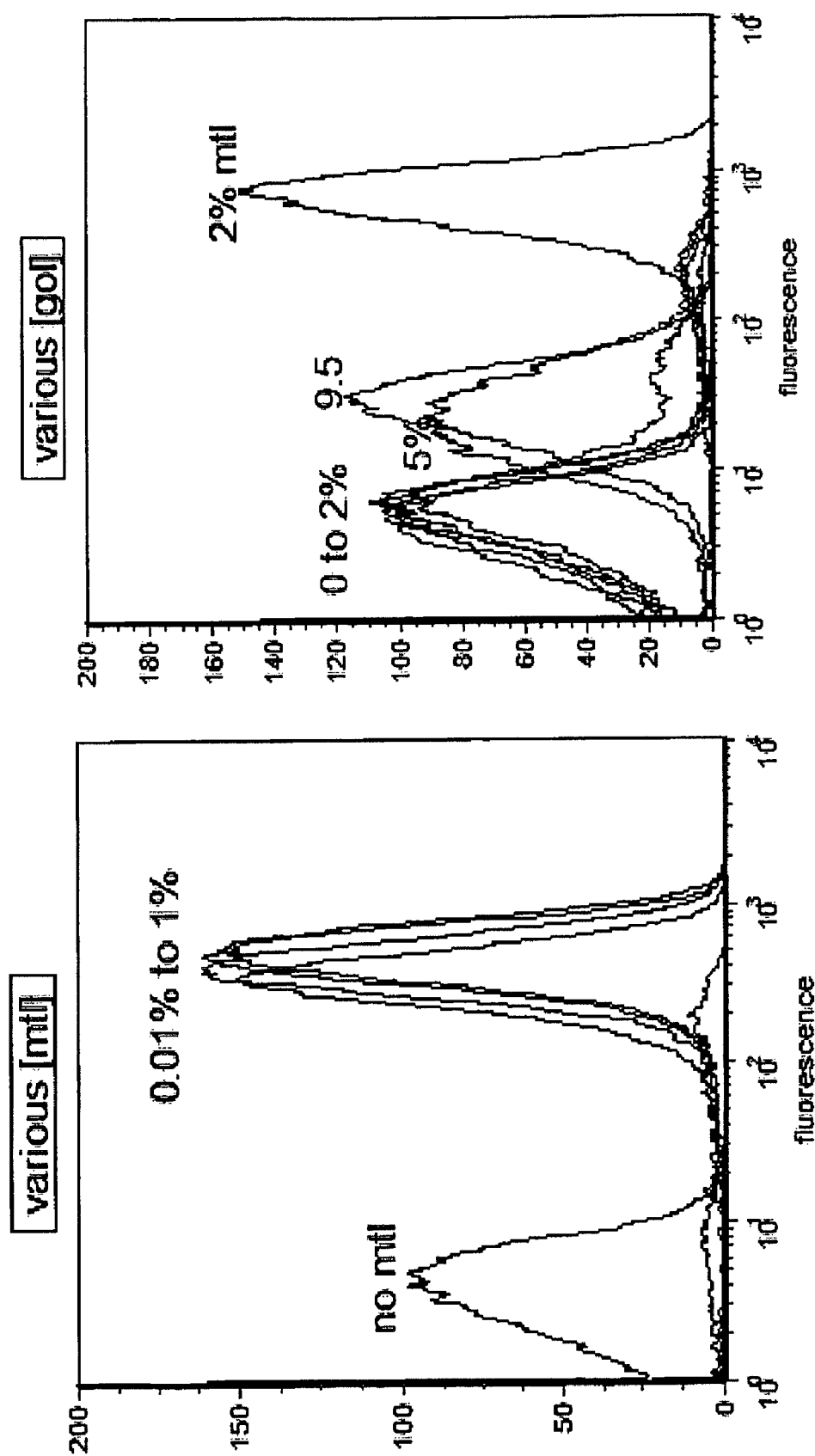
FIG. 15 illustrates a flow cytometry analysis using varying concentrations of inducer. Fluorescence of the cells from glucose-grown cultures induced with varying levels of mannitol (see FIG. 13) (a) or with glycerol (see FIG. 14) (b) were analyzed by flow cytometry and the results overlaid in a histogram. The x-axis is fluorescence and the y-axis is cell count at each fluorescence value. For comparison, fluorescence after induction with 2% mannitol is included in (b).

Uniform Induction of the mtl Promoter at Less than Saturating Inducer Concentrations A portion of the shake-flask cultures from Examples 6 and 7 were analyzed by flow cytometry in order to determine whether sub-saturating levels of inducer created a bimodal "all-or-none" style of induction, or whether induction was uniform among all cells. In the cultures tested, with 0 to 1% mannitol as an inducer, or 0 to 9.5% glycerol as an inducer, in cultures using glucose as the carbon source, the distribution of fluorescence created a single, normal-shaped distribution (FIG. 15), indicating that all cells were induced to a similar level within a culture.

Example 9 mtl Promoter Activity in 20-L Fermentors

Figure 16:
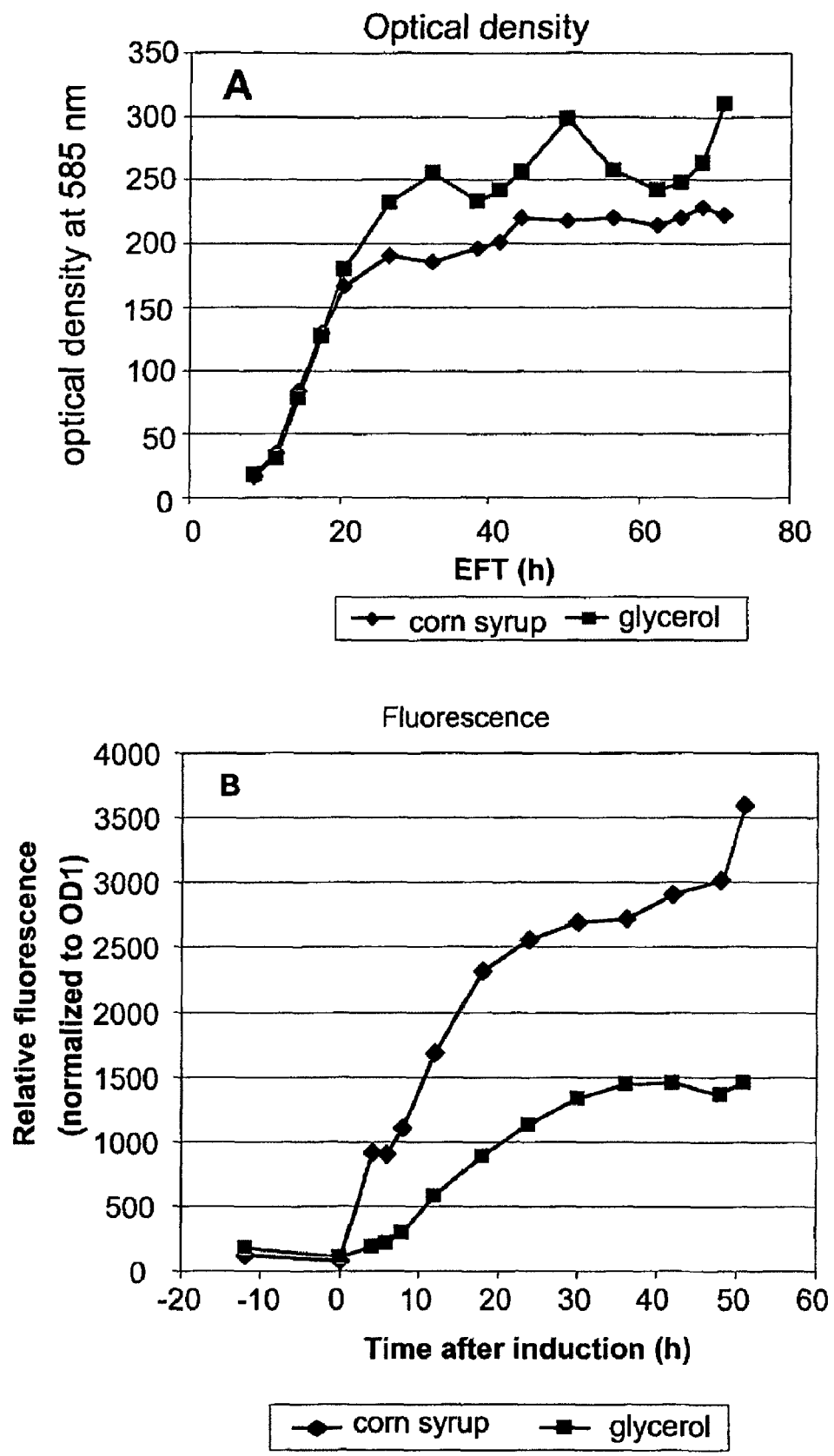
FIG. 16 illustrates the induction by mannitol of CopGFP Pmtl in 20-L corn syrup (glucose) or glycerol fermentor cultures. Optical densities (A) and fluorescence (B) analysis of strain DC283 ΔmtlDYZ/pDOW1365-1 pDOW1339 (=DC390) grown in 20 L-fermentors with corn syrup (glucose) (diamonds) or glycerol (squares) is shown. Cultures were induced with 1% mannitol at 20.5 h EFT and optical density at 575 nm and fluorescence were measured over time on normalized samples.

Strain DC390 (=DC283ΔmtlDYZ/pDOW1365-1 pDOW1339) was cultivated in 20 L-fermentors in mineral salts medium with either glycerol or corn syrup (glucose) as sole carbon source. Glycerol and glucose were spiked frequently into the medium at various time points according to a standardized feeding regimen that is dependent on the cells' oxygen uptake rate. The concentration of glycerol or glucose never exceeded 1% and 0.1%, respectively, and the pH of the culture medium was kept constant at 6.5. In medium with glycerol, the culture reached an optical density $OD_{575}$ of about 250. The maximum optical density was slightly lower ($OD_{575}$ about 230), when cells were grown with corn syrup (FIG. 16a).

Figure 17:
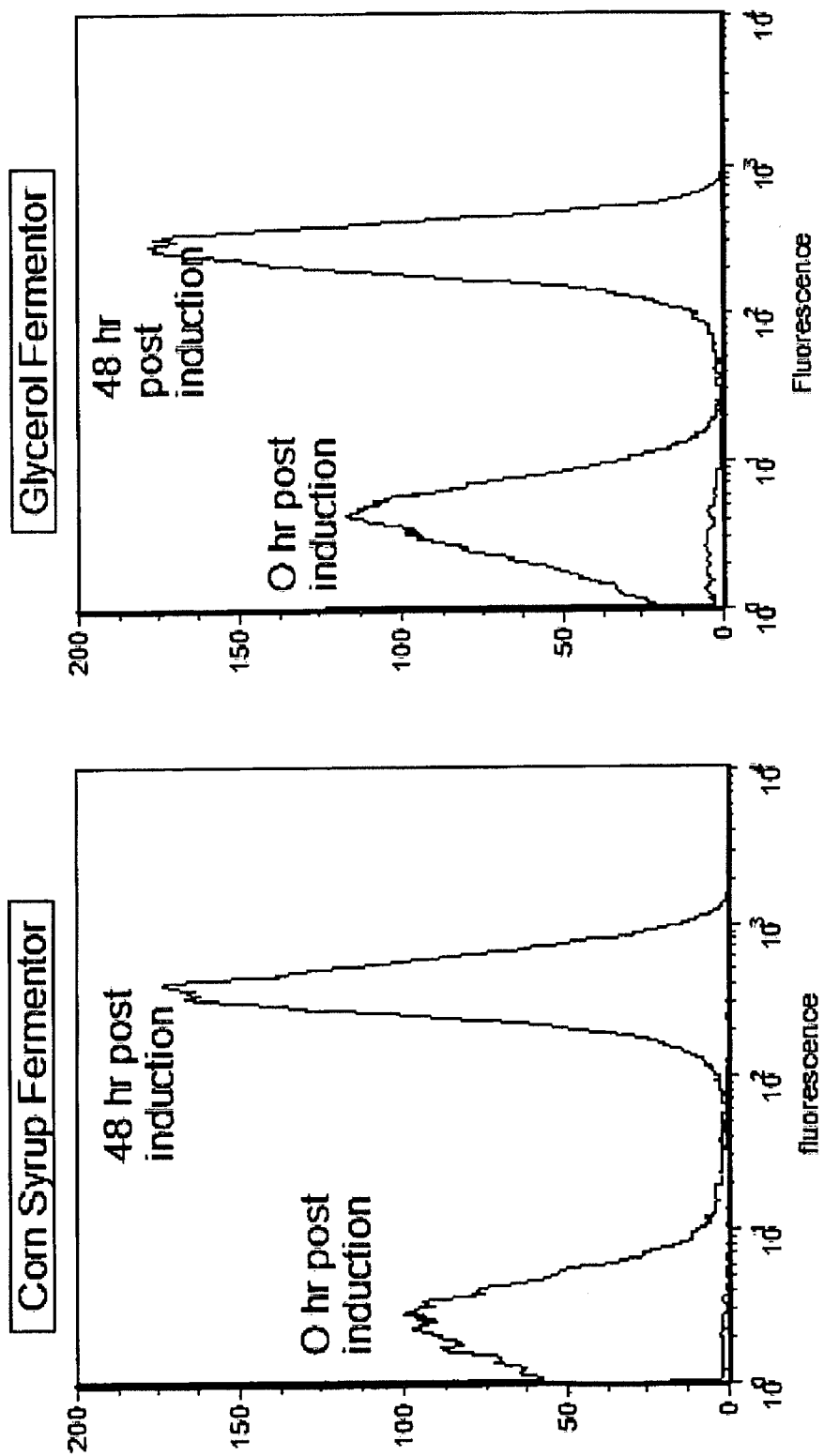
FIG. 17 illustrates a flow cytometry analysis of the induction by mannitol of expression of CopGFP from Pmtl in 20-L corn syrup (glucose) or glycerol fermentor cultures. Flow cytometry analysis of strain DC283 ΔmtlDYZ/pDOW1365-1 pDOW1339 (=DC390) grown in 20 L-fermentors with corn syrup (glucose) (above) or glycerol (below). Cultures were induced with 1% mannitol at 20.5 h EFT. Samples were removed for flow cytometry analysis at 0 and 48 hr after induction. The x-axis of the histogram is fluorescence and the y-axis is cell count at each fluorescence value.

At an optical density of about 170 at 20.5 hours elapsed fermentation time (EFT), fermentor cultures were induced with 1% (w/v) mannitol. As shown in (FIG. 16b), cell fluorescence increased to about 3000 RFUs in medium with corn syrup and to about 1500 RFUs in medium with glycerol. Both background fluorescence, increase in fluorescence over time, and maximum RFUs were comparable to results obtained in shake-flask experiments with 12.5% glucose (maximum 3500 RFUs) or 2% glycerol (maximum 1000 RFUs) (data not shown), i.e., the depressed levels were low. Peptide analysis by SDS-PAGE demonstrated the appearance of CopGFP (with an expected molecular size of 25 kDa) after induction with mannitol (data not shown). In both fermentors, expression of CopGFP among cells in the culture was uniformly induced, as assessed by flow cytometry (FIG. 17).

Example 10

Use of the mtl Promoter to Co-Express Folding Modulators GrpE, DnaK and DnaJ to Increase Human Growth Hormone Solubility Human growth hormone (hGH), when expressed in *P. fluorescens*, accumulates almost entirely as insoluble inclusion bodies. Based on transcriptional profiling data, the expression of *P. fluorescens* folding modulators (FMs) DnaK and DnaJ was increased in strains after induction of expression of recombinant hGH and accumulation as inclusion bodies in the cytoplasm of *P. fluorescens*, compared to strains that did not express the target protein (see, for example, U.S. Provisional Application No. 60/591,489). We therefore engineered a strain with the putative operon encoding GrpE, DnaK and DnaJ under control of the mtl promoter on a plasmid in order to co-express the FMs with hGH.

Using chromosomal DNA isolated from MB214 (DNeasy; Qiagen, Valencia, Calif.) as a template and primers RC199 (SEQ ID NO:28) and RC200 (SEQ ID NO:29), grpE dnaKJ were amplified using PfuTurbo (Stratagene, La Jolla, Calif.) as per the manufacturer's recommendations. The resulting PCR product (4 kb) was digested with SpeI and XbaI (restriction sites underlined in the primers above) and ligated to pDOW2236 (a derivative of pDOW1306-6) (Schneider, J. C., A. F. Jenings, D. M. Mun, P. M. McGovern and L. C. Chew (2005). "Auxotrophic markers pyrF and proC can replace antibiotic markers on protein production plasmids in high-cell-density *Pseudomonas fluorescens* fermentation." Biotech Prog 21: 343-348) to create pDOW2240 containing the grpEdnaKJ operon under control of the tac promoter. pDOW2240 was digested with SpeI and HinIII and the resulting grpEdnaKJ-containing 4.0 kb fragment was gel-purified using Qiaquick (Qiagen, Valencia, Calif.) and ligated to pDOW2247 (a derivative of pDOW1365-1) also digested with SpeI and HindIII. The resulting plasmid, pDOW3501, containing grpEdnaKJ under the control of the mannitol promoter, was transformed into DC388 by selecting on M9glucose plates supplemented with 250 µg/ml uracil. Finally, pDOW1426 was electroporated into the above strain (DC462) and selected on M9 glucose plates, resulting in strain DC463 with two inducible plasmids: 1) pDOW1426 carrying $P_{tac}$hGH and 2) pDOW3501 carrying $P_{mtl}$grpEdnaKJ.

TABLE 10

Oligonucleotides with engineered restriction sites are underlined.

| Oligo-nucleotide | Sequence | SEQ. ID. |
|---|---|---|
| RC199 | 5' ATAT<u>ACTAGT</u>AGGAGGTAACTTATGGCTGACGAACAGACGCA | 28 |
| RC200 | 5' ATAT<u>TCTAGA</u>TTACAGGTCGCCGAAGAAGC | 29 |

Duplicate cultures of DC463 were grown in mineral salts medium and $OD_{600}$ was recorded for each culture at various time points. Induction was accomplished by addition of 0.1 mM IPTG for hGH and 0.5% mannitol for GrpEDnaKJ at varying times after inoculation. Samples were collected at 0, 4, 8, 24 and 48 hours after induction. At each time point, 20 $OD_{600}$ normalized in 1 mL was harvested, lysed using EasyLyse™ (Epicentre, Madison, Wis.) and separated into soluble and insoluble fractions by centrifugation at 14000 rpm for 30 minutes. Equal volumes of samples were combined with Bio-Rad (Hercules, Calif.) 2× Laemmli buffer, heated at 95° C. for 5 minutes with 30 µL loaded onto a BioRad 15% Tris-HCl Criterion gel using 1× Tris Glycine SDS running buffer (Bio-Rad). The proteins were visualized with Simply Blue Safestain (Invitrogen, Carlsbad, Calif.) and hGH production was quantitated using Prediluted BSA standards (Pierce Biotechnology, Rockford, Ill.) loaded on the same gel. The resulting Coomassie stained gels were scanned using a Molecular Devices Personal Densitometer (Molecular Devices, Sunnyvale, Calif.) with analyses performed using ImageQuant and Excel. As shown in Table 11, co-expression of GrpE DnaKJ significantly increased the solubility of hGH, converting almost 100% of the target protein into the soluble fraction. Additional experiments repeating growth and induction of DC463 using the simultaneous addition of IPTG and mannitol closely mimicked the results shown here, with 50-100% of hGH found in the soluble fraction (data not shown) when co-overexpressed with GrpE DnaKJ, compared to 100% insoluble otherwise. These results were observed for either the simultaneous addition of IPTG and mannitol, or staggered addition, but cell density for cultures with early induction of GrpE DnaKJ did not grow as well, indicating that a high level of expression of these FMs is deleterious to cell health. Since lower levels of expression may be optimal for the least deleterious effect on cell metabolism and highest yield of soluble hGH; the control of these FM genes from a promoter that is regulated independently of the target protein will allow independent optimization of expression.

TABLE 11

Quantitation of hGH resulting from from co-expression with GrpE, DnaKJ

| | hGH accumulation (mg/mL) | | | |
|---|---|---|---|---|
| | $I_{24}$ soluble | $I_{24}$ insoluble | $I_{48}$ soluble | $I_{48}$ insoluble |
| hGH induced at 24 hr EFT | 0.05 | 0.51 | 0.03 | 0.95 |
| hGH, GrpE DnaKJ induced at 24 hr EFT* | 0.24 | 0.02 | 0.29 | 0.04 |
| hGH induced at 24 hr EFT, GrpE DnaKJ induced at 8 hr EFT | 0.17 | 0 | 0.21 | 0 |
| GrpE, DnaKJ induced at 24 hr EFT | 0 | 0 | 0 | 0 |

The values listed here are the average of duplicate flasks, shown in mg/ml, based on the densitometry results shown in Figure x. Only hGH corresponding bands were quantitated in each lane.
*EFT refers to elapsed fermentation time.

---

What is claimed is:

1. A method for expressing a recombinant polypeptide in a *Pseudomonas fluorescens* host cell comprising:
   a) providing a *Pseudomonas fluorescens* host cell;
   b) transforming the *Pseudomonas fluorescens* host cell with at least one nucleic acid construct encoding a recombinant polypeptide operably linked to a mannitol-inducible promoter comprising the promoter of an endogenous *Pseudomonas fluorescens* mtlEFGKDYZ operon;
   c) growing the *Pseudomonas fluorescens* host cell in a growth medium;
   d) adding a carbon source to the growth medium;
   e) expressing the recombinant polypeptide of interest by inducing the mannitol-inducible promoter; and,
   f) isolating the expressed recombinant polypeptide;
   wherein the *Pseudomonas fluorescens* host cell has a mutation or deletion of a gene selected from the group consisting of mtlD, mtlY, and mtlZ, or a combination thereof.

2. The method of claim 1, wherein the mannitol-inducible promoter comprises the nucleic acid sequence selected from the group consisting of;
   a) SEQ ID NO: 9;
   b) SEQ ID NO: 12; and
   c) a nucleic acid sequence having at least 95% sequence identity to the nucleic acid sequence set forth in SEQ ID NO: 9 or SEQ ID NO: 12;
   wherein the nucleic acid sequence of (c) encodes an mtl promoter.

* * * * *

SEQUENCE LISTING

<160> NUMBER OF SEQ ID NOS: 34

<210> SEQ ID NO 1
<211> LENGTH: 29
<212> TYPE: DNA
<213> ORGANISM: Pseudomonas fluorescens

<400> SEQUENCE: 1
ttgtcacaac cccgtttgaa ggctgtaat                              29

<210> SEQ ID NO 2
<211> LENGTH: 29
<212> TYPE: DNA
<213> ORGANISM: Pseudomonas fluorescens

<400> SEQUENCE: 2
ttgtcaccgc cgtttttgaa ggctgtaat                              29

<210> SEQ ID NO 3

```
<211> LENGTH: 29
<212> TYPE: DNA
<213> ORGANISM: Pseudomonas fluorescens

<400> SEQUENCE: 3
ttgtcagccc tgcgtcagaa ggctgtaat                                    29

<210> SEQ ID NO 4
<211> LENGTH: 28
<212> TYPE: DNA
<213> ORGANISM: Pseudomonas fluorescens

<400> SEQUENCE: 4
ttgtcggttg cgtgacgcgc ctgtgtaa                                     28

<210> SEQ ID NO 5
<211> LENGTH: 40
<212> TYPE: DNA
<213> ORGANISM: Pseudomonas fluorescens

<400> SEQUENCE: 5
acgagtgcaa aaaagtatca gtaagcgtgc tcccaaggat                        40

<210> SEQ ID NO 6
<211> LENGTH: 40
<212> TYPE: DNA
<213> ORGANISM: Pseudomonas fluorescens

<400> SEQUENCE: 6
acgagtgcaa aaagtatca gtccaagtgc tcccaaggat                         40

<210> SEQ ID NO 7
<211> LENGTH: 40
<212> TYPE: DNA
<213> ORGANISM: Pseudomonas fluorescens

<400> SEQUENCE: 7
ccgagtgcaa aaagtatcg attcaagtgc tagggatgat                         40

<210> SEQ ID NO 8
<211> LENGTH: 40
<212> TYPE: DNA
<213> ORGANISM: Pseudomonas fluorescens

<400> SEQUENCE: 8
ggcggtgcaa aaagtatcg gtcgaagtgc agtcgaggct                         40

<210> SEQ ID NO 9
<211> LENGTH: 299
<212> TYPE: DNA
<213> ORGANISM: Pseudomonas fluorescens

<400> SEQUENCE: 9
gagcgtggga acgatcaagt gttaaacact gcactgagga tcgttcccgc gctccgcgtg    60
ggcatgcata ccgtgacgct ctgcgtcacc tggggacgca gagcgtccct agcggcgtta   120
ccacgcggag cgtgggaacg atcaggtggt cgacgagtgc aaaaaagtat cagtaagcgt   180
gctcccaagg atttgtcacc gccgtttttg aaggctgtaa tcaacgcaca ctcttcctga   240
ctccttgtag gaagacacaa caacaataac cgtccttctg tagccctctg ggcgcggaa    299

<210> SEQ ID NO 10
<211> LENGTH: 203
<212> TYPE: DNA
```

<213> ORGANISM: Pseudomonas fluorescens

<400> SEQUENCE: 10

```
tgagcaggaa aatctgtacg gtttcgcgcc cttcgccatg ctgaaacgcc cttccctgcg    60
gttatcgcgc caatcccgag tgcaaaaaag tatcgattca agtgctaggg atgatttgtc   120
agccctgcgt cagaaggctg taatcagtgc acattcttcc cccgccggaa gaacacaaaa   180
acaataactg tccttctgcc ccc                                           203
```

<210> SEQ ID NO 11
<211> LENGTH: 126
<212> TYPE: DNA
<213> ORGANISM: Pseudomonas fluorescens

<400> SEQUENCE: 11

```
taagcgtgct cccaaggatt tgtcaccgcc gttttttgaag gctgtaatca acgcacactc    60
ttcctgactc cttgtaggaa gacacaacaa caataaccgt ccttctgtag ccctctgggc   120
gcggaa                                                              126
```

<210> SEQ ID NO 12
<211> LENGTH: 147
<212> TYPE: DNA
<213> ORGANISM: Pseudomonas fluorescens

<400> SEQUENCE: 12

```
acgagtgcaa aaaagtatca gtaagcgtgc tcccaaggat tgtcaccgc cgttttttgaa    60
ggctgtaatc aacgcacact cttcctgact ccttgtagga agacacaaca acaataaccg   120
tccttctgta gccctctggg cgcggaa                                       147
```

<210> SEQ ID NO 13
<211> LENGTH: 77
<212> TYPE: DNA
<213> ORGANISM: Pseudomonas fluorescens

<400> SEQUENCE: 13

```
acgagtgcaa aaaagtatca gtaagcgtgc tcccaaggat tgtcaccgc cgttttttgaa    60
ggctgtaatc aacgcac                                                   77
```

<210> SEQ ID NO 14
<211> LENGTH: 32
<212> TYPE: DNA
<213> ORGANISM: Artificial Sequence
<220> FEATURE:
<223> OTHER INFORMATION: Primer mtlE3

<400> SEQUENCE: 14

```
atatgagctc gagcgtggga acgatcaagt gt                                  32
```

<210> SEQ ID NO 15
<211> LENGTH: 30
<212> TYPE: DNA
<213> ORGANISM: Artificial Sequence
<220> FEATURE:
<223> OTHER INFORMATION: Primer mtlE4

<400> SEQUENCE: 15

```
atatccgcgg ttccgcgccc agagggctac                                     30
```

<210> SEQ ID NO 16
<211> LENGTH: 35
<212> TYPE: DNA

```
<213> ORGANISM: Artificial Sequence
<220> FEATURE:
<223> OTHER INFORMATION: Primer mtlE5

<400> SEQUENCE: 16
atatgagctc taagcgtgct cccaaggatt tgtca                               35

<210> SEQ ID NO 17
<211> LENGTH: 30
<212> TYPE: DNA
<213> ORGANISM: Artificial Sequence
<220> FEATURE:
<223> OTHER INFORMATION: Primer mtlE6

<400> SEQUENCE: 17
atatgagctc tgagcaggaa aatctgtacg                                     30

<210> SEQ ID NO 18
<211> LENGTH: 30
<212> TYPE: DNA
<213> ORGANISM: Artificial Sequence
<220> FEATURE:
<223> OTHER INFORMATION: Primer mtlE7

<400> SEQUENCE: 18
atatccgcgg gggggcagaa ggacagttat                                     30

<210> SEQ ID NO 19
<211> LENGTH: 35
<212> TYPE: DNA
<213> ORGANISM: Artificial Sequence
<220> FEATURE:
<223> OTHER INFORMATION: Primer mtlE9

<400> SEQUENCE: 19
atatgagctc acgagtgcaa aaaagtatca gtaag                               35

<210> SEQ ID NO 20
<211> LENGTH: 33
<212> TYPE: DNA
<213> ORGANISM: Artificial Sequence
<220> FEATURE:
<223> OTHER INFORMATION: Primer mtlE11

<400> SEQUENCE: 20
atatccgcgg gtgcgttgat tacagccttc aaa                                 33

<210> SEQ ID NO 21
<211> LENGTH: 25
<212> TYPE: DNA
<213> ORGANISM: Artificial Sequence
<220> FEATURE:
<223> OTHER INFORMATION: Primer man1

<400> SEQUENCE: 21
gccgacaagg tagtggtgct caaca                                          25

<210> SEQ ID NO 22
<211> LENGTH: 30
<212> TYPE: DNA
<213> ORGANISM: Artificial Sequence
<220> FEATURE:
<223> OTHER INFORMATION: Primer man2

<400> SEQUENCE: 22
tgcccgctcg cctcacatcg ggaaatactc                                     30
```

<210> SEQ ID NO 23
<211> LENGTH: 30
<212> TYPE: DNA
<213> ORGANISM: Artificial Sequence
<220> FEATURE:
<223> OTHER INFORMATION: Primer man3

<400> SEQUENCE: 23
gagtatttcc cgatgtgagg cgagcgggca                                    30

<210> SEQ ID NO 24
<211> LENGTH: 25
<212> TYPE: DNA
<213> ORGANISM: Artificial Sequence
<220> FEATURE:
<223> OTHER INFORMATION: Primer man4

<400> SEQUENCE: 24
accgatagtg ccaccgctct ggtag                                         25

<210> SEQ ID NO 25
<211> LENGTH: 20
<212> TYPE: DNA
<213> ORGANISM: Artificial Sequence
<220> FEATURE:
<223> OTHER INFORMATION: Primer H3seq

<400> SEQUENCE: 25
gtcctgcaat ttcagcccga                                               20

<210> SEQ ID NO 26
<211> LENGTH: 20
<212> TYPE: DNA
<213> ORGANISM: Artificial Sequence
<220> FEATURE:
<223> OTHER INFORMATION: Primer man5

<400> SEQUENCE: 26
tgttcgacga accgctgtcc                                               20

<210> SEQ ID NO 27
<211> LENGTH: 27
<212> TYPE: DNA
<213> ORGANISM: Artificial Sequence
<220> FEATURE:
<223> OTHER INFORMATION: Primer man6

<400> SEQUENCE: 27
ttcaatggtc ccccggtca tttcata                                        27

<210> SEQ ID NO 28
<211> LENGTH: 42
<212> TYPE: DNA
<213> ORGANISM: Artificial Sequence
<220> FEATURE:
<223> OTHER INFORMATION: Primer RC199

<400> SEQUENCE: 28
atatactagt aggaggtaac ttatggctga cgaacagacg ca                      42

<210> SEQ ID NO 29
<211> LENGTH: 30
<212> TYPE: DNA
<213> ORGANISM: Artificial Sequence
<220> FEATURE:
<223> OTHER INFORMATION: Primer RC200

```
<400> SEQUENCE: 29
atattctaga ttacaggtcg ccgaagaagc                                      30

<210> SEQ ID NO 30
<211> LENGTH: 63
<212> TYPE: DNA
<213> ORGANISM: Pseudomonas fluorescens
<220> FEATURE:
<221> NAME/KEY: misc_feature
<222> LOCATION: 7, 8, 9, 10, 11, 12, 13, 14, 15, 16, 17, 18, 19, 20, 21,
      22, 23, 30, 31, 32, 33, 34, 35, 36, 37, 38, 39
<223> OTHER INFORMATION: n = A,T,C or G

<400> SEQUENCE: 30
ttgtcannnn nnnnnnnnnn nnntgtaatn nnnnnnnnnt cttcctgact ccccgtagga    60
aga                                                                  63

<210> SEQ ID NO 31
<211> LENGTH: 173
<212> TYPE: DNA
<213> ORGANISM: Pseudomonas fluorescens

<400> SEQUENCE: 31
acgagtgcaa aaaagtatca gtccaagtgc tcccaaggat ttgtcacaac cccgtttgaa    60
ggctgtaatc aacgcacact cttcctgact ccccgtagga agacacaaca acaataactg   120
tccttccgta gcccctgggc gcggaaatgg agtgcgcgat gaagttcaca gca          173

<210> SEQ ID NO 32
<211> LENGTH: 174
<212> TYPE: DNA
<213> ORGANISM: Pseudomonas fluorescens

<400> SEQUENCE: 32
acgagtgcaa aaaagtatca gtaagcgtgc tcccaaggat ttgtcaccgc cgttttgaa    60 ggctgtaatc aacgcacact cttcctgact ccccgtagga agacacaaca acaataaccg   120
tccttctgta gccctctggg cgcggaaatg gagtgcgcga tgaagttcac agca         174

<210> SEQ ID NO 33
<211> LENGTH: 169
<212> TYPE: DNA
<213> ORGANISM: Pseudomonas fluorescens

<400> SEQUENCE: 33
ccgagtgcaa aaaagtatcg attcaagtgc tagggatgat ttgtcagccc tgcgtcagaa    60
ggctgtaatc agtgcacatt cttcccccgc cggaagaaca caaaaacaat aactgtcctt   120
ctgccccccg ccgggtgcag aaaaggagtg cacgatgcaa cccactgca               169

<210> SEQ ID NO 34
<211> LENGTH: 153
<212> TYPE: DNA
<213> ORGANISM: Pseudomonas fluorescens

<400> SEQUENCE: 34
ggcggtgcaa aaagtatcg gtcgaagtgc agtcgaggct ttgtcggttg cgtgacgcgc    60
ctgtgtaatc ggcagcgagc gacacaaaaa caataatgtc ttccgcgccg cccgccggcc   120
cggaagagga gttcaccgat gaacgactcg atc                                153
```